United States Patent
Lin

(10) Patent No.: US 10,751,324 B2
(45) Date of Patent: Aug. 25, 2020

(54) TREATMENT OF TNF-ALPHA CYTOTOXICITY

(71) Applicant: The University of Chicago, Chicago, IL (US)

(72) Inventor: Anning Lin, Chicago, IL (US)

(73) Assignee: The University of Chicago, Chicago, IL (US)

(*) Notice: Subject to any disclaimer, the term of this patent is extended or adjusted under 35 U.S.C. 154(b) by 0 days.

(21) Appl. No.: 16/329,499

(22) PCT Filed: Sep. 1, 2017

(86) PCT No.: PCT/US2017/049802
§ 371 (c)(1),
(2) Date: Feb. 28, 2019

(87) PCT Pub. No.: WO2018/045258
PCT Pub. Date: Mar. 8, 2018

(65) Prior Publication Data
US 2019/0192484 A1  Jun. 27, 2019

Related U.S. Application Data

(60) Provisional application No. 62/382,829, filed on Sep. 2, 2016.

(51) Int. Cl.
*A61K 31/517* (2006.01)
*A61K 31/4155* (2006.01)
(Continued)

(52) U.S. Cl.
CPC ...... *A61K 31/4155* (2013.01); *A61K 31/7105* (2013.01); *A61P 19/02* (2018.01);
(Continued)

(58) Field of Classification Search
CPC ............ A61K 31/4155; A61K 31/7105; A61K 31/04; A61K 45/06; A61P 31/04;
(Continued)

(56) References Cited

U.S. PATENT DOCUMENTS

2009/0076025 A1  3/2009  Czarnik
2013/0267484 A1  10/2013  Moussy et al.
(Continued)

FOREIGN PATENT DOCUMENTS

WO  WO 2016/100882  6/2016

OTHER PUBLICATIONS

Beutler et al., Cachectin and tumour necrosis factor as two sides of the same biological coin. Nature. Apr. 17-23, 1986;320(6063):584-8.
(Continued)

*Primary Examiner* — Taylor V Oh
(74) *Attorney, Agent, or Firm* — Casimir Jones, S.C.; Thomas A. Isenbarger

(57) ABSTRACT

Provided herein is technology relating to treating and/or ameliorating TNFα cytotoxicity and particularly, but not exclusively, to compositions, methods, and kits for specifically modulating BCL-2-associated death promoter (BAD) activity, for example, by modulating the activity of Src and/or p190GAP.

20 Claims, 37 Drawing Sheets

Specification includes a Sequence Listing.

(51) Int. Cl.
| | |
|---|---|
| *G01N 33/574* | (2006.01) |
| *G01N 33/50* | (2006.01) |
| *G01N 33/569* | (2006.01) |
| *C12Q 1/6883* | (2018.01) |
| *A61P 37/06* | (2006.01) |
| *A61P 19/02* | (2006.01) |
| *A61P 31/04* | (2006.01) |
| *A61K 31/7105* | (2006.01) |
| *A61K 45/06* | (2006.01) |
| *C07B 59/00* | (2006.01) |

(52) U.S. Cl.
CPC .............. *A61P 31/04* (2018.01); *A61P 37/06* (2018.01); *C12Q 1/6883* (2013.01); *G01N 33/50* (2013.01); *G01N 33/569* (2013.01); *G01N 33/574* (2013.01); *A61K 45/06* (2013.01); *C07B 59/002* (2013.01); *C12Q 2600/156* (2013.01); *G01N 2800/50* (2013.01)

(58) Field of Classification Search
CPC ........ A61P 19/02; A61P 37/06; C07B 59/002; C12Q 1/6883; C12Q 2600/156; G01N 33/569; G01N 2800/50; G01N 33/50; G01N 33/574
USPC .............................................. 514/258, 258.1
See application file for complete search history.

(56) References Cited

U.S. PATENT DOCUMENTS

| | | |
|---|---|---|
| 2013/0330356 A1 | 12/2013 | Salfeld et al. |
| 2014/0286941 A1 | 9/2014 | Banerjee et al. |
| 2014/0302172 A1 | 10/2014 | Schaab et al. |
| 2014/0371233 A1* | 12/2014 | Strittmatter .......... A61K 31/517 514/252.17 |

OTHER PUBLICATIONS

Bourne et al., the GTPase superfamily: a conserved switch for diverse cell functions. Nature. Nov. 8, 1990;348(6297):125-32.
Chang et al., c-Src regulates the simultaneous rearrangement of actin cytoskeleton, p190RhoGAP, and p120RasGAP following epidermal growth factor stimulation. J Cell Biol. Jul. 1995;130(2):355-68.
Guivier et al., Tnf-α expression and promoter sequences reflect the balance of tolerance/resistance to Puumala hantavirus infection in European bank vole populations. Infect Genet Evol. Dec. 2010;10(8):1208-17.
Huang et al., BH3-Only Proteins-Essential Initiators of Apoptotic Cell Death. Cell. Dec. 8, 2000;103(6):839-42.
Kakiashvili et al., the epidermal growth factor receptor mediates tumor necrosis factor-alpha-induced activation of the ERK/GEF-H1/RhoA pathway in tubular epithelium. J Biol Chem. Mar. 18, 2011;286(11):9268-79.
Karin et al., NF-kappaB at the crossroads of life and death. Nat Immunol. Mar. 2002;3(3):221-7.
Lee et al., Overexpression of HO-1 Protects against TNF-α-Mediated Airway Inflammation by Down-Regulation of TNFR1-Dependent Oxidative Stress. Am J Pathol. Aug. 2009; 175(2): 519-532.
Lei et al., JNK Phosphorylation of Bim-related Members of the Bcl2 Family Induces Bax-dependent Apoptosis. Proc Natl Acad Sci U S A. Mar. 4, 2003;100(5):2432-7.
Li et al., The Gβγ-Src signaling pathway regulates TNF-induced necroptosis via control of necrosome translocation. Cell Res. Apr. 2014;24(4):417-32.
Liu et al., c-Jun N-terminal protein kinase 1 (JNK1), but not JNK2, is essential for tumor necrosis factor alpha-induced c-Jun kinase activation and apoptosis. Mol Cell Biol. Dec. 2004;24(24):10844-56.
Liu et al., Wiring the Cell Signaling Circuitry by the NF-kappa B and JNK1 Crosstalk and Its Applications in Human Diseases. Oncogene. May 14, 2007;26(22):3267-78.
Locksley et al., The TNF and TNF receptor superfamilies: integrating mammalian biology. Cell. Feb. 23, 2001;104(4):487-501.
Majetschak et al., Relation of a TNF gene polymorphism to severe sepsis in trauma patients. Ann Surg. Aug. 1999;230(2):207-14.
Mazmanian et al., A microbial symbiosis factor prevents intestinal inflammatory disease. Nature. May 29, 2008;453(7195):620-5.
Melendez et al., RhoA GTPase is dispensable for actomyosin regulation but is essential for mitosis in primary mouse embryonic fibroblasts. J Biol Chem. Apr. 29, 2011;286(17):15132-7.
Ohman et al., Cytokine polymorphisms and severity of tubal damage in women with Chlamydia-associated infertility. J Infect Dis. May 1, 2009;199(9):1353-9.
Ridley et al., rho family GTPase activating proteins p190, bcr and rhoGAP show distinct specificities in vitro and in vivo. EMBO J. Dec. 15, 1993;12(13):5151-60.
Ridley et al., The small GTP-binding protein rac regulates growth factor-induced membrane ruffling. Cell. Aug. 7, 1992;70(3):401-10.
Ridley et al., The small GTP-binding protein rho regulates the assembly of focal adhesions and actin stress fibers in response to growth factors. Cell. Aug. 7, 1992;70(3):389-99.
Rittirsch et al., Immunodesign of experimental sepsis by cecal ligation and puncture. Nat Protoc. 2009;4(1):31-6.
Secher et al., Crucial role of TNF receptors 1 and 2 in the control of polymicrobial sepsis. J Immunol. Jun. 15, 2009;182(12):7855-64.
Smith et al., The TNF receptor superfamily of cellular and viral proteins: activation, costimulation, and death. Cell. Mar. 25, 1994;76(6):959-62.
Tartaglia et al., Two TNF receptors. Immunol Today. May 1992;13(5):151-3.
Tracey et al., Tumor necrosis factor: an updated review of its biology. Crit Care Med. Oct. 1993;21(10 Suppl):S415-22.
Tracey et al., Tumor necrosis factor: a pleiotropic cytokine and therapeutic target. Annu Rev Med. 1994;45:491-503.
Van Zee et al., Tumor necrosis factor soluble receptors circulate during experimental and clinical inflammation and can protect against excessive tumor necrosis factor alpha in vitro and in vivo. Proc Natl Acad Sci U S A. Jun. 1, 1992;89(11):4845-9.
Yan et al., Inactivation of the BH3-only Protein Bad by IKK Inhibits TNFα-induced Apoptosis Independently of NF-$_κ$B Activation. Cell. Jan. 17, 2013;152(1-2):304-15.
Youle et al., the BCL-2 protein family: opposing activities that mediate cell death. Nat Rev Mol Cell Biol. Jan. 2008;9(1):47-59.
International Search Report and Written Opinion for PCT/US2017/049802, dated Jan. 5, 2018, 19 pages.

* cited by examiner

SEQUENCE LISTING

```
<160> NUMBER OF SEQ ID NOS: 19

<210> SEQ ID NO 1
<211> LENGTH: 22
<212> TYPE: RNA
<213> ORGANISM: Artificial sequence
```

```
<220> FEATURE:
<223> OTHER INFORMATION: Synthetic nucleotide

<400> SEQUENCE: 1
agcuccuguu uggaguuuca aa                                               22

<210> SEQ ID NO 2
<211> LENGTH: 20
<212> TYPE: RNA
<213> ORGANISM: Artificial sequence
<220> FEATURE:
<223> OTHER INFORMATION: Synthetic nucleotide

<400> SEQUENCE: 2
ggagaacgac aaggccaugc                                                  20

<210> SEQ ID NO 3
<211> LENGTH: 19
<212> TYPE: RNA
<213> ORGANISM: Artificial sequence
<220> FEATURE:
<223> OTHER INFORMATION: Synthetic nucleotide

<400> SEQUENCE: 3
ggagcgcacc aucuucuuc                                                   19

<210> SEQ ID NO 4
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 4
cacagaaagc atgatccgcg acgt                                             24

<210> SEQ ID NO 5
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 5
cggcagagag gaggttgact ttct                                             24

<210> SEQ ID NO 6
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 6
tcaagtggca tagatgtgga agaa                                             24

<210> SEQ ID NO 7
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 7
tggctctgca ggattttcat g                                                21
```

<210> SEQ ID NO 8
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 8
ccagcttcaa atctcacagc a                                              21

<210> SEQ ID NO 9
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 9
cttctttggg tattgcttgg gatc                                           24

<210> SEQ ID NO 10
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 10
ggttgccaag ccttatcgga                                                20

<210> SEQ ID NO 11
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 11
acctgctcca ctgccttgct                                                20

<210> SEQ ID NO 12
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 12
tccagttgcc ttcttgggac                                                20

<210> SEQ ID NO 13
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 13
gtactccaga agaccagagg                                                20

```
<210> SEQ ID NO 14
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 14
tgaaggacga ggagtacgag c                                             21

<210> SEQ ID NO 15
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 15
ttcgtggatg attgccaagt g                                             21

<210> SEQ ID NO 16
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 16
acgcagcaat cgtgcatttt g                                             21

<210> SEQ ID NO 17
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 17
cctataacga ggtcactgac gg                                            22

<210> SEQ ID NO 18
<211> LENGTH: 18
<212> TYPE: DNA
<213> ORGANISM: Artificial sequence
<220> FEATURE:
<223> OTHER INFORMATION: Synthetic nucleotide

<400> SEQUENCE: 18
aacgacccct tcattgac                                                 18

<210> SEQ ID NO 19
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 19
tccacgacat actcagcac                                                19
```

TREATMENT OF TNF-ALPHA CYTOTOXICITY

This application claims priority to U.S. provisional patent application Ser. No. 62/382,829, filed Sep. 2, 2016, which is incorporated herein by reference in its entirety.

STATEMENT REGARDING FEDERALLY SPONSORED RESEARCH OR DEVELOPMENT

This invention was made with government support under Grant Nos. GM103868 and GM122457 awarded by the National Institutes of Health. The government has certain rights in the invention.

FIELD

Provided herein is technology relating to treating and/or ameliorating TNFα cytotoxicity and particularly, but not exclusively, to compositions, methods, and kits for specifically modulating (e.g., inhibiting, minimizing, reducing, and/or eliminating) BCL-2-associated death promoter (BAD) activity, e.g., by modulating the activity of Src and/or p190GAP.

BACKGROUND

The pro-inflammatory cytokine TNFα has a crucial role in inflammation, immune responses, and apoptosis (1-4). TNFα alone does not typically induce apoptosis under physiological or developmental conditions unless IKK-mediated activation of NF-κB is also impaired (5) because the target gene products of NF-κB inhibit caspases and prevent prolonged JNK1 activation (6, 7). Inactivation of the BH3-only family protein BAD by IKK is also required for suppression of TNFα-induced apoptosis (8). Like other BH3-only family member proteins, BAD is a potent inducer of apoptosis (9). Hypo-phosphorylated BAD translocates from the cytosol to mitochondria to inactivate the anti-apoptotic BCL-2 family members BCL-2 and BCL-xL, which results in the increased activity of the pro-apoptotic BCL-2 family members BAK and BAX to induce apoptosis (10, 11). Phosphorylation of BAD by IKK at Ser26 primes BAD to be further phosphorylated at Ser112, Ser136, and Ser155 by other protein kinases (e.g., Akt and PKA), which results in the sequestration of BAD in cytosol by association with the phospho-Ser/Thr anchoring protein 14-3-3 (8, 10-12).

TNFα cytotoxicity has long been recognized to have a crucial role in the pathologies of inflammatory disease, infectious disease, autoimmune disease, and cancer (13, 14). However, the mechanism underlying TNFα cytotoxicity is not known. Furthermore, little is known about the genetics and chemical perturbations of TNFα cytotoxicity and IKK signaling pathways in diseases associated with TNFα-induced tissue or organ damage.

SUMMARY

Accordingly, provided herein is technology related to treating and/or ameliorating TNFα cytotoxicity and particularly, but not exclusively, to compositions, methods, and kits for specifically ameliorating TNFα cytotoxicity, e.g., by modulating (e.g., minimizing, reducing, and/or eliminating) BAD activity. In particular, the technology provided herein is related to compositions, methods, and kits for controlling TNFα cytotoxicity through the regulation of TNFα-induced re-distribution of the BCL-2 family protein BAD from cytoskeleton to cytosol. In some embodiments, blockade of BAD prevents the TNFα-induced cytotoxicity that is responsible, e.g., for tissue or organ damage, e.g., in sepsis and other diseases. In some embodiments, the technology finds use in screens for factors (e.g., small molecules and other agents such as, e.g., siRNA) that can prevent, block, reduce, or antagonize TNFα-induced BAD re-distribution. In some embodiments, the technology finds use in preventing or treating diseases or to increase a healthy individual's disease tolerance, e.g., by eliminating, inhibiting, or reducing BAD pro-apoptotic activity or protein level by introducing certain factors (e.g., small molecules and other agents such as, e.g., siRNA) to the individual, subject, or patient.

In particular, experiments were conducted to understand the role of high dose TNFα in apoptosis. In particular, data were collected during the development of embodiments of the technology that indicated that a high dose (e.g., approximately 80 ng/ml, e.g., 50 ng/ml to 100 ng/ml, e.g., 50, 55, 60, 65, 70, 75, 80, 85, 90, 95, or 100 or more ng/ml) but not a low dose (e.g., 5 ng/ml, e.g., 1 ng/ml to 10 ng/ml, e.g., 1, 2, 3, 4, 5, 6, 7, 8, 9, or 10 ng/ml) of TNFα significantly induced apoptosis in wild type (WT) primary hepatocytes, thymocytes, macrophages, splenocytes, and immortalized mouse embryonic fibroblasts (MEFs) (FIG. 1A). The cytotoxicity of high dose TNFα was blocked in primary hepatocytes lacking a primary TNFα receptor TnfR1, thereby excluding the potential off-target effects. By contrast, high dose TNFα did not induce apoptosis in Bad-deficient cells (FIG. 1A), indicating that BAD is required for the TNFα-induced apoptosis. Data further indicated that a high ("cytotoxic" hereinafter) dose of TNFα but not low ("non-cytotoxic" hereinafter) dose of TNFα induced translocation of BAD from the cytosol to mitochondria (FIG. 1B). The data indicated that the translocation of BAD to mitochondria was not the result of defective activation of IKK (FIG. 1C) or NF-κB. Data indicated that loss of JNK1, Casp-8, BID, or BIM, all of which are involved in a TNFα receptor-dependent death pathway (6-7), had no detectable effects on cytotoxic dose TNFα-induced apoptosis, but did inhibit non-cytotoxic dose TNFα-induced apoptosis when NF-κB activation was impaired. By contrast, knockdown of BAD inhibited cytotoxic dose TNFα-induced apoptosis, but did not affect the non-cytotoxic dose TNFα-induced apoptosis. Thus, the data collected during the development of embodiments of the technology described herein indicated that cytotoxic dose TNFα-induced apoptosis is mediated by a BAD-dependent mitochondrial pathway despite concurrent activation of IKK and NF-κB, which is distinct from the classic TNFα receptor-dependent death pathway currently understood in the art.

Furthermore, data collected from experiments conducted during the development of embodiments of the technology provided herein and previous results have indicated that cytotoxic dose TNFα inactivates the RhoA protein by stimulating strong and sustained Src-dependent activation of p190GAP. The inactivation of RhoA results in depolymerization of F-actin filaments and release of BAD into the cytosol at a level that is not completely phosphorylated by IKK. The non-phosphorylated BAD translocates to the mitochondria, where it promotes apoptosis. Activation of the Scr-p190GAP pathway by cytotoxic dose TNFα strongly inactivates RhoA and, consequently, promotes actin depolymerization and release of BAD into the cytosol. And, as shown in the examples, inhibition of Src or p190GAP significantly reduced cytotoxic dose TNFα-induced depolymerization of actin and thus also reduced release of BAD into the cytosol. Accordingly, in some embodiments the technology provided herein relates to inhibiting Src or p190GAP to ameliorate (e.g., reduce, minimize, and/or eliminate) the cytotoxic effects of TNFα, e.g., as mediated by BAD translocation to mitochondria and subsequent apoptosis.

Accordingly, provided herein is technology related to a method of treating TNFα-related cytotoxicity in a subject. In particular, methods are provided comprising administering an inhibitor of Src to the subject. In some embodiments, the inhibitor of Src is a nucleic acid or a protein. In some embodiments, the inhibitor of Src is a small molecule. In some embodiments, the inhibitor of Src is a deuterated small molecule inhibitor of Src. In some embodiments, the inhibitor of Src is a compound as provided in Table 1 (e.g., ZG5126, ZG5127, ZG5128, ZG5129, ZG5130, ZG5131, ZG5132, ZG5133, ZG5134, ZG5146, ZG5147, or ZG5151). In some embodiments, the inhibitor of Src is dasatinib or saracatinib.

For example, in some embodiments, compositions comprise a compound having a structure according to:

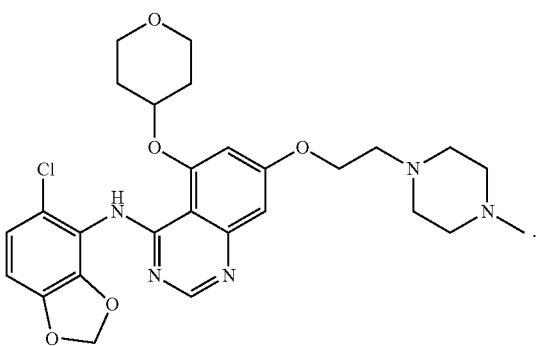 [SMILES: CN1CCN(CCOc2cc(OC3CCOCC3)c3c(Nc4c(Cl)ccc5c4OCO5)ncnc3c2)CC1]

In some embodiments, compositions comprise a compound according to

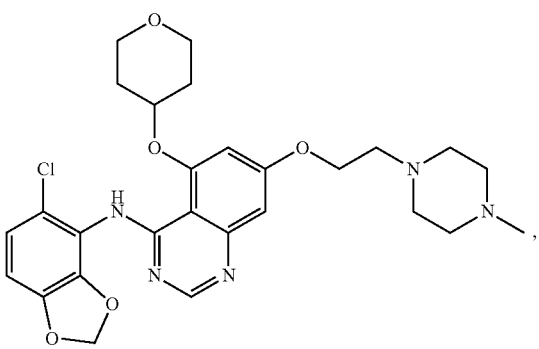 [SMILES: CN1CCN(CCOc2cc(OC3CCOCC3)c3c(Nc4c(Cl)ccc5c4OCO5)ncnc3c2)CC1]

wherein the compound comprises a deuterium atom. In some embodiments, the compound comprises more than one deuterium atom, e.g., 2, 3, 4, 5, 6, 7, 8, 9, 10, 11, 12, 13, 14, 15, or more deuterium atoms. Some embodiments provide a compound and compositions comprising a compound having a structure according to

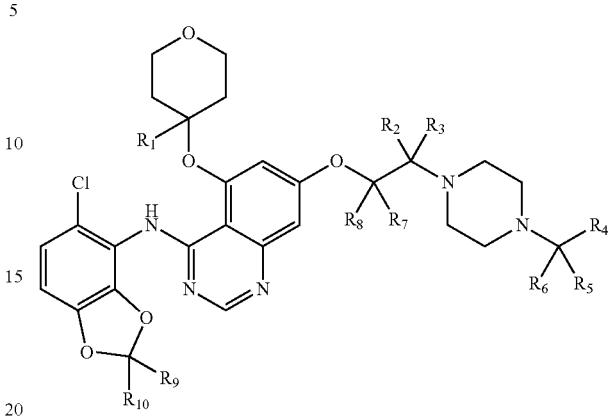

wherein one or more of $R_1$, $R_2$, $R_3$, $R_4$, $R_5$, $R_6$, $R_7$, $R_8$, $R_9$, and/or $R_{10}$ comprises a deuterium. In some embodiments, each of $R_2$, $R_3$, $R_7$, and $R_8$ comprises a deuterium; in some embodiments, each of $R_2$ and $R_3$ comprises a deuterium; in some embodiments, each of $R_9$ and $R_{10}$ comprises a deuterium; in some embodiments, each of $R_4$, $R_5$, and $R_6$ comprises a deuterium; in some embodiments, each of $R_7$ and $R_8$ comprises a deuterium; in some embodiments, each of $R_2$, $R_3$, $R_7$, $R_8$, $R_9$, and $R_{10}$ comprises a deuterium; in some embodiments, $R_1$ comprises a deuterium; in some embodiments, each of $R_4$, $R_5$, $R_6$, $R_9$, and $R_{10}$ comprises a deuterium; in some embodiments, each of $R_1$, $R_9$, and $R_{10}$ comprises a deuterium; in some embodiments, each of $R_1$, $R_2$, $R_3$, $R_4$, $R_5$, $R_6$, $R_7$, $R_8$, $R_9$, and $R_{10}$ comprises a deuterium; in some embodiments, each of $R_1$, $R_4$, $R_5$, $R_6$, $R_9$, and $R_{10}$ comprises a deuterium; and, in some embodiments, each of $R_2$, $R_3$, $R_4$, $R_5$, $R_6$, $R_7$, $R_8$, $R_9$, and $R_{10}$ comprises a deuterium.

In some embodiments, one or more of $R_1$, $R_2$, $R_3$, $R_4$, $R_5$, $R_6$, $R_7$, $R_8$, $R_9$, and/or $R_{10}$ is or consists of a deuterium. In some embodiments, each of $R_2$, $R_3$, $R_7$, and $R_8$ is or consists of a deuterium; in some embodiments, each of $R_2$ and $R_3$ is or consists of a deuterium; in some embodiments, each of $R_9$ and $R_{10}$ is or consists of a deuterium; in some embodiments, each of $R_4$, $R_5$, and $R_6$ is or consists of a deuterium; in some embodiments, each of $R_7$ and $R_8$ is or consists of a deuterium; in some embodiments, each of $R_2$, $R_3$, $R_7$, $R_8$, $R_9$, and $R_{10}$ is or consists of a deuterium; in some embodiments, $R_1$ is or consists of a deuterium; in some embodiments, each of $R_4$, $R_5$, $R_6$, $R_9$, and $R_{10}$ is or consists of a deuterium; in some embodiments, each of $R_1$, $R_9$, and $R_{10}$ is or consists of a deuterium; in some embodiments, each of $R_1$, $R_2$, $R_3$, $R_4$, $R_5$, $R_6$, $R_7$, $R_8$, $R_9$, and $R_{10}$ is or consists of a deuterium; in some embodiments, each of $R_1$, $R_4$, $R_5$, $R_6$, $R_9$, and $R_{10}$ is or consists of a deuterium; and, in some embodiments, each of $R_2$, $R_3$, $R_4$, $R_5$, $R_6$, $R_7$, $R_8$, $R_9$, and $R_{10}$ is or consists of a deuterium.

Related embodiments provide methods, systems, uses, and kits related to the above compounds. For example, embodiments provide a method of treating TNFα-related cytotoxicity in a subject by administering a deuterated compound having a structure according to

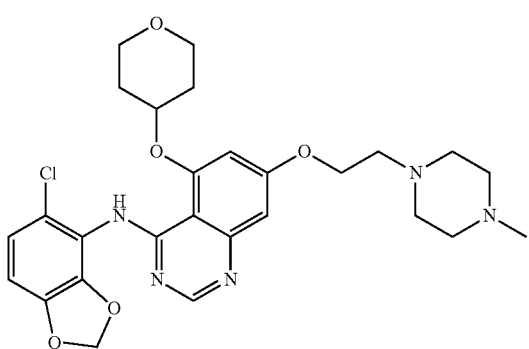 [SMILES: CN1CCN(CCOc2cc(OC3CCOCC3)c3c(Nc4c(Cl)ccc5c4OCO5)ncnc3c2)CC1]

to the subject.

For example, in some embodiments, the methods comprise administering to the subject a compound having a structure according to

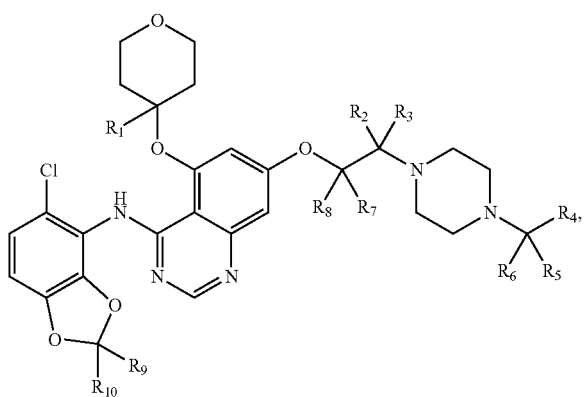

wherein one or more of $R_1$, $R_2$, $R_3$, $R_4$, $R_5$, $R_6$, $R_7$, $R_8$, $R_9$, or $R_{10}$ comprises a deuterium; each of $R_2$, $R_3$, $R_7$, and $R_8$ comprises a deuterium; each of $R_2$ and $R_3$ comprises a deuterium; each of $R_9$ and $R_{10}$ comprises a deuterium; each of $R_4$, $R_5$, and $R_6$ comprises a deuterium; each of $R_7$ and $R_8$ comprises a deuterium; each of $R_2$, $R_3$, $R_7$, $R_8$, $R_9$, and $R_{10}$ comprises a deuterium; $R_1$ comprises a deuterium; each of $R_4$, $R_5$, $R_6$, $R_9$, and $R_{10}$ comprises a deuterium; each of $R_1$, $R_9$, and $R_{10}$ comprises a deuterium; each of $R_1$, $R_2$, $R_3$, $R_4$, $R_5$, $R_6$, $R_7$, $R_8$, $R_9$, and $R_{10}$ comprises a deuterium; each of $R_1$, $R_4$, $R_5$, $R_6$, $R_9$, and $R_{10}$ comprises a deuterium; or each of $R_2$, $R_3$, $R_4$, $R_5$, $R_6$, $R_7$, $R_8$, $R_9$, and $R_{10}$ comprises a deuterium.

The technology is not limited with respect to the subject who is treated for TNFα-related cytotoxicity. For instance, non-limiting examples of subjects treated for TNFα-related cytotoxicity according to the technology provided include, e.g., a subject having or who is at risk of having microbial infection; a subject having or who is at risk of having sepsis; a subject having or who is at risk of having an inflammatory or infectious disease; or a subject having or who is at risk of having apoptosis-related tissue or organ damage. In particular embodiments, the subject is a human.

Embodiments comprise testing a subject in addition to treating a subject. For example, subjects are tested in some embodiments to inform the therapy to administer (e.g., choice of drug, dosage amount, dosage schedule, and/or co-administered therapies. For example, in some embodiments methods comprise testing the subject for a microbial infection, sepsis, or apoptosis-related tissue or organ damage. Some embodiments comprise administering an inhibitor of Src more than 1 time (e.g., 2, 3, 4, 5, 6, 7, 8, 9, 10, 11, 12, 13, 14, 15, 16, 17, 18, or 20 times or more). Thus, in some embodiments methods comprise a second administering an inhibitor of Src to the subject. Administering the Src inhibitor and testing the subject can occur in any pattern. For example, in some embodiments the testing is before the administering. In some embodiments, the testing is after the administering.

Related embodiments of methods comprise methods of treating TNFα-related cytotoxicity in a subject by administering to the subject an inhibitor of depolymerization of actin, an inhibitor of BAD, or an inhibitor of BAD translocation to mitochondria. Additional related embodiments of methods comprise methods of treating TNFα-related cytotoxicity in a subject by administering to the subject an activator of polymerization of actin, an activator of BAD phosphorylation, an activator of BAD degradation, an activator of BAD/14-3-3 interaction.

Some embodiments of the technology provide a composition for treating TNFα-related cytotoxicity comprising an inhibitor of Src. For example, in some composition embodiments the inhibitor of Src is a small molecule inhibitor of Src. In some composition embodiments, the inhibitor of Src is a deuterated small molecule inhibitor of Src. In some composition embodiments, the inhibitor of Src is dasatinib or saracatinib. In some composition embodiments, the inhibitor of Src is a compound provided in Table 1 (e.g., ZG5126, ZG5127, ZG5128, ZG5129, ZG5130, ZG5131, ZG5132, ZG5133, ZG5134, ZG5146, ZG5147, or ZG5151).

In some embodiments, the technology provides a composition for treating TNFα-related cytotoxicity comprising an inhibitor of depolymerization of actin, an inhibitor of BAD, or an inhibitor of BAD translocation to mitochondria. In some embodiments, the technology provides a composition for treating TNFα-related cytotoxicity comprising an activator of polymerization of actin, an activator of BAD phosphorylation, an activator of BAD degradation, or an activator of BAD/14-3-3 interaction.

Some embodiments provide kits comprising compositions described herein. For example, in some embodiments, the technology provides a kit for treating TNFα-related cytotoxicity comprising an inhibitor of Src. Some kit embodiments for treating a subject having or at risk of having TNFα-related cytotoxicity comprise a Src inhibitor and a reagent for testing a subject for microbial infection, sepsis, or apoptosis-related tissue or organ damage.

Some embodiments provide a kit comprising a compound as described herein, e.g., having a structure above or as otherwise described herein. Some embodiments provide uses of a compound as described herein, e.g., having a structure above or as otherwise described herein. For example, in some embodiments the technology provides use of a compound as described herein, e.g., having a structure above or as otherwise described herein, to treat a subject having or at risk of having TNFα-related cytotoxicity. In some embodiments the technology provides use of a compound as described herein, e.g., having a structure above or as otherwise described herein, to manufacture a medicament for administration to a subject. In some embodiments the technology provides use of a compound as described herein, e.g., having a structure above or as otherwise described herein, to manufacture a medicament for administration to a subject to treat or prevent TNFα-related cytotoxicity in a subject.

Some embodiments provide a kit for treating a subject having or at risk of having TNFα-related cytotoxicity, the kit comprising a compound a compound as described herein, e.g., having a structure above or as otherwise described herein, and a reagent for testing a subject for microbial infection, sepsis, or apoptosis-related tissue or organ damage.

In some embodiments, the technology provides uses of a composition comprising a Src inhibitor to treat a subject having or at risk of having TNFα-related cytotoxicity. Some embodiments provide uses of a composition comprising a Src inhibitor to manufacture a medicament for administration to a subject. Still further embodiments provide uses of a composition comprising a Src inhibitor to treat or prevent TNFα-related cytotoxicity in a subject.

In some embodiments, compositions are pharmaceutical compositions. For example, some embodiments provide a pharmaceutical composition for treating TNFα-related cytotoxicity comprising an inhibitor of Src. Particular embodiments provide a pharmaceutical composition formulated for administration to a human. Some related kit embodiments comprise a pharmaceutical composition for treating TNFα-related cytotoxicity comprising an inhibitor of Src. In some embodiments, a kit comprises a pharmaceutical composition formulated for administration to a human.

Some embodiments provide a pharmaceutical composition comprising a compound as described herein, e.g., having a structure above or as otherwise described herein. In some embodiments, pharmaceutical compositions are formulated for administration to a human. Some embodiments of pharmaceutical compositions comprise, e.g., buffers, excipients, and other components as described herein and/or as known in the art.

System embodiments provide a system for treating a subject having or at risk of having TNFα-related cytotoxicity. In particular embodiments, systems comprise a Src inhibitor and a reagent for testing a subject for microbial infection, sepsis, or apoptosis-related tissue or organ damage.

For example, some embodiments provide a system for treating a subject having or at risk of having TNFα-related cytotoxicity, the system comprising a compound as described herein, e.g., having a structure above or as otherwise described herein, and a reagent for testing a subject for microbial infection, sepsis, or apoptosis-related tissue or organ damage.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
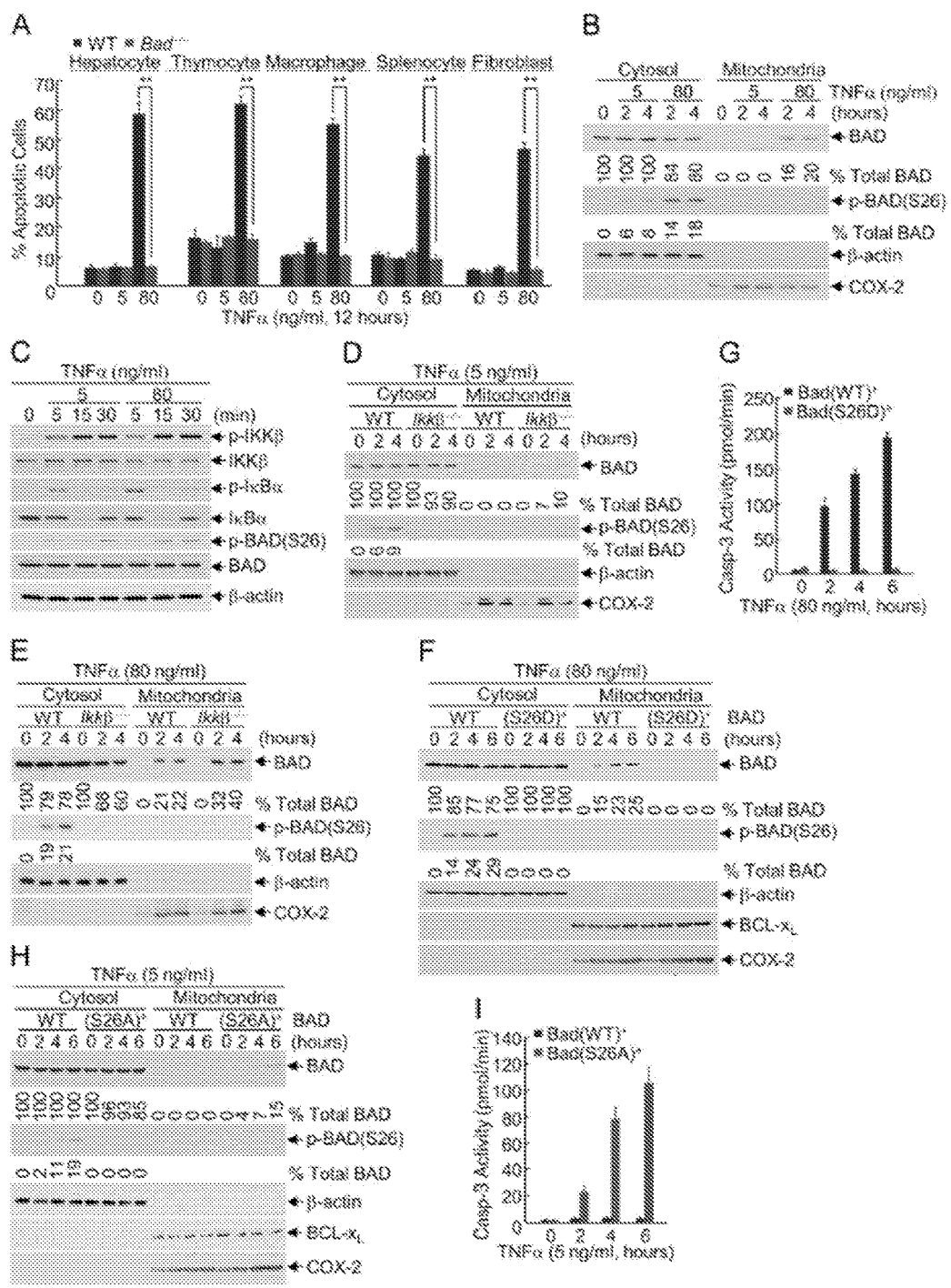
FIGS. 1A to 1I show that cytotoxic dose TNFα induces BAD-dependent apoptosis despite concurrent activation of IKK and NF-κB by overly mobilizing cytosolic BAD to exceed IKK phosphorylation capacity.

(1A) Various WT and Bad-deficient cells were treated with non-cytotoxic (5 ng/ml) or cytotoxic (80 ng/ml) dose TNFα for 12 hours and apoptotic cells were determined by Annexin V/propidium iodide (PI) staining and flow cytometric analysis. Data are means±s.d. **, P<0.01.

(1B and 1C) Cytotoxic but not non-cytotoxic dose TNFα induced BAD mitochondrial translocation (1B), as determined by cell fractionation and immunoblotting, but comparable activation of IKK and NF-κB (1C) in primary hepatocytes.

(1D and 1E) WT and Ikkβ-deficient fibroblasts were treated with non-cytotoxic (1D) or cytotoxic (1E) dose TNFα. BAD phosphorylation and mitochondrial translocation were determined as in (1B).

(1F to 1I) Bad-deficient fibroblasts ectopically expressing WT BAD, BAD(S26D) (1F and 1G), or BAD(S26A) mutant (1H and 1I), followed by treatment with or without cytotoxic dose (1F and 1G) or non-cytotoxic dose (1H and 1I) TNFα as indicated. BAD phosphorylation and mitochondrial translocation (1F and 1H), and apoptotic cells (1G and 1I) were determined as in (1A and 1B).

In FIGS. 1B, 1D, 1E, 1F, and 1H, the levels of BAD and the percentage of IKK-phosphorylated BAD in total BAD were determined and quantified. All results represent two to three individual experiments with similar results.

FIGS. 2A to 2J show that cytotoxic dose TNFα induces massive actin stress fiber depolymerization through Src-p190GAP-mediated inactivation of RhoA to release substantial BAD from cytoskeleton to cytosol.

(2A) Direct interaction between BAD and F-actin in actin stress fibers at cytoskeleton detected by super-resolution (ground state depletion) microscopy.

(2B and 2C) Cytotoxic dose TNFα significantly reduced BAD interaction with F-actin, as revealed by proximity ligation assay (2B), to release BAD to cytosol, as determined by cell fractionation (2C).

(2D) Cytotoxic dose TNFα induced massive actin stress fiber depolymerization, as detected by double immunofluorescence staining. Scale bars represent 5 μm (2B and 2D).

(2E) Cytotoxic dose TNFα induced stronger and sustained early-phase inactivation and delayed activation of RhoA, as measured by the G-LISA RhoA activation assay. Data are means±s.d.

(2F to 2H) Cytotoxic dose TNFα induced stronger activation of Src and p190GAP (2F), while knockdown of Src (2G) or p190GAP (2H) blocked cytotoxic dose TNFα-induced BAD mitochondrial translocation.

(2I and 2J) Ectopically expressed RhoA(Q63L) mutant but not WT RhoA inhibited cytotoxic dose TNFα-induced BAD release from cytoskeleton (2I) and mitochondrial translocation (2J).

In FIGS. 2C, 2G, 2H, 2I, and 2J, the levels of BAD and IKK-phosphorylated BAD were determined and quantified. All results represent two to three individual experiments with similar results.

FIGS. 3A to 3I show that BAD-mediated TNFα cytotoxicity promotes polymicrobial infection-induced tissue damage and mortality in severe sepsis.

(3A, 3B, 3D, 3G, and 3H) WT littermate and Bad-deficient mice were subjected to cecal ligation and puncture (CLP) surgery or Sham procedure and the mortality rate was determined (3A). Liver and colon damage and hepatocyte and epithelial cell apoptosis were analyzed by haematoxylin and eosin (H&E) staining and TUNEL staining, respectively (3B). Serum ALT, AST, BUN, and LDH were determined (3D). Bacteria load in the circulation or tissues as indicated were analyzed by blood culture and Gram staining (3G). Expressions of TNFα, IL-16, IL-6, IL-10 and IFNγ in liver and colon were quantified by real-time PCR (3H).

(3C) Intravenously injected Ad/Bad but not Ad/Ctrl (LacZ) in Bad-deficient mice re-sensitized the mice to CLP surgery-induced mortality.

(E and F) Tnf-R1-deficient but not WT littermate mice were protected against CLP-induced mortality (E) and liver and colon damage (F). (I) WT littermate and Bad-deficient mice were intraperitoneally (i.p.) injected with lethal *E. coli* ($3\times10^7$) and the mortality rate was determined.

In 3A, 3C, 3E, and 3I, the statistical significance was analyzed by log rank (Mantel-Cox) test. In 3D, 3G, and 3H, data are means±s.d. and represent three individual experiments.

Figure 4:
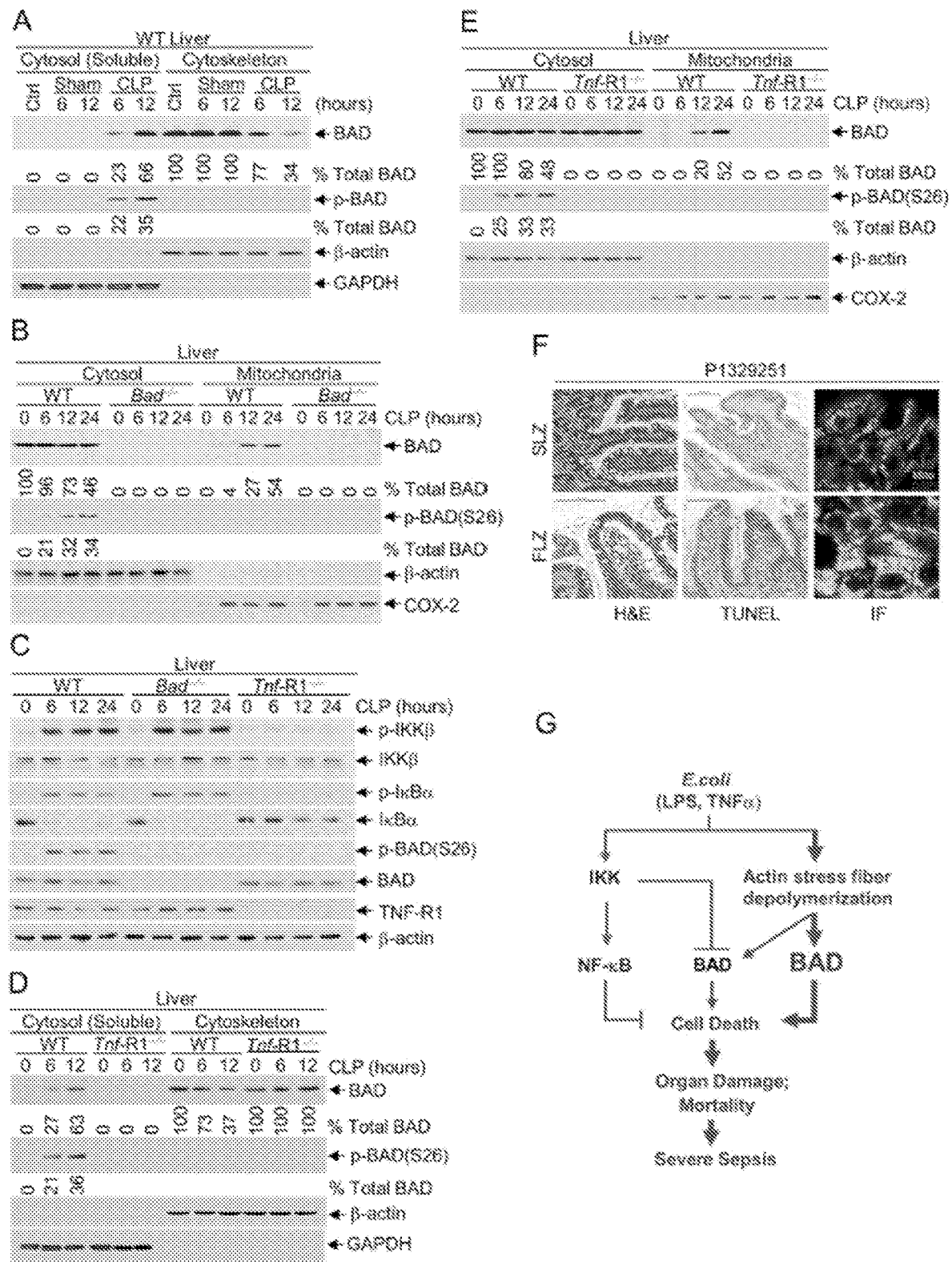
Figure 5:
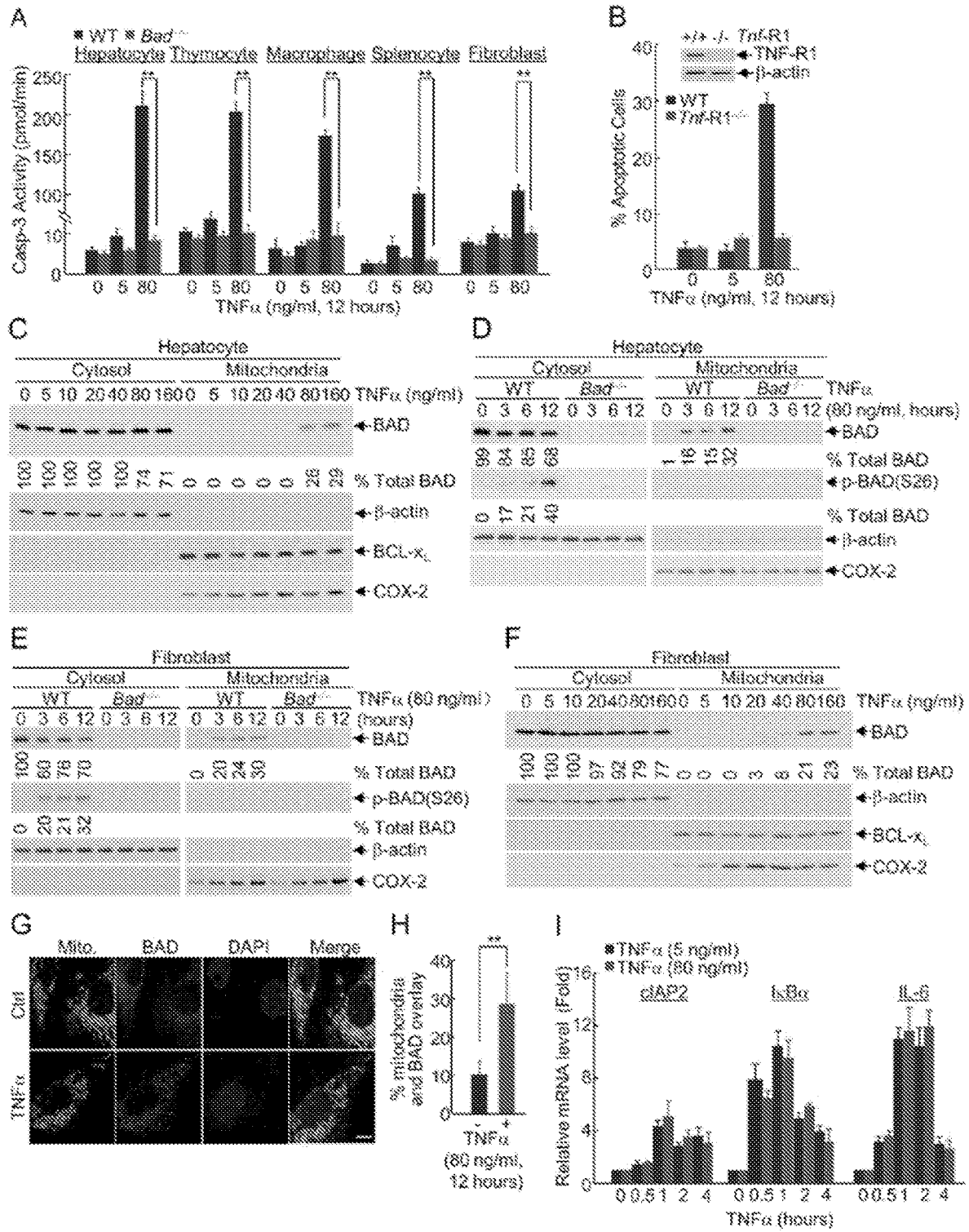

FIGS. 4A to 4F show that polymicrobial infection utilizes the same mechanism as cytotoxic dose TNFα to stimulate BAD pro-apoptotic activity in severe sepsis and FIG. 4F provides a model for sepsis.

(A to E) WT littermate, Bad-deficient or TnfR1-deficient mice were subjected to CLP surgery or Sham procedure. Total liver tissue extracts were fractionated to determine BAD release from cytoskeleton to cytosol (A and D) or translocation from cytosol to mitochondria (B and E). The levels of BAD and the percentage of IKK-phosphorylated BAD in total BAD were determined and quantified. The results represent three individual experiments with similar results. Polymicrobial infection induced comparable activation of IKK and NF-κB in WT littermate, Bad-deficient and Tnf-R1-deficient mice livers (C).

(F) The colon damage and epithelial cell apoptosis of colon tissue specimens of patients having perforation of ulcerative colitis accompanying with severe sepsis were analyzed by H&E staining and TUNEL staining, respectively. Mitochondria were detected by anti-Tom 20 antibody and nuclei by DAPI. SLZ; side-lesion-zone; FLZ: focal-lesion-zone. Scale bars represent 5 μm.

(G) A schematic presentation of the mechanism by which polymicrobial infection via TNFα stimulates BAD pro-apoptotic activity despite concurrent activation of IKK, resulting in multi-organ damage and mortality.

FIGS. 5A to 5I show that high dose TNFα is cytotoxic and is sufficient to induce apoptosis in a BAD-dependent manner.

FIGS. 6A to 6E show that cytotoxic and non-cytotoxic dose TNFα utilize different mechanisms to induce apoptosis.

Figure 7:
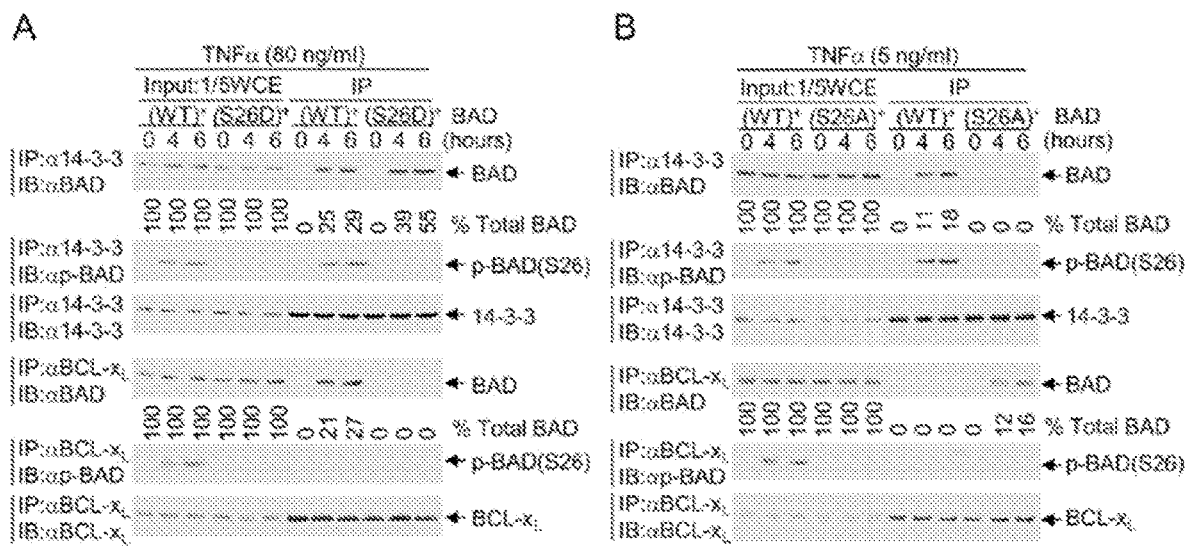
Figure 8:
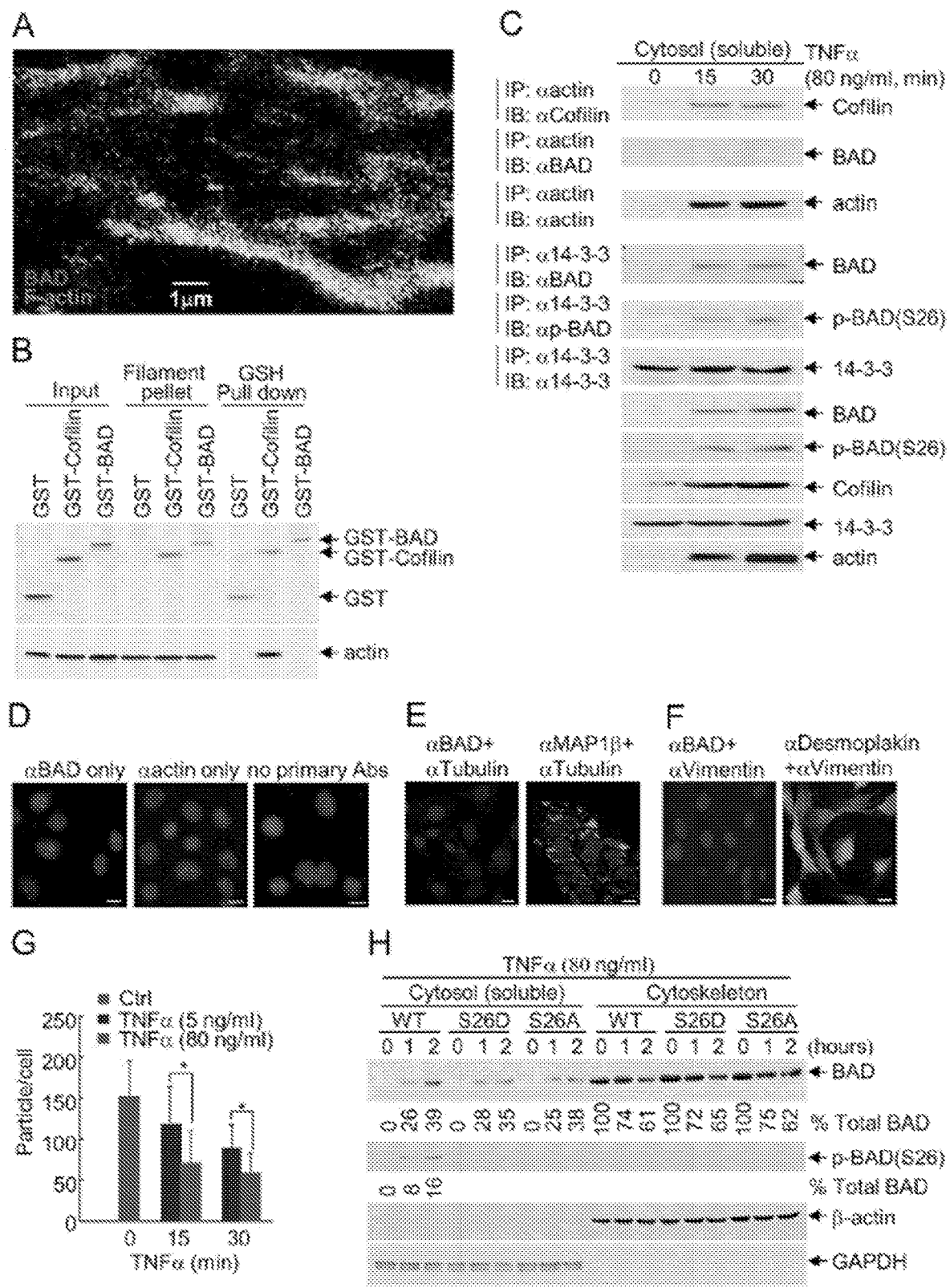

FIGS. 7A and 7B show that BAD(S26D) and BAD(S26A) mutants act as phosphor-mimetic and constitutively non-phosphorylated mutants, respectively.

FIGS. 8A to 8H show that BAD is sequestered at cyto-skeleton through selective interaction with F-actin in actin stress fibers and released to cytosol by cytotoxic dose TNFα independently of its phosphorylation status.

Figure 9:
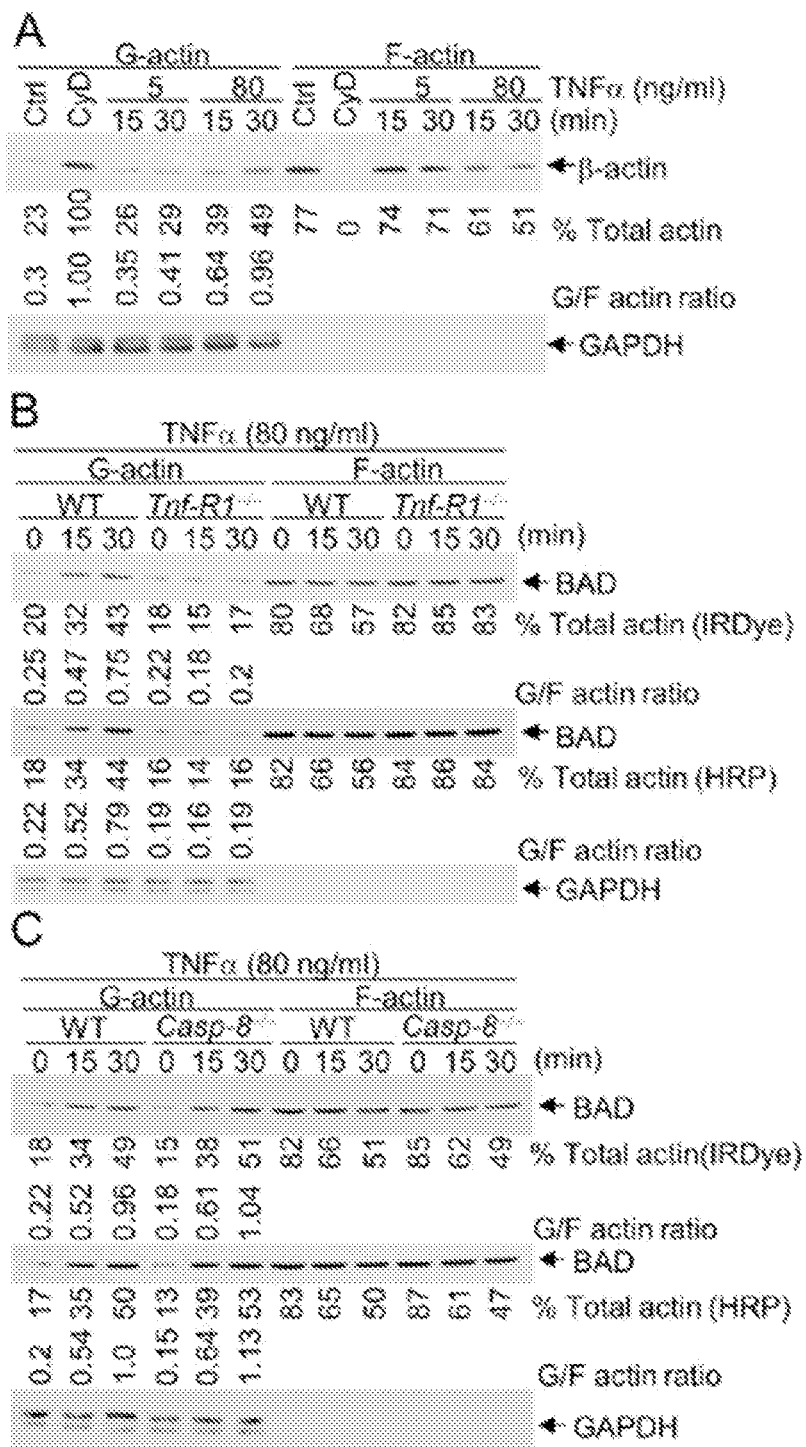
Figure 10:
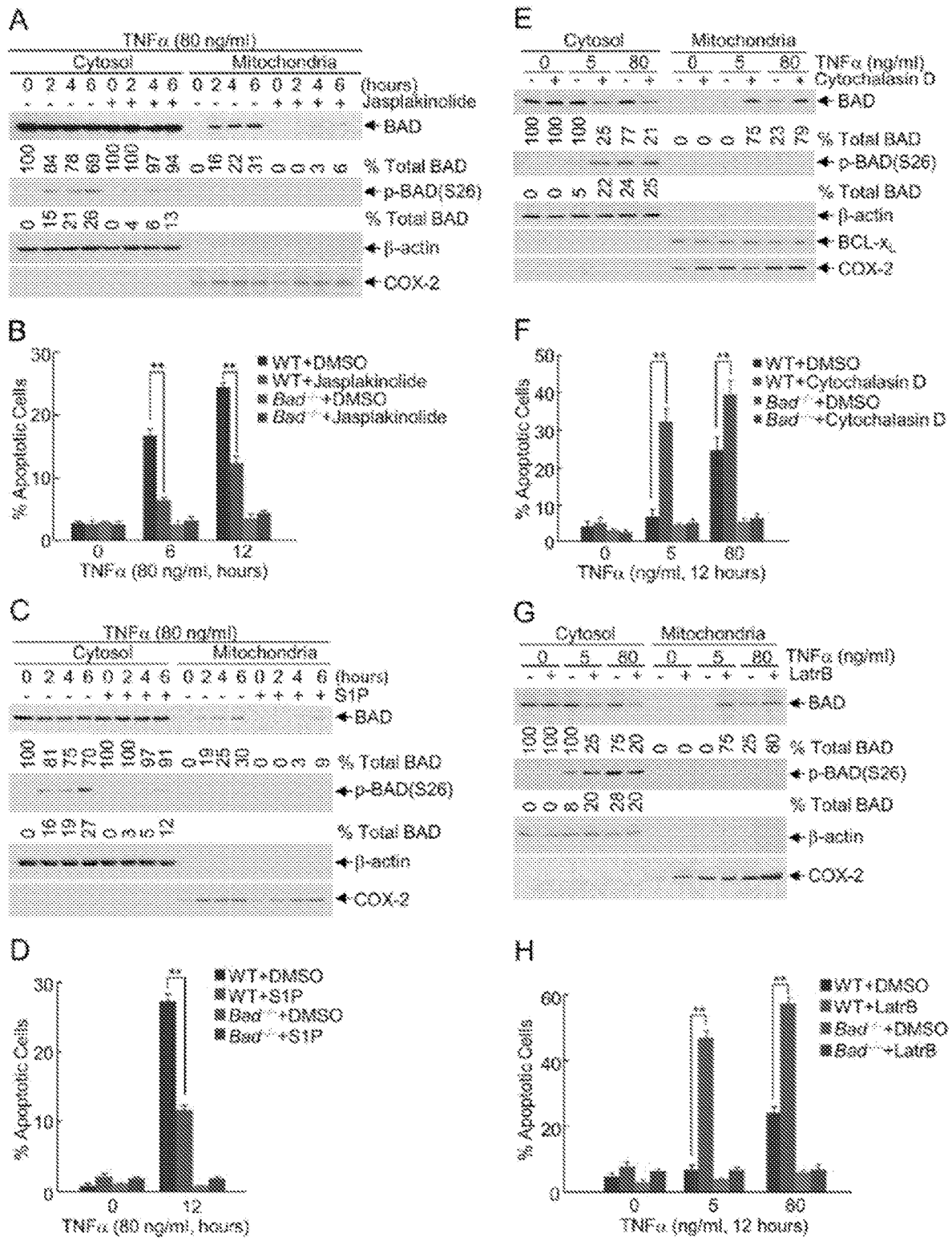

FIGS. 9A to 9C show that cytotoxic dose TNFα-induced depolymerization of actin stress fibers depends on TNF-$R_1$ but not Casp-8.

FIGS. 10A to 10H show that TNFα-associated induction of BAD mitochondrial translocation and apoptosis is inhibited by polymerization but promoted by depolymerization of actin stress fibers.

FIGS. 11A to 11G show that cytotoxic dose TNFα selectively induces an early-phase inactivation of RhoA and subsequent depolymerization of actin stress fibers by preferentially activating the Src-p190GAP pathway.

FIGS. 12A to 12G show that Bad-deficient mice were protected against *E. coli* infusion-induced organ damage and mortality.

FIGS. 13A to 13E show that Bad-deficient mice were protected against LPS-induced organ damage and mortality.

FIGS. 14A to 14E show that *E. coli* and LPS utilize the same mechanism as cytotoxic dose TNFα to stimulate BAD pro-apoptotic activity.

Figure 15:
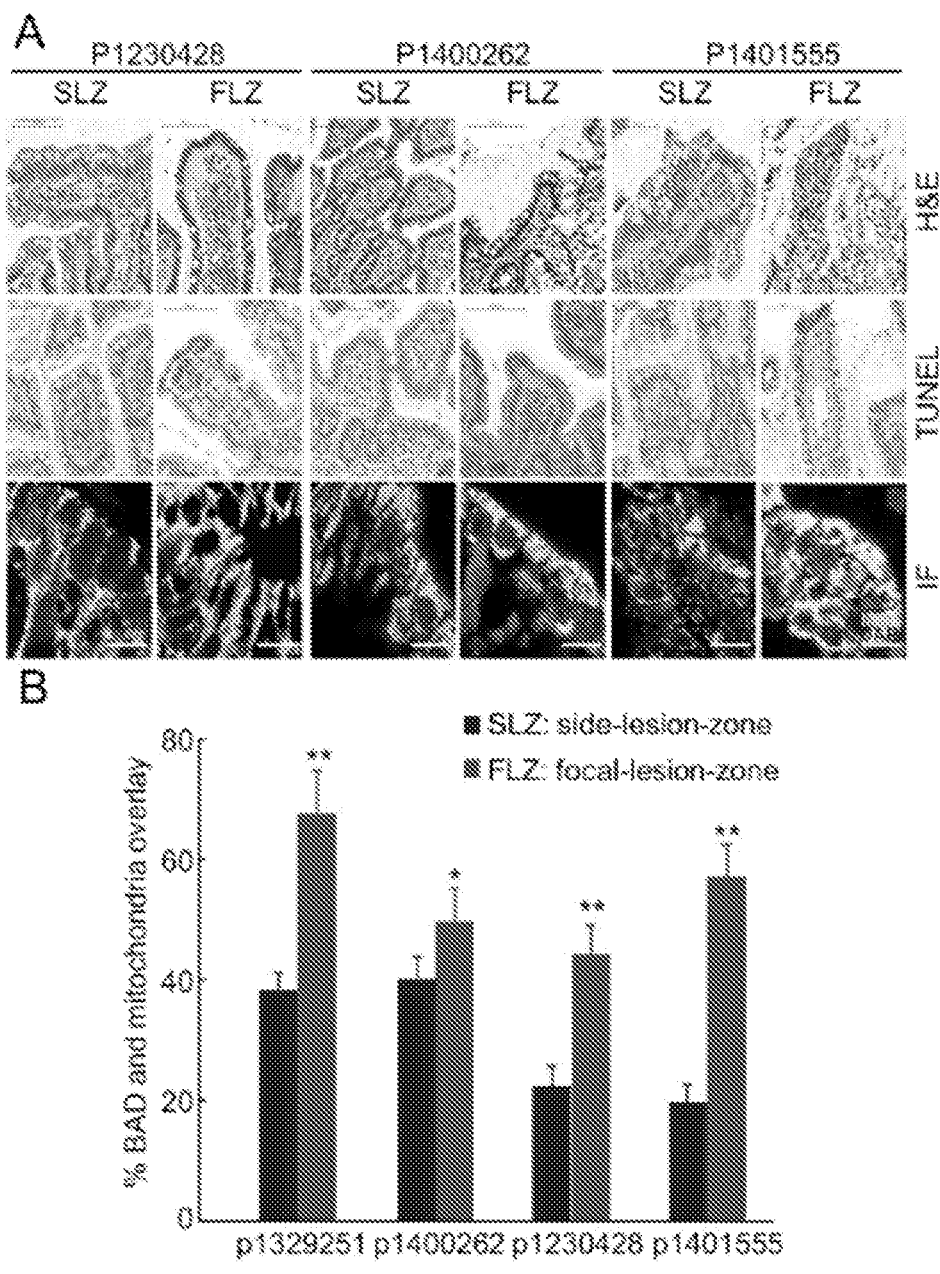

FIGS. 15A and 15B show that BAD mitochondrial translocation correlates with epithelium damage in human colon tissue specimens of severe sepsis patients.

Figure 16:
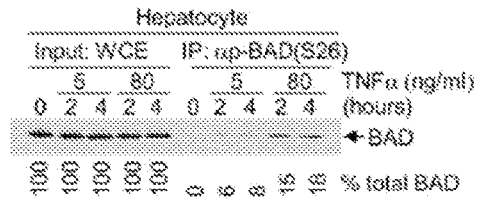
Figure 16:
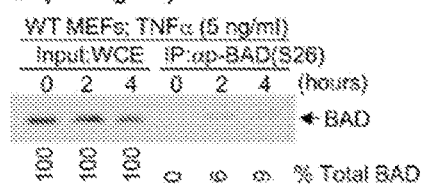
Figure 16:
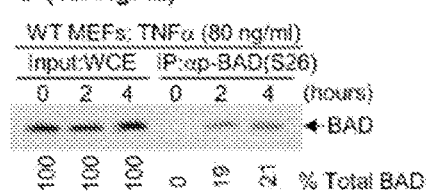
Figure 16:
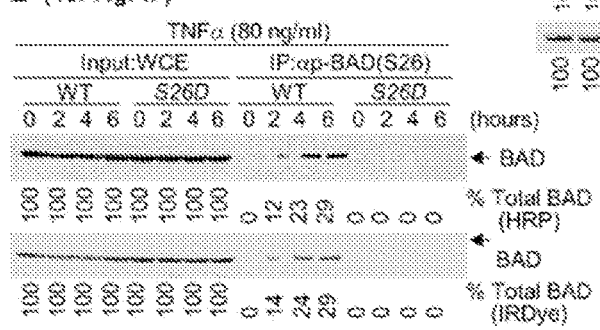
Figure 16:
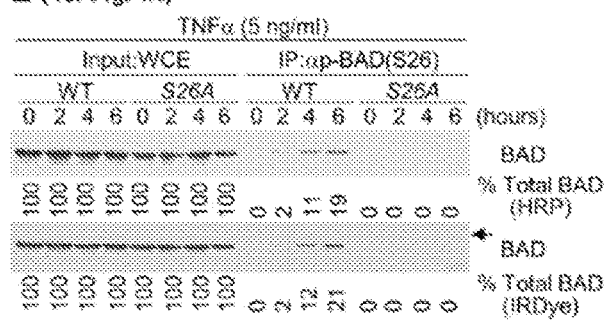
Figure 16:
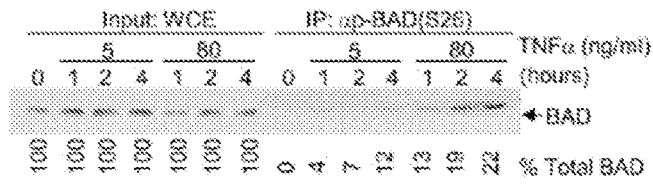
Figure 16:
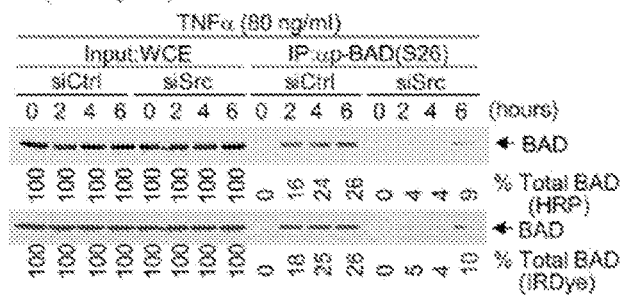
Figure 16:
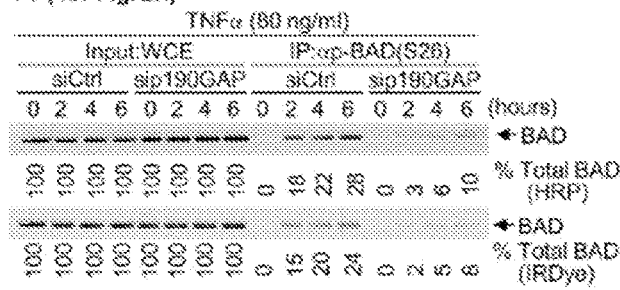
Figure 16:
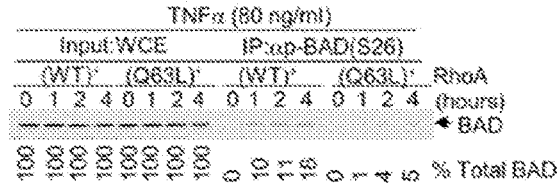
Figure 16:
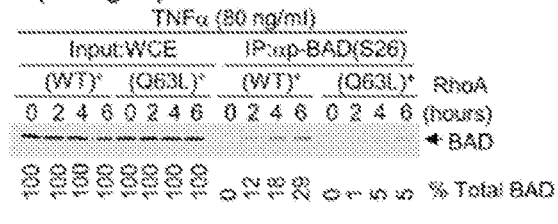
Figure 16:
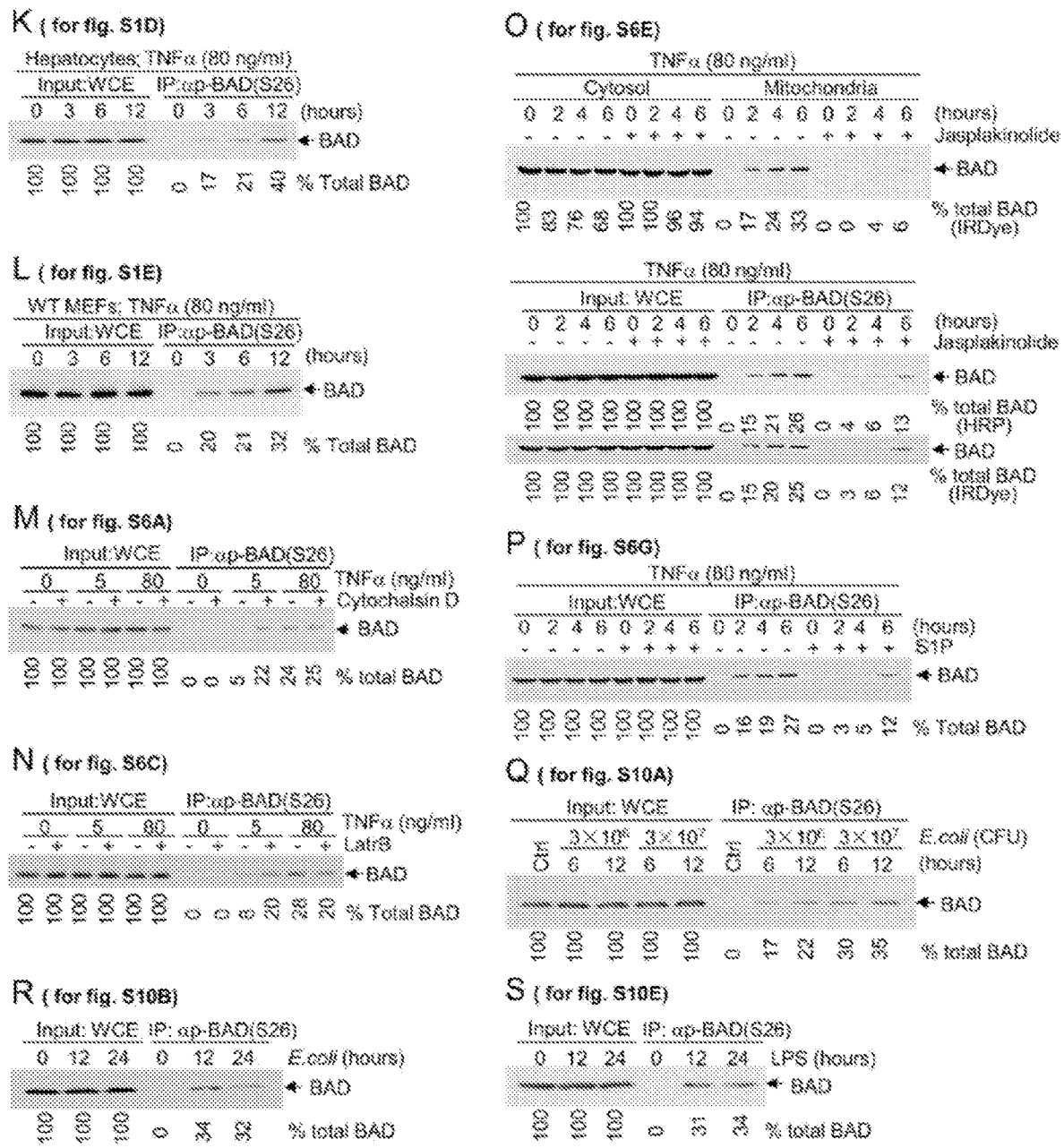
Figure 16:
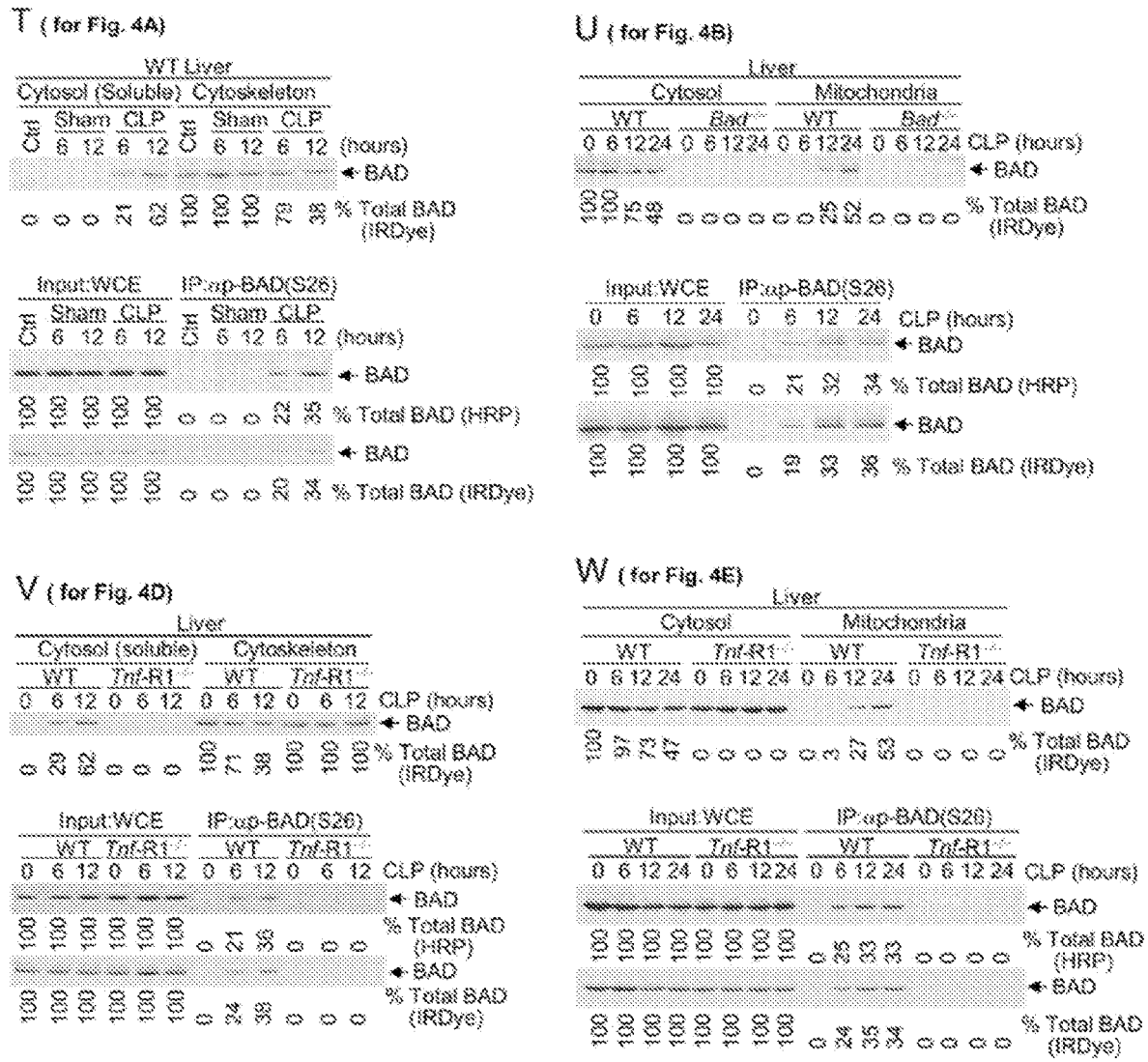

FIGS. 16A to 16W show quantification of phosphorylated BAD proteins in experiments shown in FIGS. 1, 2, 5, 10, and 14 as indicated in the figures.

Figure 17:
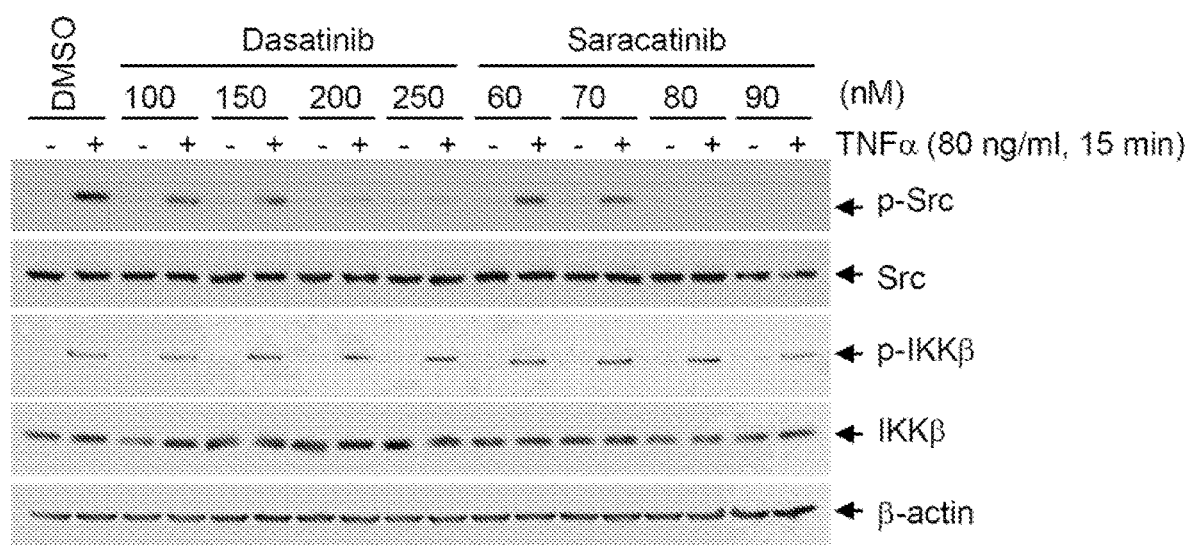

FIG. 17 shows an immunoblot indicating that both saracatinib and dasatinib inhibit Src phosphorylation but not IKK phosphorylation.

Figure 18:
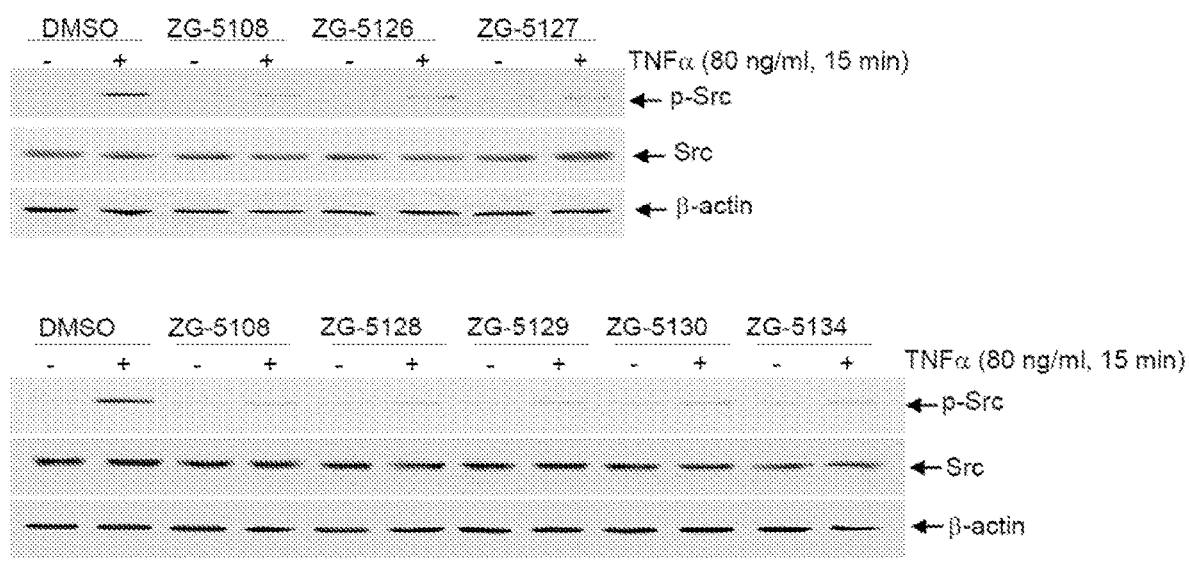

FIG. 18 shows immunoblots indicating that embodiments of small molecule Src inhibitors provided herein inhibit Src phosphorylation.

Figure 19A:
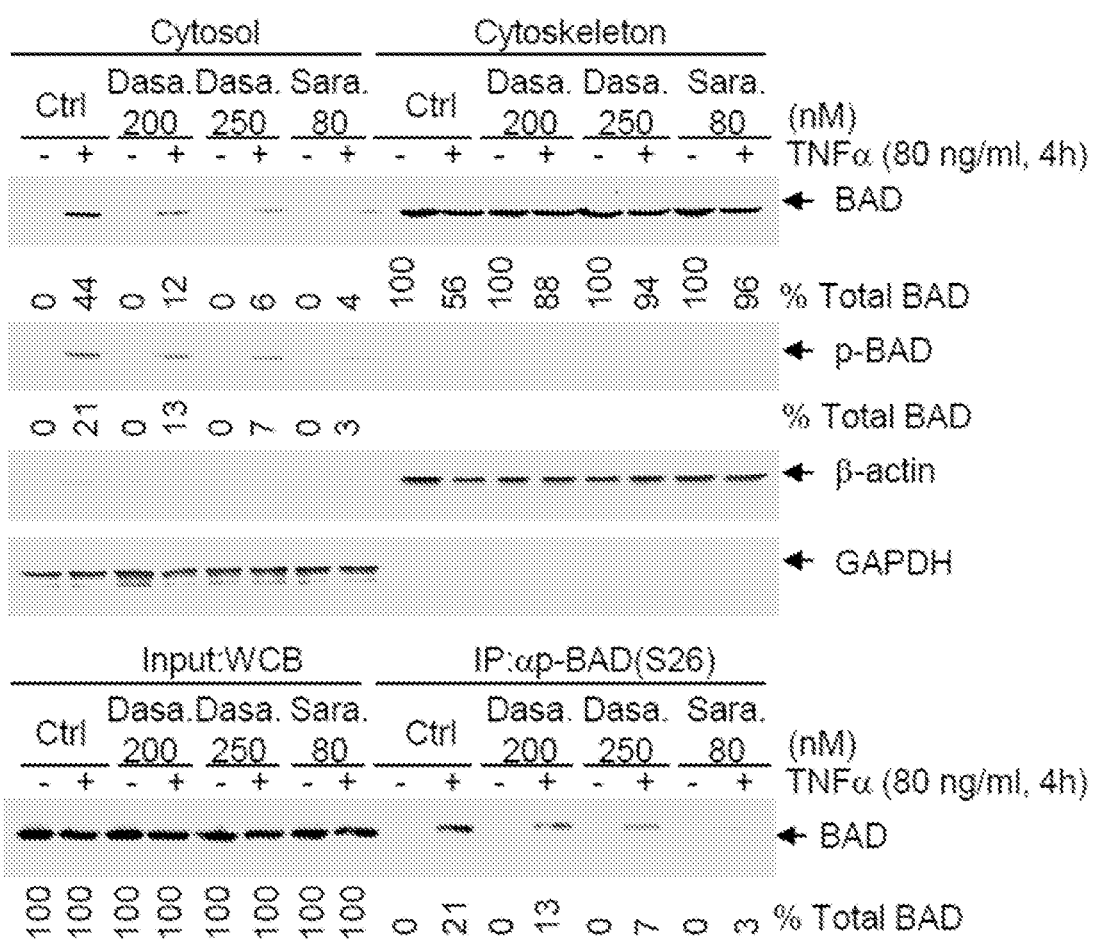

FIG. 19A shows immunoblots indicating that saracatinib and dasatinib inhibit cytotoxic dose TNFα-induced BAD release from cytoskeleton to cytosol.

Figure 19B:
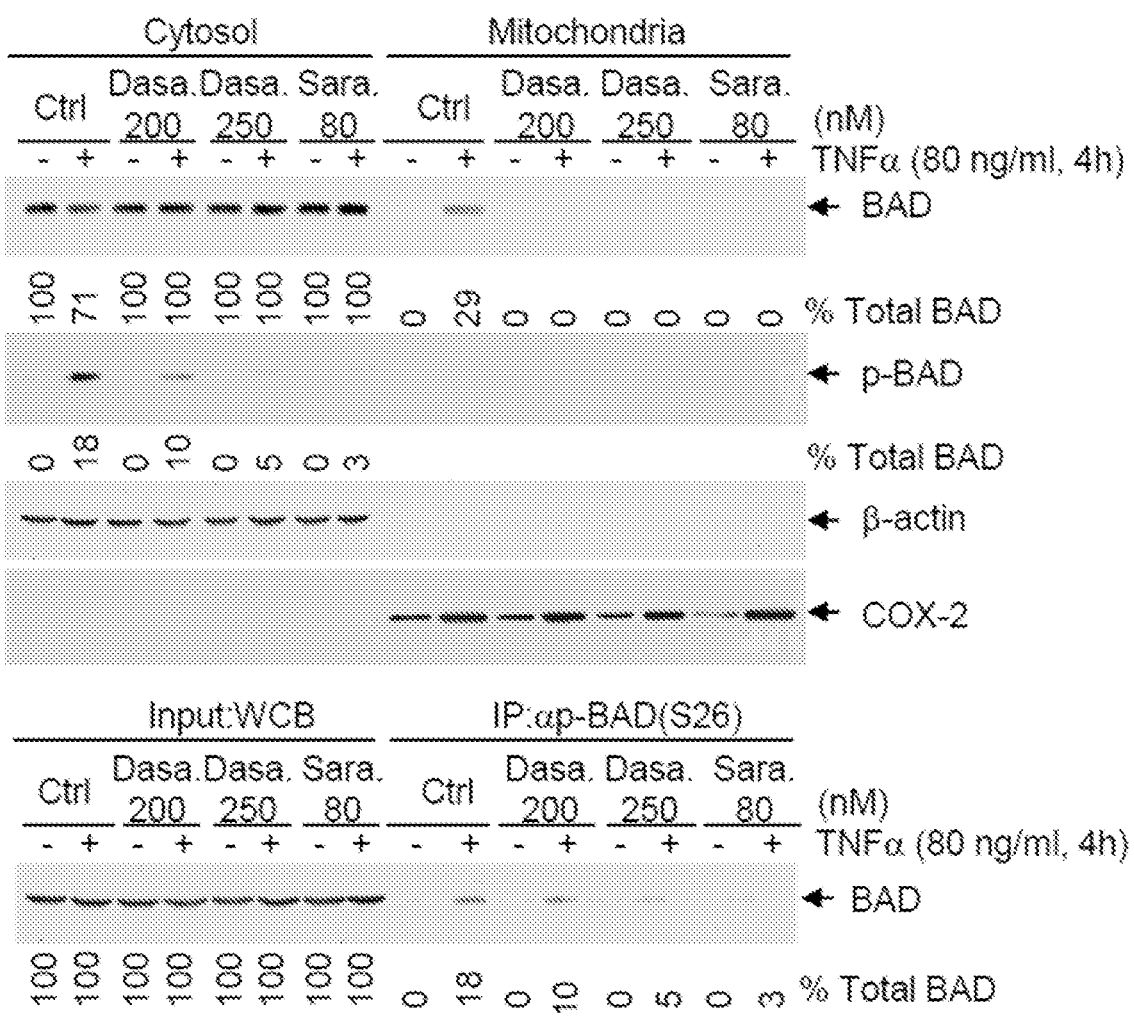

FIG. 19B shows immunoblots indicating that saracatinib and dasatinib inhibit cytotoxic dose TNFα-induced BAD translation to mitochondria.

Figure 20A:
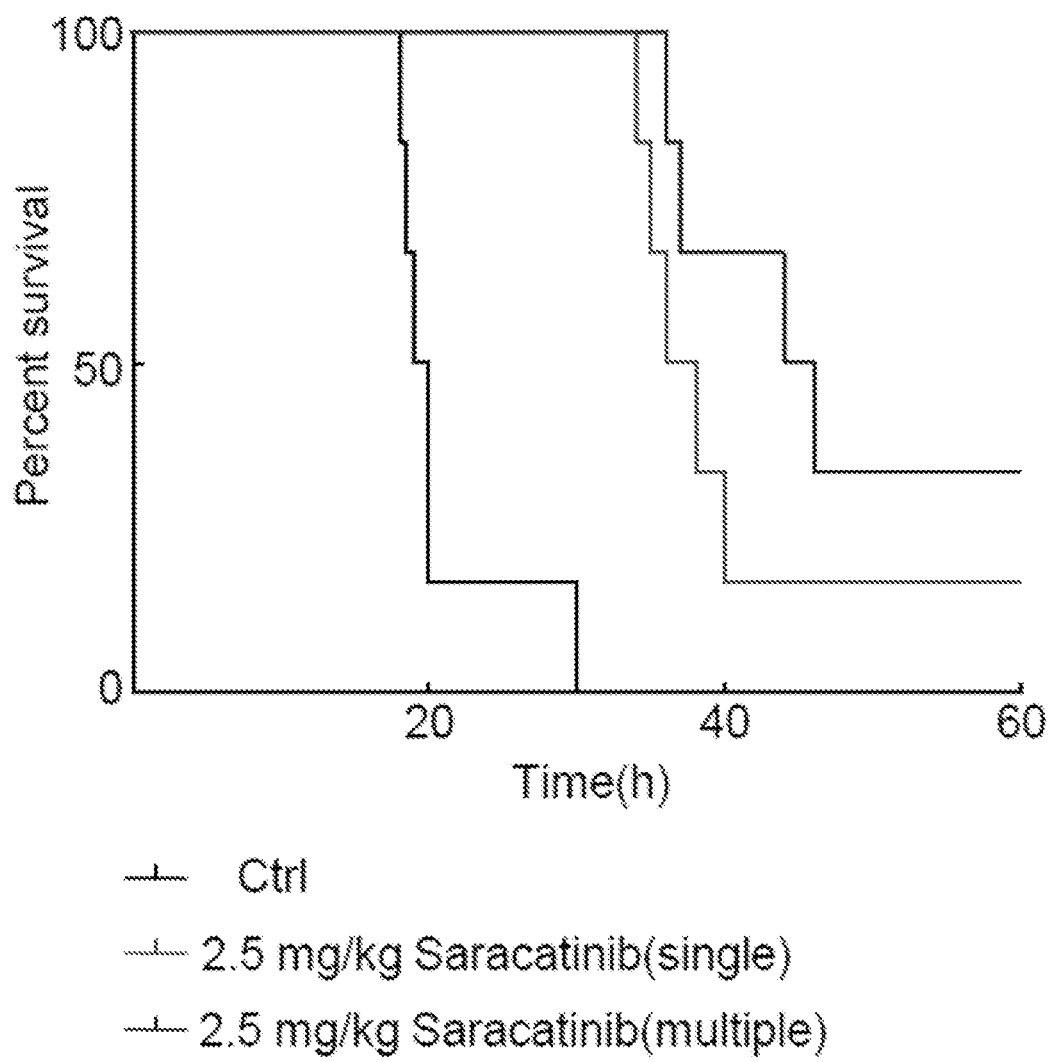

FIG. 20A shows a plot of mortality versus time for bacterially infected mice treated with embodiments of small molecule Src inhibitors.

Figure 20B:
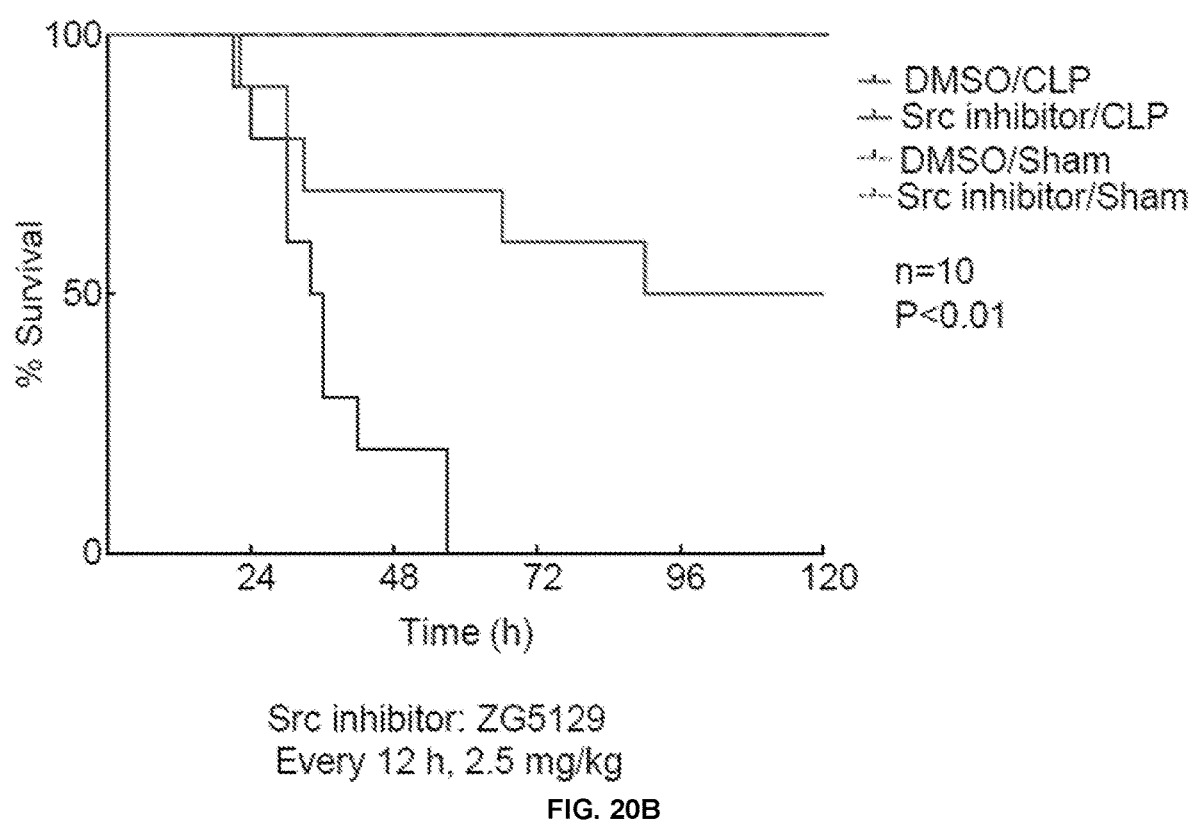

FIG. 20B shows a plot of mortality versus time for a mouse model of polymicrobial infection treated with embodiments of small molecule Src inhibitors.

Figure 21A:
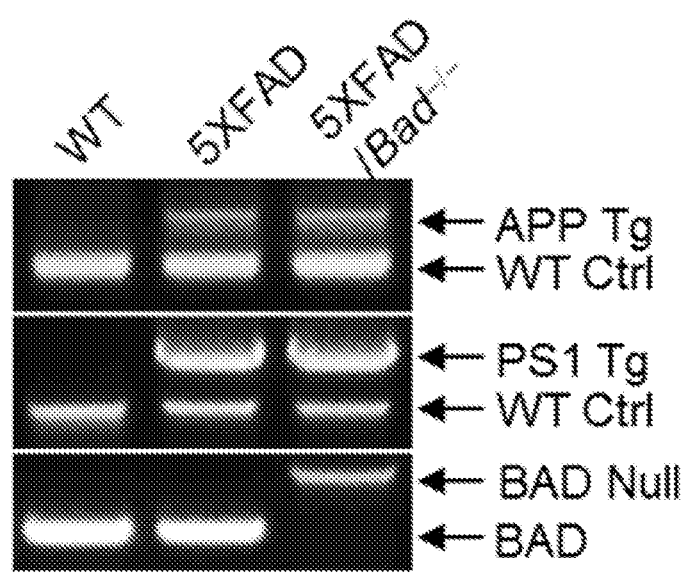

FIG. 21*a* is an image of an electrophoresis gel showing the results of genotyping WT, 5XFAD, and 5XFAD/Bad$^{-/-}$ mice. The data indicated that 5XFAD/Bad$^{-/-}$ mice have APP and PSI transgenes but do not have a copy of the Bad gene.

Figure 21B:
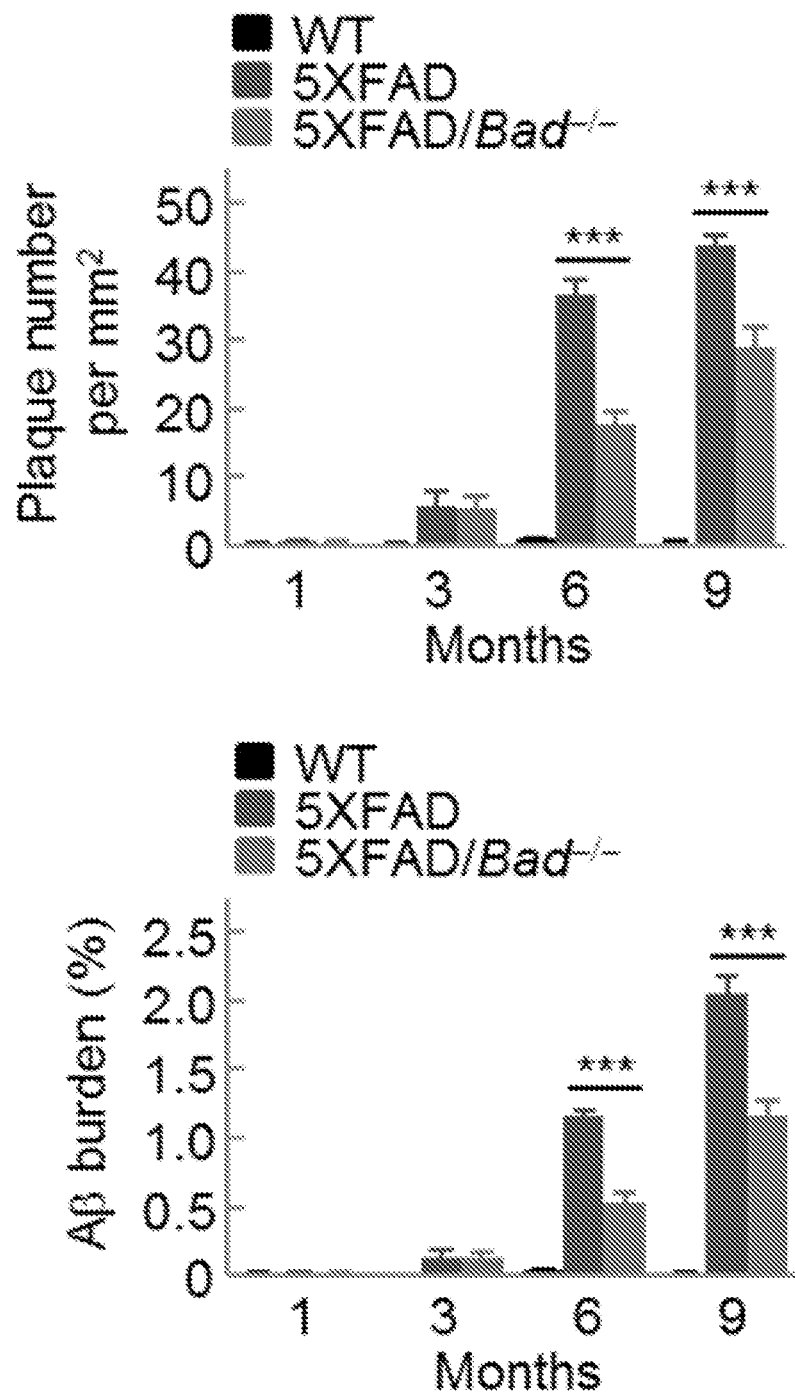

FIG. 21*b* is a bar plot showing quantification of the number and area fraction (%) of Aβ plaques in whole brain sections of WT, 5XFAD, and 5XFAD/Bad$^{-/-}$ mice (from left to right for each set of bars). AB plaques in whole brain sections of WT, 5XFAD, and 5XFAD/Bad$^{-/-}$ mice were detected by 6E10 antibody for a time course (n=5, mean±s.e.m., Student's t-test, ***P<0.001).

Figure 22A:
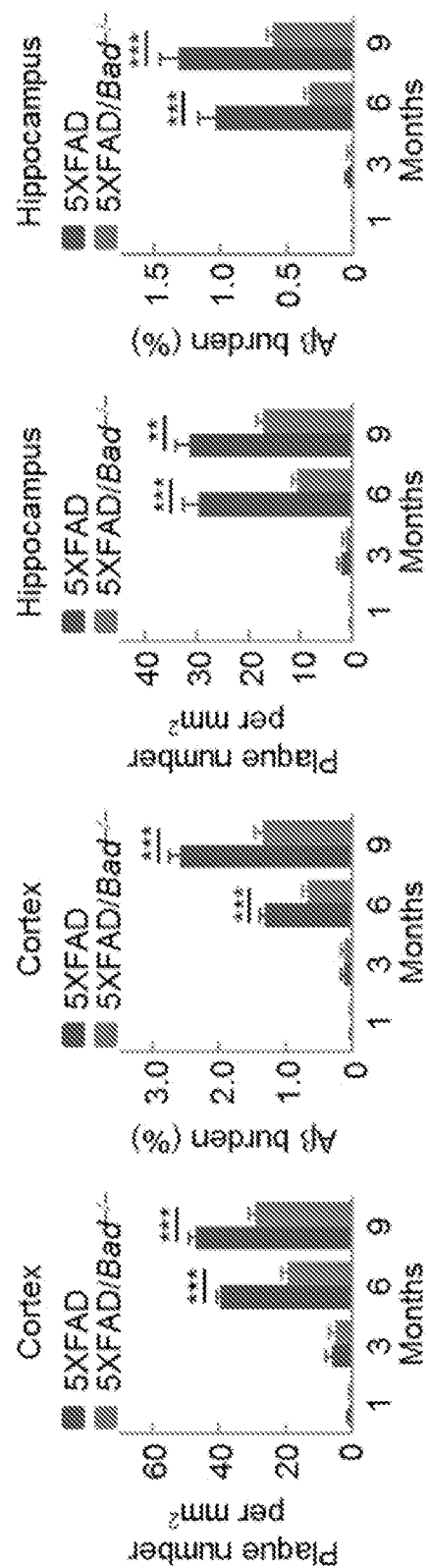

FIG. 22*a* is a bar plot showing quantification of the number and area fraction (%) of AB plaques in cortex and hippocampus (from left to right for each set of bars). AB plaques in cortex and hippocampus of 5XFAD and 5XFAD/Bad$^{-/-}$ mice were detected by staining with 6E10 antibody and imaging samples, which were subsequently quantified (n=5, mean±s.e.m., Student's t-test, P<0.01, *P<0.001).

Figure 22B:
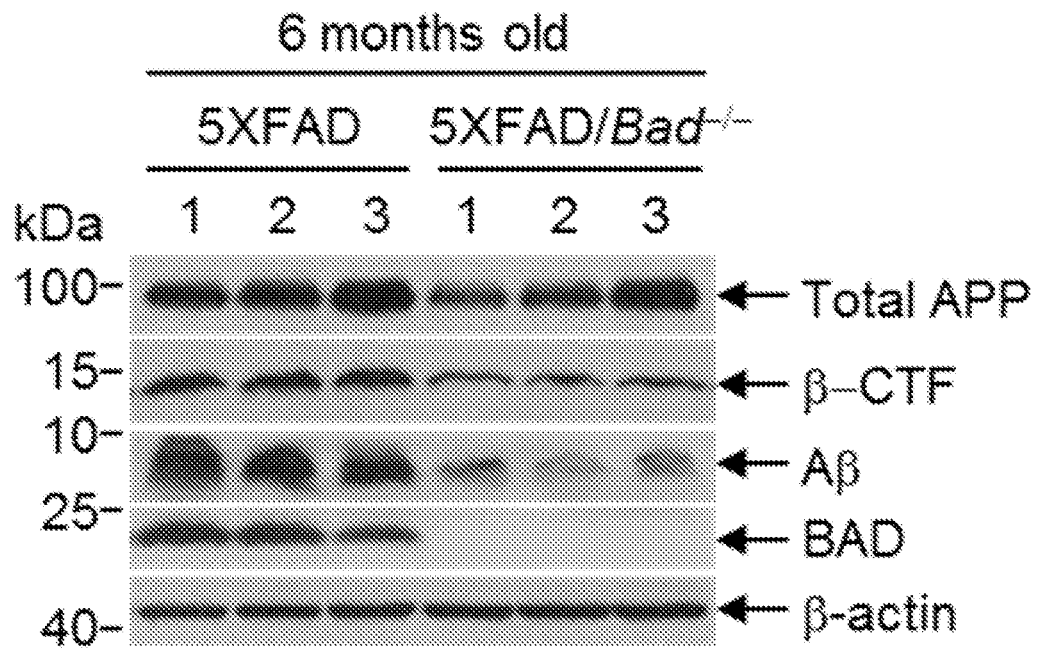

FIG. 22*b* shows a western blot analysis of the levels of total APP, ß-CTF, and total Aß in the brain homogenate of 6-month-old 5XFAD and 5XFAD/Bad$^{-/-}$ mice.

Figure 22C:
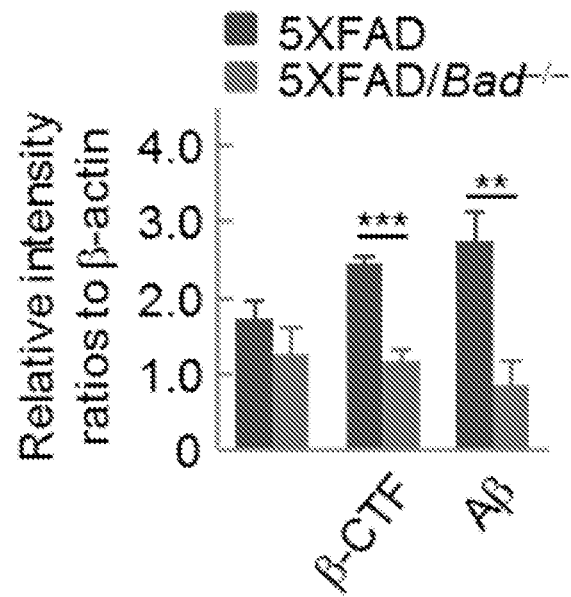

FIG. 22*c* shows the relative intensity quantification of APP, 6-CTF and Aß as ratios to ß-actin (n=3, mean±s.d., Student's t-test, P<0.01, *P<0.001).

Figure 22D:
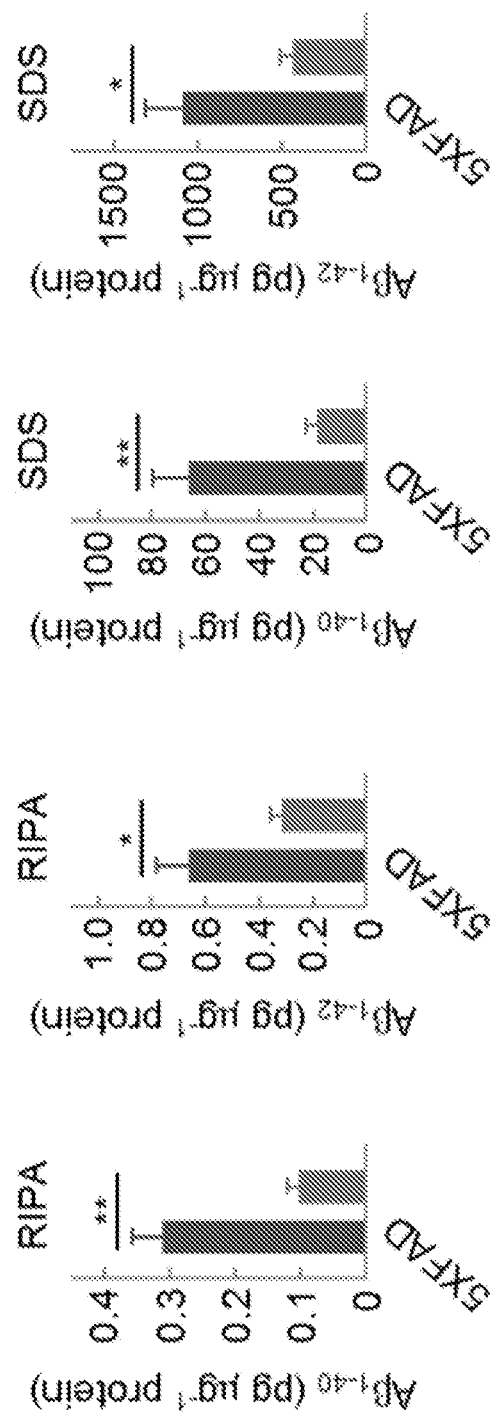

FIG. 22*d* shows soluble or insoluble Aß$_{1-40}$ and Aß$_{1-42}$ in RIPA or SDS brain extracts from 6-month-old 5XFAD and 5XFAD/Bad$^{-/-}$ mice as detected by ELISA (n=5, mean±s.e.m., Student's t-test, *P<0.05, **P<0.01).

Figure 23A:
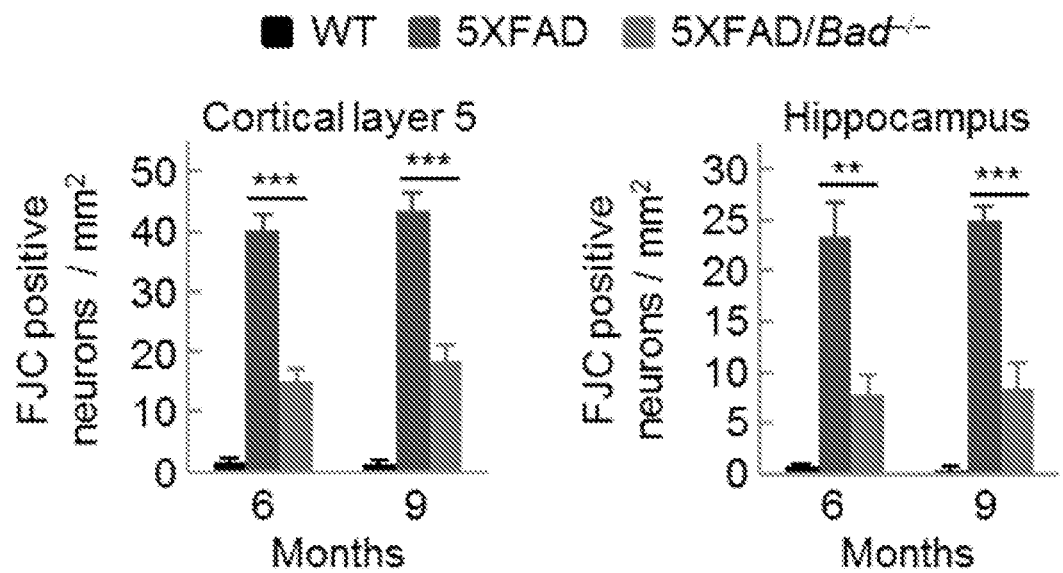

FIG. 23*a* shows quantification of FJC positive neuronal density in cortical layer 5 and hippocampus of 6- and 9-month-old WT, 5XFAD, and 5XFAD/Bad$^{-/-}$ mice (n=5, mean±s.e.m., Student's t-test, P<0.01, *P<0.001).

Figure 23B:
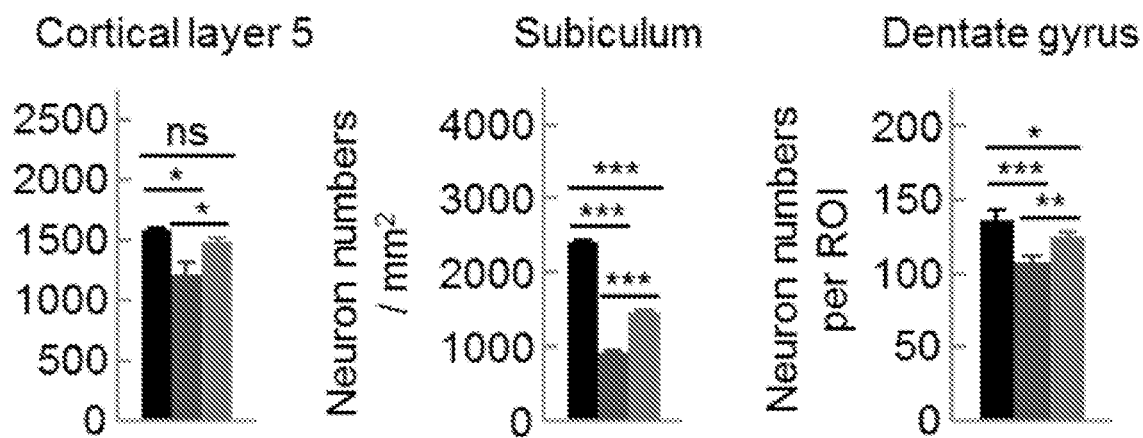

FIG. 23*b* shows quantification of neuronal density in cortical layer 5, subiculum, and dentate gyrus (n=5, mean±s.e.m., Student's t-test, *P<0.05, P<0.01, *P<0.001). Neuronal loss was analyzed in 9-month-old WT, 5XFAD, and 5XFAD/Bad$^{-/-}$ mice, neuronal density in cortical layer 5 of cortex and subiculum of hippocampus was analyzed by Nissl staining and neuronal loss in dentate gyrus of hippocampus was analyzed by immunofluorescence staining with NeuN antibody.

Figure 24A:
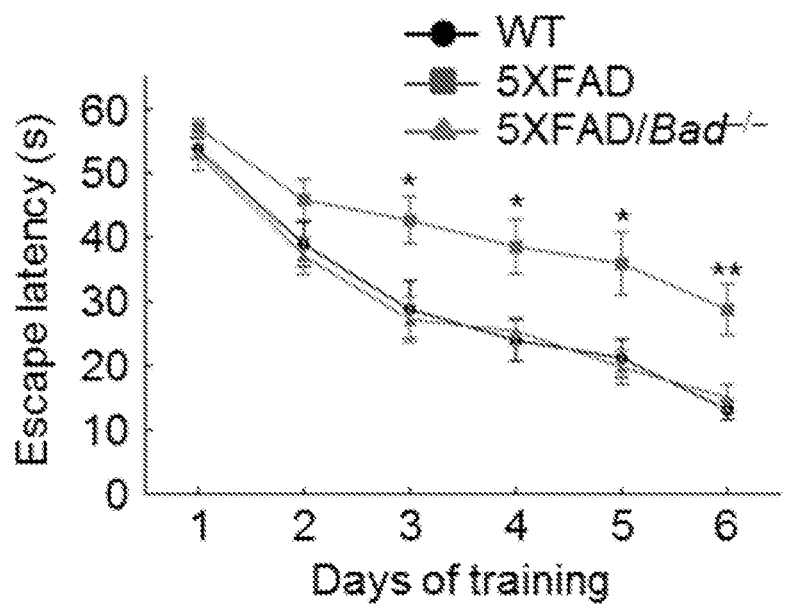

FIG. 24a shows results of the Morris water maze test of escape latency for 6-month-old WT (n=16), 5XFAD (n=14), and 5XFAD/Bad$^{-/-}$ (n=16) mice (mean±s.e.m., one-way ANOVA followed by Bonferroni's post-hoc test, *P<0.05, **P<0.01).

Figure 24B:
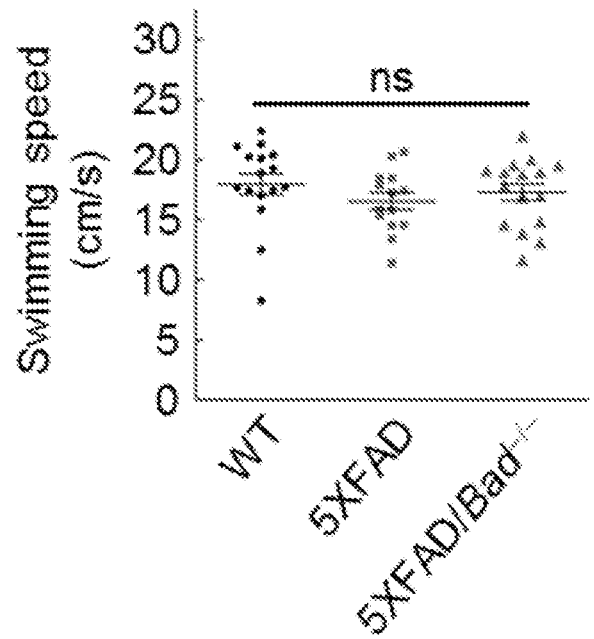

FIG. 24b shows swimming speeds of the first trial on day 1 (mean±s.e.m., one-way ANOVA).

Figure 24C:
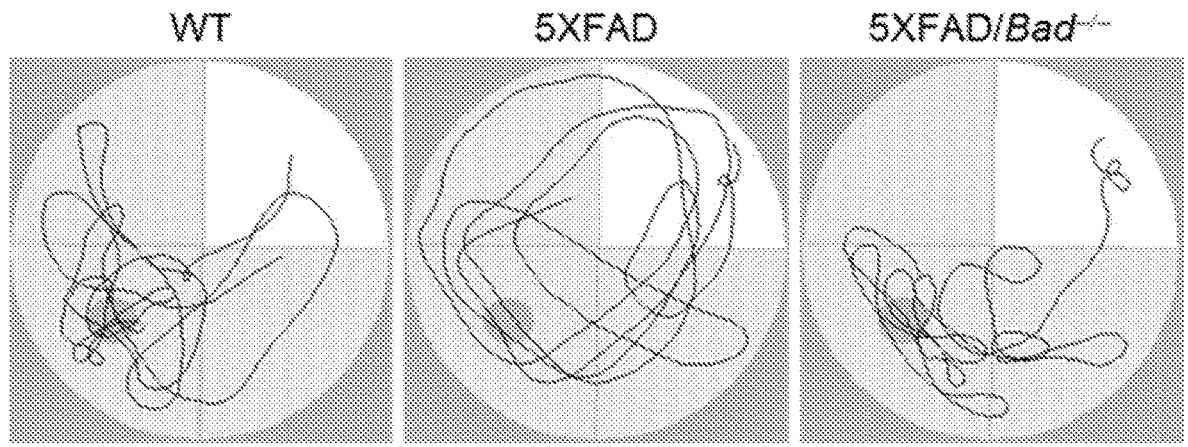

FIG. 24c shows representative swimming track plots of WT, 5XFAD, and 5XFAD/Bad$^{-/-}$ mice in the probe test.

Figure 24D:
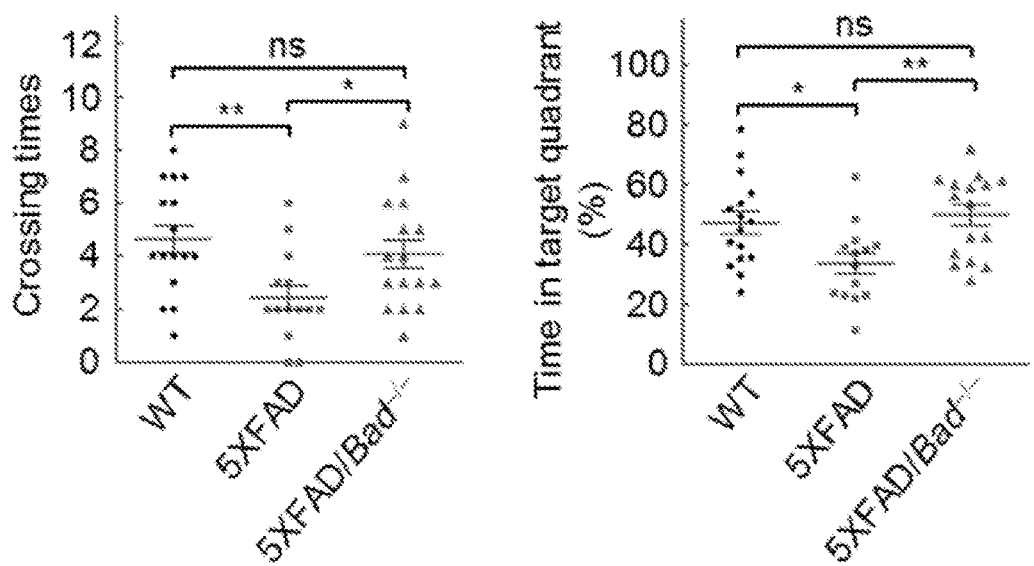

FIG. 24d shows statistical analysis of target crossing times and the time (%) spent in target quadrant in the probe test (mean f s.e.m., *P<0.05, **P<0.01, Student's t-test).

Figure 25A:
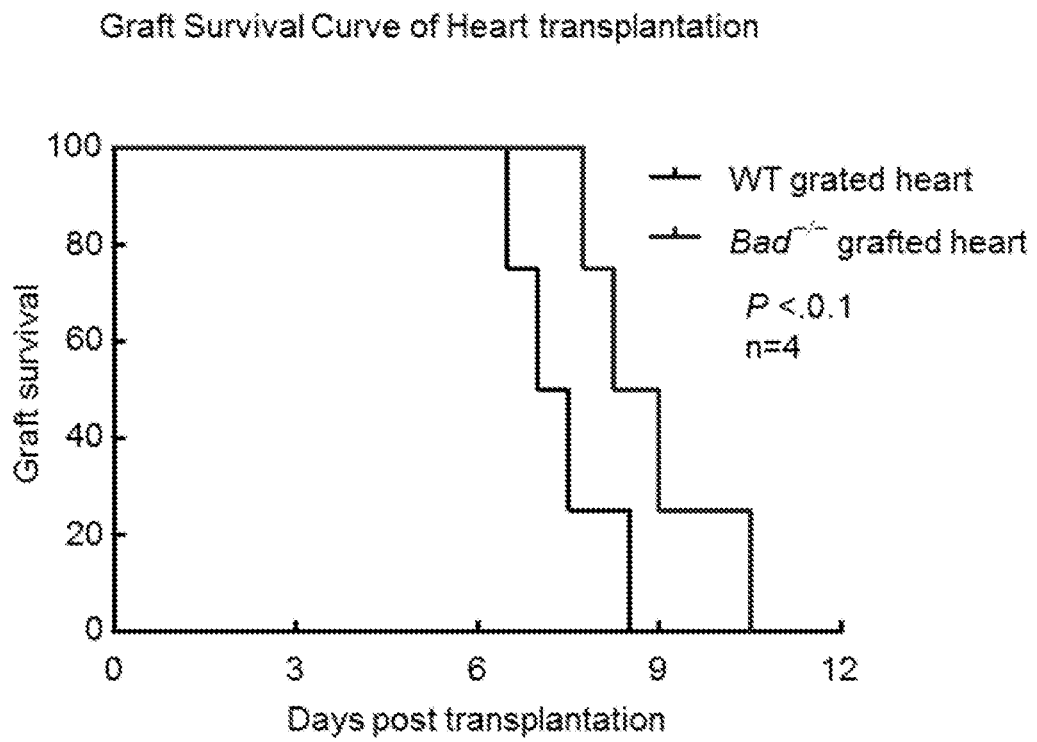

FIG. 25a shows a survival curve of grafted hearts from Bad knockout or their WT littermates (all C57/B6 background) to Balb/c receipt mice (days post-transplantation). When the hearts stopped beating, they were considered to be dead.

Figure 25B:
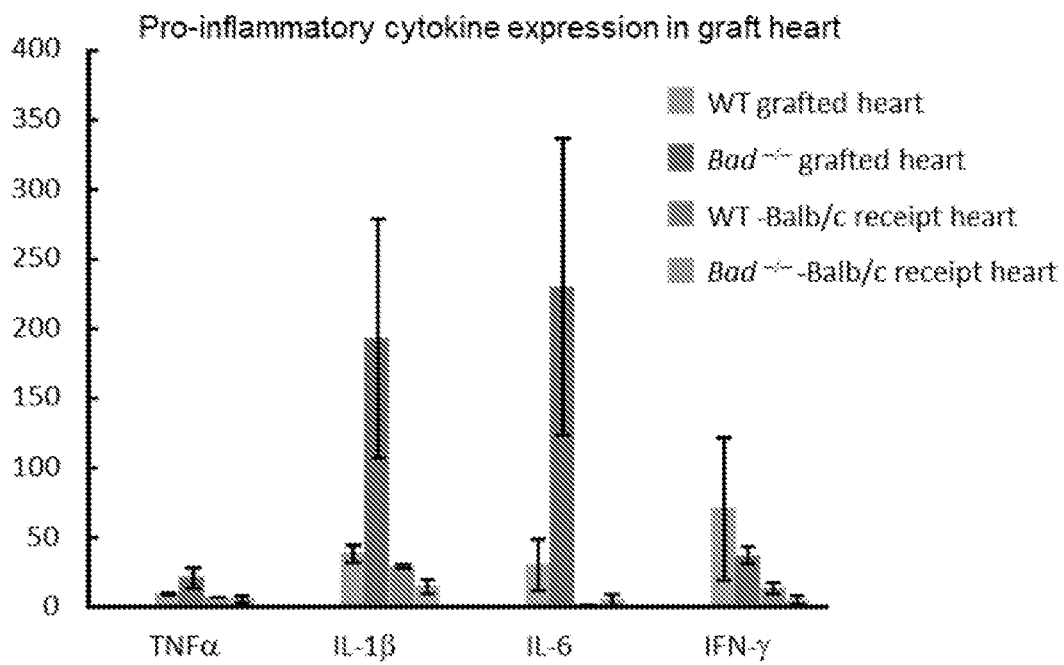

FIG. 25b shows local cytokine expression profiles of grafted hearts and host hearts, measured by real-time PCR.

Figure 26:
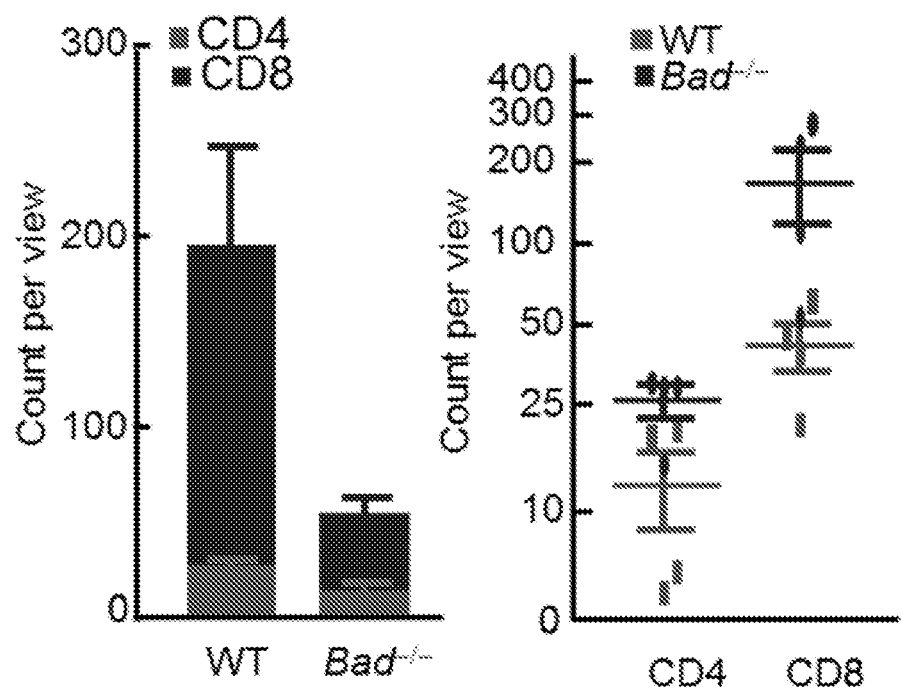

FIG. 26 shows quantified results of immunohistochemistry (IHC) staining of WT littermate and Bad knockout grafted hearts with anti-CD4 or anti-CD8 antibody. Samples were collected at the end point of the transplantation (grafted hearts stop beating). Quantification of immunostaining of CD4$^+$ and CD8$^+$ T cells in WT littermate and Bad knockout grafted hearts is shown in the bar and box plot. The numbers of positive cells were counted in three different random areas for both types of mice.

Figure 27:
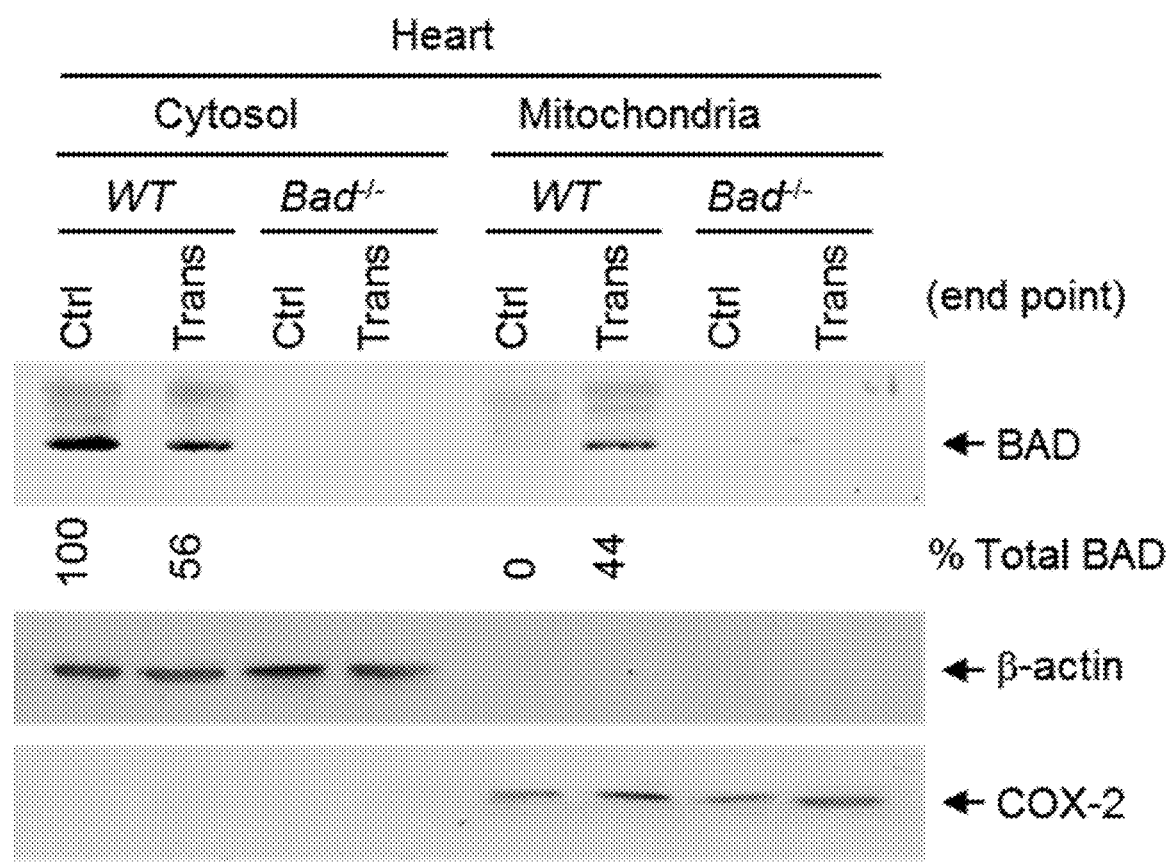

FIG. 27 is a western blot showing that transplantation induces BAD mitochondrial translocation. WT littermate and Bad knockout grafted hearts were isolated at the end point. Heart tissue extracts were separated into the cytosol and mitochondria by the cytosol and mitochondrial fractionation kit. BAD mitochondrial translocation was detected by immunoblotting using anti-BAD antibody and quantitated by ImageJ program. ß-actin and COX-2 were used as markers for the cytosol and mitochondria, respectively.

Figure 28:
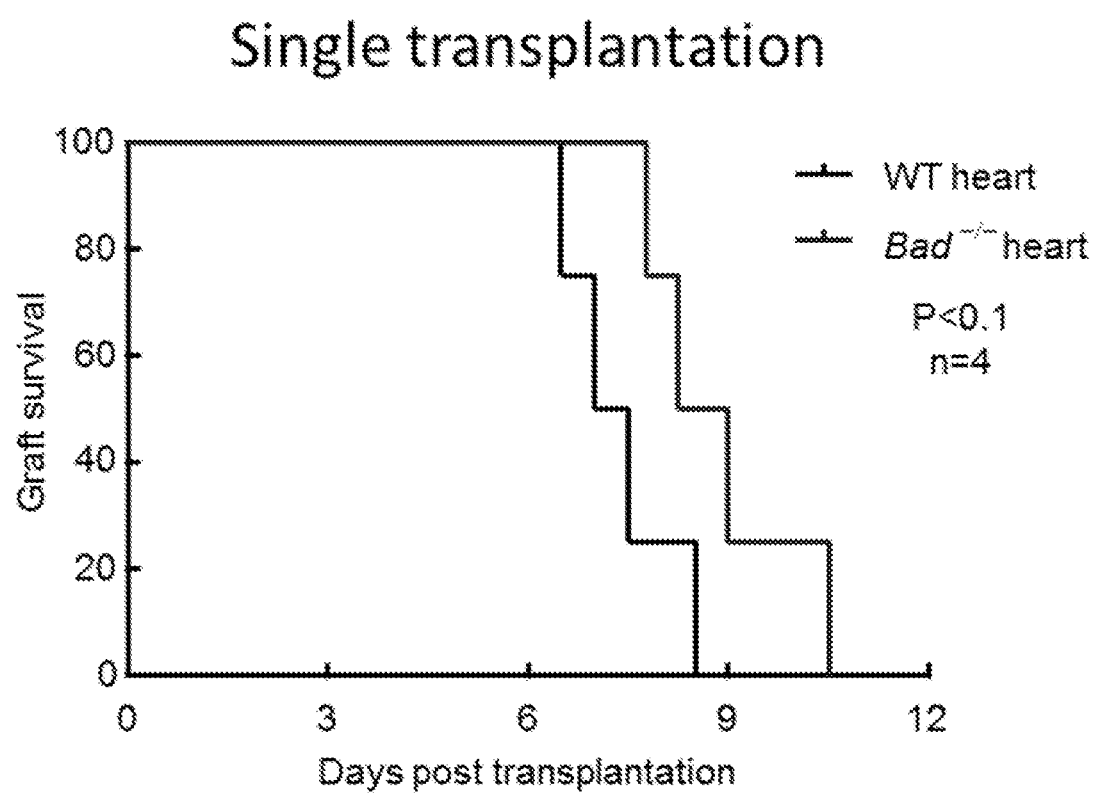

FIG. 28 is a plot showing graft survival for WT and Bad knockout hearts after a single transplantation.

Figure 29:
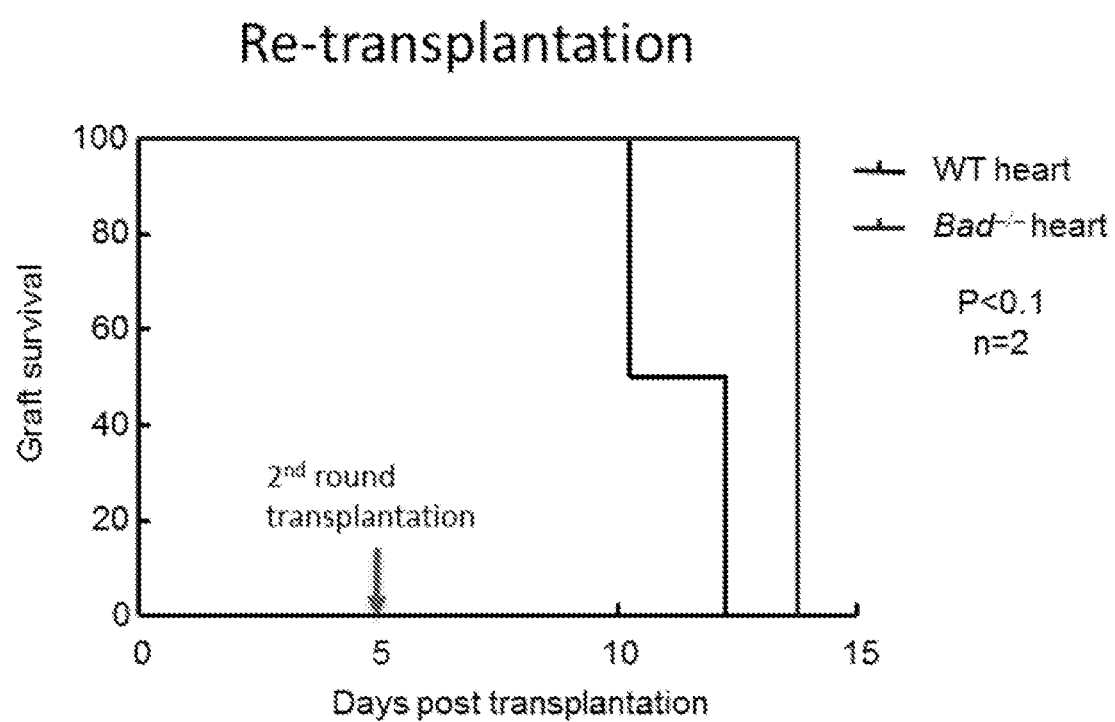

FIG. 29 is a plot showing graft survival for WT and Bad knockout hearts after a re-transplantation of the graft from FIG. 28 into a naïve host. The plot shows that the Bad knockout heart maintains beating in two consecutive transplantations (8.625 days and 8.75 days), while WT heart beats even shorter period after second transplantation (7.25 days and 6.25 days).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to prevention and treatment of pathologies including but not limiting to cell death and tissue/organ damage induced by TNFα cytotoxicity in a variety of diseases including but not limiting to severe sepsis. In some embodiments, the technology relates to compositions and methods for inhibiting, blocking, minimizing, and/or reducing cytotoxic TNFα-induced re-localization of BAD from actin stress fibers at cytoskeleton to cytosol.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The terms "protein" and "polypeptide" refer to compounds comprising amino acids joined via peptide bonds and are used interchangeably. Conventional one and three-letter amino acid codes are used herein as follows—Alanine: Ala, A; Arginine: Arg, R; Asparagine: Asn, N; Aspartate: Asp, D; Cysteine: Cys, C; Glutamate: Glu, E; Glutamine: Gln, Q; Glycine: Gly, G; Histidine: His, H; Isoleucine: Ile, I; Leucine: Leu, L; Lysine: Lys, K; Methionine: Met, M; Phenylalanine: Phe, F; Proline: Pro, P; Serine: Ser, S; Threonine: Thr, T; Tryptophan: Trp, W; Tyrosine: Tyr, Y; Valine: Val, V. As used herein, the codes Xaa and X refer to any amino acid.

In some embodiments compounds of the technology comprise an antibody component or moiety, e.g., an antibody or fragments or derivatives thereof. Fragments of antibodies include, but are not limited to, Fab (e.g., by papain digestion), F(ab')2 (e.g., by pepsin digestion), Fab' (e.g., by pepsin digestion and partial reduction) and Fv or scFv (e.g., by molecular biology techniques) fragments.

As used herein, the terms "subject" and "patient" refer to any animal, such as a mammal like a dog, cat, bird, livestock, and preferably a human (e.g., a human).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent. As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (e.g., minimize or lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive versus conventional treatment).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

Description

Apoptosis induced by tumor necrosis factor-α (TNFα) is suppressed by: 1) activation of the transcription factor NF-kB by inhibitor of nuclear factor-κB (NF-κB) kinase complex (IKK); and 2) inhibition of the pro-apoptotic BCL-2 family member protein BCL-2-associated death promoter (BAD) by IKK under physiological and developmental conditions. However, the mechanism underlying TNFα cytotoxicity in diseases is poorly understood.

During the development of embodiments of the technology described herein, experiments were conducted that produced data indicating that TNFα cytotoxicity in severe sepsis is mediated by BAD despite concurrent IKK activation. For example, data indicated that high dose TNFα alone induced Src-p190GAP-mediated early-phase inactivation of RhoA, which released substantial BAD from actin stress fibers from the cytoskeleton into the cytosol. Consequently, the increased cytosol BAD exceeded the IKK phosphorylation capacity, resulting in the translocation of BAD into mitochondria, where BAD acts to trigger apoptosis. Additional experiments indicated that BAD-mediated TNFα cytotoxicity is associated with polymicrobial infection-induced multi-organ damage and mortality; and that Bad-deficient mice were protected from polymicrobial infection-induced multi-organ damage and mortality. The translocation of BAD into mitochondria is augmented in the damaged colon epithelium of severe sepsis patients. The data indicate that TNFα-induced BAD pro-apoptotic activity is a factor contributing to multi-organ damage and mortality in severe sepsis.

The technology described herein includes embodiments of technology based on the discovery of a long-sought underlying mechanism of TNFα cytotoxicity in disease, e.g., inflammatory disease, infectious disease, etc. In particular, release of BAD into a form having pro-apoptotic activity by cytotoxic dose TNFα is pathologically relevant because it is associated with multi-organ damage and mortality in severe sepsis due to polymicrobial infection. Given the importance of TNFα cytotoxicity in many human diseases, technologies based on modulating the activity of BAD thus find use in many human diseases. For example, the identification of BAD as a key effector involved in organ damage and mortality in severe sepsis indicates that BAD is an appropriate therapeutic target for the treatment of severe sepsis, a deadly disease with no efficient therapies. Further, inhibition of BAD pro-apoptotic activity may selectively limit organ damage and mortality in severe sepsis without inhibition of the beneficial inflammatory response-mediated host defense against bacteria.

The technology provided herein is based, in some embodiments, on the discovery that cytotoxic dose TNFα inactivates the RhoA protein by stimulating strong and sustained Src-dependent activation of p190GAP. The inactivation of RhoA results in depolymerization of F-actin filaments and release of BAD into the cytosol at a level that is not completely phosphorylated by IKK. The non-phosphorylated BAD translocates to the mitochondria, where it promotes apoptosis.

Thus, activation of the Scr-p190GAP pathway by cytotoxic dose TNFα strongly inactivates RhoA and, consequently, promotes actin depolymerization and release of BAD into the cytosol. And, as shown in the examples, inhibition of Src or p190GAP significantly reduced cytotoxic dose TNFα-induced depolymerization of actin and thus also reduced release of BAD into the cytosol. Accordingly, in some embodiments the technology provided herein relates to inhibiting Src or p190GAP to ameliorate (e.g., reduce, minimize, and/or eliminate) the cytotoxic effects of TNFα, e.g., as mediated by BAD translocation to mitochondria and subsequent apoptosis.

Accordingly, the technology relates to prevention and treatment of pathologies including but not limiting to cell death and tissue/organ damage induced by TNFα cytotoxicity in a variety of diseases including but not limiting to severe sepsis. In some embodiments, the technology relates to compositions and methods for inhibiting, blocking, minimizing, and/or reducing cytotoxic TNFα-induced re-localization of BAD from actin stress fibers at cytoskeleton to cytosol. In some embodiments, the technology provides for screening siRNA or miRNA libraries to identify proteins that are involved in TNFα-induced depolymerization of the cytoskeleton. In some embodiments, the technology provides for screening small molecules or miRNA libraries that specifically inhibit TNFα-induced actin stress fiber depolymerization at cytoskeleton or promoting actin stress fiber polymerization at cytoskeleton. For example, some embodiments relate to screening and identifying small molecules that specifically inhibit p190GAP or that specifically inhibit other GAPs that inhibit RhoA activity. Some embodiments relate to screening and identifying small molecules that activate RhoA directly or indirectly through activation of the ERK-GEF-H1 pathway. Some embodiments relate to screening and identifying small molecules that activate a downstream target of RhoA or that directly stabilize actin stress fiber at cytoskeleton. Some embodiments relate to compositions and methods that directly eliminate BAD. For example, some embodiments comprise targeting BAD for proteasomal degradation, e.g., by screening small chemical compounds to activate the E3 ligase that targets BAD for proteasomal degradation.

While drugs that target TNFα are known, directly targeting TNFα eliminates its beneficial functions, e.g., in other crucial pathways. For example, TNFα-induced activation of NF-κB is required for cell survival and transient inflammation against pathogen invasion. The present technology targets only the detrimental effects of TNFα by inhibiting, reducing, and/or minimizing BAD re-localization from actin stress fibers at cytoskeleton to cytosol (e.g., using a Src inhibitor), which prevents BAD mitochondrial translocation-mediated cell death and consequent tissue or organ damage and mortality. The present technology does not impair NF-κB activation, thus providing a technology to modulate (e.g., reduce, inhibit, minimize) TNFα cytotoxicity in diseases without impairing other beneficial functions of TNFα. The technology finds use in preventing and treating diseases in which TNFα cytotoxicity contributes to cell death and tissue/organ damage, e.g., severe sepsis, transplant rejection, graft-versus-host disease, rheumatoid arthritis, AIDS/HIV, Zika fever, adult respiratory distress syndrome (ARDS), vascular leakage syndrome, adrenal hemorrhage, acute renal tubular necrosis, gastrointestinal necrosis, weight loss, meningitis, and in neuronal degenerative disease such as Alzheimer's disease and multiple sclerosis.

Src

Src is a non-receptor protein kinase that phosphorylates specific tyrosine residues in other proteins. In humans, the Src protein is encoded by the SRC gene. There are nine members of the Src kinase family: Src (also known as "c-Src"), Yes, Fyn, Fgr, Yrk, Lyn, Blk, Hck, and Lck. Src comprises six functional domains: (1) a Src homology (SH) 4 domain (SH4 domain); (2) a "unique" region; (3) a SH3 domain; (4) a SH2 domain; (5) a catalytic (e.g., kinase) domain; and (6) a regulatory domain. When Src is inactive, the phosphorylated tyrosine group at the 527 position interacts with the SH2 domain which helps the SH3 domain interact with the flexible linker domain and thereby keeps the inactive unit tightly bound. Activation of Src causes dephosphorylation of tyrosine 527. This induces changes in the protein structure that expose the SH3, SH2 and kinase domains and result in the autophosphorylation of tyrosine 416. Src is activated by many proteins such as, e.g., adhesion receptors, receptor tyrosine kinases, G-protein coupled receptors, and cytokine receptors. When Src is activated, it promotes survival, angiogenesis, proliferation, and invasion pathways. It also regulates angiogenic factors, vascular permeability, and matrix metalloproteinase-9. A number of tyrosine kinase inhibitors target Src, including dasatinib, which has been approved for treating chronic myeloid leukemia (CML) and Philadelphia chromosome-positive (PH+) acute lymphocytic leukemia (ALL) Dasatinib is also in clinical trials for the use in non-Hodgkin's lymphoma, metastatic breast cancer, and prostate cancer. Other Src inhibitor drugs that are in clinical trials include bosutinib, bafetinib, saracatinib, XL1-999, KX01, and XL228

Compositions and Kits

Accordingly, in some embodiments, the present technology provides compositions and kits, e.g., for administration to a subject. In some embodiments, the technology relates to compositions that inhibit Src activity. The technology is not limited in the composition that inhibits Src activity. For example, in some embodiments Src activity is inhibited by a nucleic acid (e.g., an RNA, a DNA, a DNA/RNA hybrid; e.g., an antisense nucleic acid, a microRNA, an siRNA, an aptamer, etc.), by a protein (e.g., an enzyme, an antibody; e.g., a protein that stabilizes the inactive form of Src, a protein that promotes phosphorylation of Src at tyrosine 527, a protein that digests Src, a protein that promotes dephosphorylation of tyrosine 416, a protein that binds to the catalytic kinase domain, etc.), or a small molecule (e.g., drug) that inhibits Src activity.

In some embodiments, compositions comprise a small molecule kinase inhibitor. In some embodiments, compositions comprise a small molecule inhibitor of the Src kinase domain. In some embodiments, the compositions comprise a small molecule inhibitor of Src phosphorylation. In some embodiments, the compositions comprise a small molecule inhibitor of Src phosphorylation that does not inhibit phosphorylation of other proteins, e.g., IKK.

For example, some embodiments of compositions comprise dasatinib (N-(2-chloro-6-methylphenyl)-2-[[6-[4-(2-hydroxyethyl)-1-piperazinyl]-2-methyl-4-pyrimidinyl] amino]-5-thiazole carboxamide monohydrate). Some embodiments of compositions comprise saracatinib (N-(5-chloro-1,3-benzodioxol-4-yl)-7-[2-(4-methyl-1-piperazinyl) ethoxy]-5-[tetrahydro-2H-pyran-4-yl)oxy]-4-quinazolinamine). In some embodiments, the compositions comprise a deuterated small molecule. In some embodiments, compositions comprise one of the following small molecules:

TABLE 1

Src inhibitors

| Name | Formula | Systematic name |
|---|---|---|
| ZG5126 | $C_{27}H_{28}D_4ClN_5O_5$ | N-(5-chlorobenzo[d][1,3]dioxol-4-yl)-7-(2-(4-methylpiperazin-1-yl)ethoxy-1,1,2,2-$d_4$)-5-((tetrahydro-2H-pyran-4-yl)oxy) quinazolin-4-amine) |
| ZG5127 | $C_{27}H_{30}D_2ClN_5O_5$ | N-(5-chlorobenzo[d][1,3]dioxol-4-yl)-7-(2-(4-methylpiperazin-1-yl)ethoxy-2,2-$d_2$)-5-((tetrahydro-2H-pyran-4-yl)oxy)quinazolin-4-amine) |
| ZG5128 | $C_{27}H_{30}D_2ClN_5O_5$ | N-(5-chlorobenzo[d][1,3]dioxol-4-yl-2,2-$d_2$)-7-(2-(4-methylpiperazin-1-yl)ethoxy)-5-((tetrahydro-2H-pyran-4-yl)oxy) quinazolin-4-amine |
| ZG5129 | $C_{27}H_{29}D_3ClN_5O_5$ | N-(5-chlorobenzo[d][1,3]dioxol-4-yl)-7-(2-(4-(methyl-$d_3$)piperazin-1-yl)ethoxy)-5-((tetrahydro-2H-pyran-4-yl)oxy)quinazolin-4-amine) |
| ZG5130 | $C_{27}H_{30}D_2ClN_5O_5$ | N-(5-chlorobenzo[d][1,3]dioxol-4-yl)-7-(2-(4-methylpiperazin-1-yl)ethoxy-1,1-$d_2$)-5-((tetrahydro-2H-pyran-4-yl)oxy)quinazolin-4-amine) |
| ZG5131 | $C_{27}H_{31}DClN_5O_5$ | N-(5-chlorobenzo[d][1,3]dioxol-4-yl)-7-(2-(4-methylpiperazin-1-yl)ethoxy)-5-((tetrahydro-2H-pyran-4-yl-4-d)oxy) quinazolin-4-amine) |
| ZG5132 | $C_{27}H_{27}D_5ClN_5O_5$ | N-(5-chlorobenzo[d][1,3]dioxol-4-yl-2,2-$d_2$)-7-(2-(4-(methyl-$d_3$)piperazin-1-yl)ethoxy)-5-((tetrahydro-2H-pyran-4-yl)oxy)quinazolin-4-amine) |
| ZG5133 | $C_{27}H_{29}D_3ClN_5O_5$ | N-(5-chlorobenzo[d][1,3]dioxol-4-yl-2,2-$d_2$)-7-(2-(4-methylpiperazin-1-yl)ethoxy)-5-((tetrahydro-2H-pyran-4-yl-4-d)oxy) quinazolin-4-amine) |
| ZG5134 | $C_{27}H_{26}D_6ClN_5O_5$ | N-(5-chlorobenzo[d][1,3]dioxol-4-yl-2,2-$d_2$)-7-(2-(4-methylpiperazin-1-yl)ethoxy-1,1,2,2-$d_4$)-5-((tetrahydro-2H-pyran-4-yl)oxy)quinazolin-4-amine) |
| ZG5146 | $C_{27}H_{22}D_{10}ClN_5O_5$ | N-(5-chlorobenzo[d][1,3]dioxol-4-yl-2,2-$d_2$)-7-(2-(4-(methyl-$d_3$)piperazin-1-yl)ethoxy-1,1,2,2-$d_4$)-5-((tetrahydro-2H-pyran-4-yl-4-d)oxy)quinazolin-4-amine |
| ZG5147 | $C_{27}H_{26}D_6ClN_5O_5$ | N-(5-chlorobenzo[d][1,3]dioxol-4-yl-2,2-$d_2$)-7-(2-(4-(methyl-$d_3$)piperazin-1-yl)ethoxy)-5-((tetrahydro-2H-pyran-4-yl-4-d) oxy)quinazolin-4-amine |
| ZG5151 | $C_{27}H_{23}D_9ClN_5O_5$ | N-(5-chlorobenzo[d][1,3]dioxol-4-yl-2,2-$d_2$)-7-(2-(4-(methyl-$d_3$)piperazin-1-yl)ethoxy-1,1,2,2-$d_4$)-5-((tetrahydro-2H-pyran-4-yl)oxy)quinazolin-4-amine |

For example, in some embodiments, compositions comprise a compound having a structure according to:

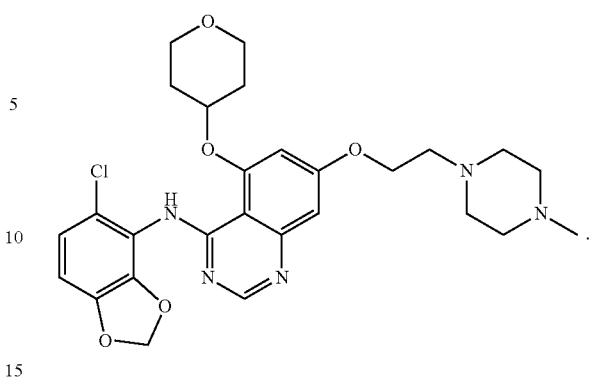

In some embodiments, compositions comprise a compound according to

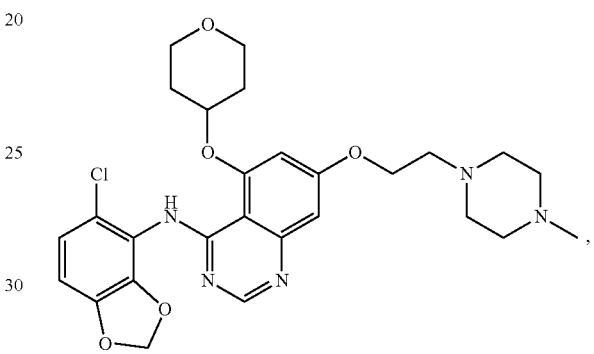

wherein the compound comprises a deuterium atom. In some embodiments, the compound comprises more than one deuterium atom, e.g., 2, 3, 4, 5, 6, 7, 8, 9, 10, 11, 12, 13, 14, 15, or more deuterium atoms. Some embodiments provide a compound and compositions comprising a compound having a structure according to

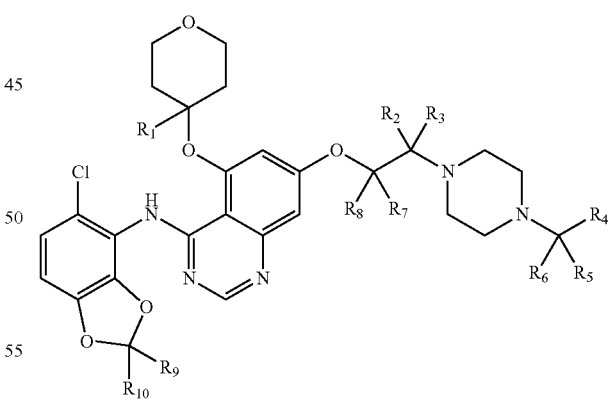

wherein one or more of $R_1$, $R_2$, $R_3$, $R_4$, $R_5$, $R_6$, $R_7$, $R_8$, $R_9$, and/or $R_{10}$ comprises a deuterium. In some embodiments, each of $R_2$, $R_3$, $R_7$, and $R_8$ comprises a deuterium; in some embodiments, each of $R_2$ and $R_3$ comprises a deuterium; in some embodiments, each of $R_9$ and $R_{10}$ comprises a deuterium; in some embodiments, each of $R_4$, $R_5$, and $R_6$ comprises a deuterium; in some embodiments, each of $R_7$ and $R_8$ comprises a deuterium; in some embodiments, each of $R_2$, $R_3$, $R_7$, $R_8$, $R_9$, and $R_{10}$ comprises a deuterium; in some embodiments, $R_1$ comprises a deuterium; in some embodiments, each of $R_4$, $R_5$, $R_6$, $R_9$, and $R_{10}$ comprises a deuterium; in some embodiments, each of $R_1$, $R_9$, and $R_{10}$ comprises a deuterium; in some embodiments, each of $R_1$, $R_2$, $R_3$, $R_4$, $R_5$, $R_6$, $R_7$, $R_8$, $R_9$, and $R_{10}$ comprises a deuterium; in some embodiments, each of $R_1$, $R_4$, $R_5$, $R_6$, $R_9$, and $R_{10}$ comprises a deuterium; and, in some embodiments, each of $R_2$, $R_3$, $R_4$, $R_5$, $R_6$, $R_7$, $R_8$, $R_9$, and $R_{10}$ comprises a deuterium.

In some embodiments, one or more of $R_1$, $R_2$, $R_3$, $R_4$, $R_5$, $R_6$, $R_7$, $R_8$, $R_9$, and/or $R_{10}$ is or consists of a deuterium. In some embodiments, each of $R_2$, $R_3$, $R_7$, and $R_8$ is or consists of a deuterium; in some embodiments, each of $R_2$ and $R_3$ is or consists of a deuterium; in some embodiments, each of $R_9$ and $R_{10}$ is or consists of a deuterium; in some embodiments, each of $R_4$, $R_5$, and $R_6$ is or consists of a deuterium; in some embodiments, each of $R_7$ and $R_8$ is or consists of a deuterium; in some embodiments, each of $R_2$, $R_3$, $R_7$, $R_8$, $R_9$, and $R_{10}$ is or consists of a deuterium; in some embodiments, $R_1$ is or consists of a deuterium; in some embodiments, each of $R_4$, $R_5$, $R_6$, $R_9$, and $R_{10}$ is or consists of a deuterium; in some embodiments, each of $R_1$, $R_9$, and $R_{10}$ is or consists of a deuterium; in some embodiments, each of $R_1$, $R_2$, $R_3$, $R_4$, $R_5$, $R_6$, $R_7$, $R_8$, $R_9$, and $R_{10}$ is or consists of a deuterium; in some embodiments, each of $R_1$, $R_4$, $R_5$, $R_6$, $R_9$, and $R_{10}$ is or consists of a deuterium; and, in some embodiments, each of $R_2$, $R_3$, $R_4$, $R_5$, $R_6$, $R_7$, $R_8$, $R_9$, and $R_{10}$ is or consists of a deuterium.

In some embodiments, the technology relates to compositions that promote polymerization of F-actin. The technology is not limited in the compositions that promote polymerization of F-actin. For example, in some embodiments F-actin polymerization is promoted by a nucleic acid (e.g., an antisense nucleic acid, a microRNA, an siRNA, an aptamer, etc.), by a protein (e.g., a protein that stabilizes F-actin, etc.), or a small molecule (e.g., drug) that promotes or stabilizes F-actin polymers and polymerization.

In some embodiments, the technology relates to compositions that inhibit depolymerization of F-actin. The technology is not limited in the compositions that inhibit depolymerization of F-actin. For example, in some embodiments F-actin depolymerization is inhibited by a nucleic acid (e.g., an antisense nucleic acid, a microRNA, an siRNA, an aptamer, etc.), by a protein (e.g., a protein that stabilizes F-actin, etc.), or a small molecule (e.g., drug) that inhibits F-actin depolymerization.

In some embodiments, the technology relates to compositions that degrade and/or inhibit BAD. The technology is not limited in the compositions that degrade and/or inhibit BAD. For example, in some embodiments inhibition and/or degradation of BAD is promoted by a nucleic acid (e.g., an antisense nucleic acid, a microRNA, an siRNA, an aptamer, etc.), by a protein (e.g., a protein that degrades BAD, a protein that marks BAD for proteasomal degradation, etc.), or a small molecule (e.g., drug) that inhibits BAD activity. Some embodiments relate to compositions that promote the phosphorylation of BAD and/or that promote the interaction of BAD with 14-3-3 protein. In some embodiments, the technology relates to compositions that promote BAD sequestration in the cytosol and/or that inhibit translocation of BAD into the mitochondria.

In some embodiments, the technology relates to compositions that activate (e.g., phosphorylate) p190GAP. The technology is not limited in the compositions that activate (e.g., phosphorylate) p190GAP. For example, in some embodiments p190GAP activation is promoted by a nucleic acid (e.g., an antisense nucleic acid, a microRNA, an siRNA, an aptamer, etc.), by a protein (e.g., a protein that stabilizes F-actin, etc.), or a small molecule (e.g., drug) that activates p190GAP.

Pharmaceutical Compositions

It is generally contemplated that the compounds related to the technology are formulated for administration to a mammal, and especially to a human with a condition that is responsive to the administration of such compounds (e.g., TNFα-induced apoptosis, organ damage, tissue damage, etc.). Therefore, where contemplated compounds are administered in a pharmacological composition, it is contemplated that the contemplated compounds are formulated in admixture with a pharmaceutically acceptable carrier.

Compositions may, for example, be in the form of tablets, resolvable tablets, capsules, bolus, drench, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, chewing-gums, creams, salves, jellies, gels, pastes, toothpastes, rinses, dental floss and tooth-picks, liquid aerosols, dry powder formulations, HFA aerosols or organic or inorganic acid addition salts.

For example, contemplated compounds can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form, and all metabolites of the compounds herein are therefore specifically contemplated. In addition, contemplated compounds (and combinations thereof) may be administered in combination with yet further agents.

With respect to administration to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to maximize efficacy but will depend on such factors as weight, diet, concurrent medication, and other factors that those skilled in the art will recognize.

Pharmaceutical compositions preferably comprise one or more compounds of the present technology associated with one or more pharmaceutically acceptable carriers, diluents, or excipients. Pharmaceutically acceptable carriers are known in the art such as those described in, for example, Remingtons Pharmaceutical Sciences, Mack Publishing Co. (A. R. Gennaro edit. 1985), explicitly incorporated herein by reference for all purposes.

Accordingly, in some embodiments, the immunotherapeutic agent is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of the compound over time.

In some embodiments, the compositions are formulated so that the active ingredient is embedded in a matrix of an insoluble substance (e.g., various acrylics, chitin) such that the dissolving compound finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustained-release formulations, the compound dissolves into the matrix and the matrix physically swells to form a gel, allowing the compound to exit through the gel's outer surface. In some embodiments, the formulations are in a micro-encapsulated form, e.g., which is used in some embodiments to produce a complex dissolution profile. For example, by coating the compound around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. "Particles" as used herein means nano- or microparticles (or in some instances larger) that can consist in whole or in part of the compounds as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, non-erodible, biodegradable, or nonbiodegradable materials or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in Macromolecules, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly (lauryl methacrylate), poly(phenylmethacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of the compounds or salts thereof to inhibit formation of degradation products. A solution is provided that contains the compound or salts thereof and at least one inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the compound is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the compound is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof.

In some embodiments, the compound is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the compound is formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the compound is formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the compound is formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Methods

Embodiments of the technology relate to methods of treating TNFα-related cytotoxicity, e.g., apoptosis, cell death, organ damage, tissue damage, etc. In some embodiments, embodiments relate to administering a compound described herein (e.g., a Src inhibitor) to a patient in need of treatment for TNFα-related cytotoxicity, e.g., apoptosis, cell death, organ damage, tissue damage, etc.

In some embodiments, the technology relates to methods of providing a dosage of a compound (e.g., Src inhibitor, siRNA, or other compound described herein) to a subject.

In some embodiments, a compound, a derivative thereof, or a pharmaceutically acceptable salt thereof, is administered in a pharmaceutically effective amount. In some embodiments, a compound, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of the compound or related compounds will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, the compound, a derivative thereof, or a pharmaceutically acceptable salt thereof, is administered orally.

In some embodiments, a single dose of a compound or a related compound is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years). In such embodiments, compounds may be taken on a regular scheduled basis (e.g., daily, weekly, etc.) for the duration of the extended period.

The technology also relates to methods of treating a subject with a drug appropriate for the subject's malady. According to another aspect of the technology, a method is provided for treating a subject in need of such treatment with an effective amount of a compound or a salt thereof. The method involves administering to the subject an effective amount of a compound or a salt thereof in any one of the pharmaceutical preparations described above, detailed herein, and/or set forth in the claims. The subject can be any subject in need of such treatment. In the foregoing description, the technology is in connection with a compound or salts thereof. Such salts include, but are not limited to, bromide salts, chloride salts, iodide salts, carbonate salts, and sulfate salts. It should be understood, however, that the compound is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "compound" appears.

In some embodiments, a subject is tested to assess the presence, the absence, or the level of a malady and/or a condition. Such testing is performed, e.g., by assaying or measuring a biomarker, a metabolite, a physical symptom, an indication, a bacterial load (e.g., infection), etc., to determine the risk of or the presence of the malady or condition. In some embodiments, the subject is treated with a compound based on the outcome of the test. In some embodiments, a subject is treated, a sample is obtained and the level of detectable agent is measured, and then the subject is treated again based on the level of detectable agent that was measured. In some embodiments, a subject is treated, a sample is obtained and the level of detectable agent is measured, the subject is treated again based on the level of detectable agent that was measured, and then another sample is obtained and the level of detectable agent is measured. In some embodiments, other tests (e.g., not based on measuring the level of detectable agent) are also used at various stages, e.g., before the initial treatment as a guide for the initial dose. In some embodiments, a subsequent treatment is adjusted based on a test result, e.g., the dosage amount, dosage schedule, identity of the drug, etc. is changed. In some embodiments, a patient is tested, treated, and then tested again to monitor the response to therapy and/or change the therapy. In some embodiments, cycles of testing and treatment may occur without limitation to the pattern of testing and treating, the periodicity, or the duration of the interval between each testing and treatment phase. As such, the technology contemplates various combinations of testing and treating without limitation, e.g., test/treat, treat/test, test/treat/test, treat/test/treat, test/treat/test/treat, test/treat/test/test, test/treat/test/test/treat/treat/test, treat/treat/test/treat, test/treat/treat/test/treat/treat, etc.

Uses

In some embodiments, the technology finds use to prevent and treat human diseases that are caused by TNFα cytotoxicity (e.g., comprising TNFα-related cell death and tissue/organ damage). In some embodiments, the technology finds use in research. For example, in some embodiments the technology finds use in screening for molecules (e.g., protein, nucleic acid (e.g., siRNA), or small molecule) that can inhibit, prevent, block, reduce, minimize, eliminate, or antagonize TNFα-induced BAD re-localization from actin stress fibers at cytoskeleton to cytosol to prevent or treat human diseases or enhance a healthy person's disease tolerance. In some embodiments, the technology finds use in eliminating, inhibiting, or reducing BAD pro-apoptotic activity or BAD protein level by introducing molecules (e.g., protein, nucleic acid (e.g., siRNA), or small molecule) to prevent or treat human diseases or to increase a healthy individual's disease tolerance.

EXAMPLES

Materials and Methods

During the development of embodiments of the technology described herein, experiments were conducted according to the following methods and using the following materials.

Animal Models, Histology and Serology Measurement.

Bad-deficient mice were provided by Dr. Nika N. Danial (Dana-Farber Cancer Institute) and have been backcrossed into the C57BL/6J genetic background for at least 14 generations and validated by genome scanning to be 99.9% congenic with C57BL/6J (30). Heterozygous Bad-deficient mice were further bred to generate age-matched WT littermate and knockout experimental mice. Tnf-R1-deficient mice in C57BL/6J genetic background were purchased from Jackson laboratory and bred with WT C57BL/6J mice to generate heterozygote TnfR1-deficient mice, which were further crossed to generate age-matched WT littermate and knockout experimental mice. Gender-matched and age-matched (male, 6-8 week old) WT littermate, Bad-deficient, and TnfR1-deficient mice, as well as Bad(WT)$^+$ and Bad (LacZ)$^+$ control mice (12) were used.

For the polymicrobial infection model, the cecal ligation puncture (CLP) procedure was performed (25). The severity of CLP was adjusted to a high-grade sepsis that comprised ligation of 60-80% of the cecum, and perforating the cecum by single through-through puncture at the tip of the cecum with 21 gauge needle. For the mock CLP procedure ("Sham"), mice underwent the same abdominal surgery as the experimental CLP procedure, except the cecal ligation and puncture steps were not performed. The bacterial infusion and lipopolysaccharide (LPS) models were performed by intraperitoneal (i.p.) injection of $E.$ $coli$ (ATCC 25922). A number of $3 \times 10^6$ CFU were injected to provide a non-lethal dose; a number of $3 \times 10^7$ CFU were injected to provide a lethal dose. In some experiments, LPS ($E.$ $coli$ serotype 0111:B4; Sigma) at a dose of 35 mg/kg body weight was injected.

For analyzing antibiotic potency, Ceftriaxone (50 mg/kg body weight) was i.p. injected 10 hours after $E.$ $coli$ injection. All reagents were balanced with sterile phosphate-buffered saline (PBS) to provide the same total volume of injection solution for both control mice and experimental mice. Mice were scarified for analyzing BAD subcellular localizations, blood bacteria burden, production of inflammatory and anti-inflammatory cytokines, serology, and liver and colon histology. For the rescue experiment, Bad-deficient mice were injected through the tail vein with purified recombinant adenoviral vector encoding Bad or a control vector encoding LacZ. In these experiments, a total dose of $4 \times 10^9$ infectious units per ml (IFUs) in a volume of 100 μl per animal were injected to generate Bad(WT)$^+$ mice or Bad(LacZ)$^+$ mice, respectively, as reported previously (12). The mortality rate was recorded for up to 120 hours for the CLP model and for 50-60 hours for the $E.$ $coli$ and LPS models after the treatment, and dying mice were pre-moved. Statistical analysis was performed by the log rank (Mantel-Cox) test. All mice were maintained in a specific pathogen-free facility and housed according to established procedures. All animal experiments were conducted in accordance with the protocols approved by the Institutional Animal Care and Use Committee of the University of Chicago.

To analyze tissue injury, liver lobes and colon were excised and fixed in 4% paraformaldehyde for 12 hours. The tissues were sliced to 5 μm thickness. Hematoxylin and eosin (H&E) staining was performed at the University of Chicago Human Tissue Resource Center (HTRC). In situ cell death was analyzed by TUNEL staining (TUNEL Apoptosis Detection kit, EMD Millipore) according to the manufacturer protocol.

Blood samples were collected from the tail vein of animals at time points indicated in the figures. Serum from the blood samples was collected after centrifugation. Clinical chemistry tests (BioAssay Systems) including alanine amino transferase (ALT), aspartate amino transferase (AST), blood urea nitrogen (BUN), and lactate dehydrogenase (LDH) were used to measure biomarkers in mice according to the manufacturer protocol.

Cells, Antibodies and Reagents.

WT, Bad$^{-/-}$, IKß$^{-/-}$, and Jnk1$^{-/-}$ fibroblasts have been described previously (12, 15). Tnf-R1$^{-/-}$ and Casp-8$^{-/-}$ were provided by Dr. Zhenggang Liu at the National Cancer Institute (NCI) and RhoA$^{f/f}$ primary fibroblasts (31) were provided by Dr. Yi Zheng at the University of Cincinnati. RhoA(WT)$^+$ and RhoA(G63L)$^+$ mouse embryonic fibroblast (MEF) cells were prepared by infection of RhoA$^{f/f}$ primary fibroblasts with Ad/cre (10 moi), followed by transfection with expression vector pcDNA3 encoding WT RhoA or the RhoA(G63L) mutant, in which glutamic acid residue 63 has been replaced by leucine, (2 µg). Antibodies against BAD, IκBa, ERK, phospho-ERK, Src, Tyr416-phospho-Src, p190GAP, phosphotyrosine, RhoA, and phospho-IKKα/ß were from Cell Signaling. Anti-phospho-BAD$^{S26}$ antibody was from Abiocode, Inc. Antibodies against COX-2, BCL-xL, Tom 20, Cdc42, desmoplakin, and vimentin were from Santa Cruz. The antibody against IKKß was from Millipore. Antibody against α-tubulin was from Abeam. Purified GST and GST-BAD fusion proteins were used as described previously (12). Purified GST-Cofilin fusion proteins were purchased from BPS Bioscience. Purified G-actin monomer proteins were purchased from Cytoskeleton. Hoechst and Cytochalasin D were from Sigma. Jasplakinolide was from Biovision. Sphingosine-1-phosphate (S1P) was from Cayman Chemical. Latrunculin B was from Enzo life science. Alexia fluorescein-tagged second antibody, phalloidin, and MitoTracker were from Invitrogen. TNFα was from R&D (murine). siRNA were synthesized by IDT. The sequences of siRNA were:

```
siBAD
                            SEQ ID NO: 1
AGCUCCUGUUUGGAGUUUCAAA siBid
                            SEQ ID NO: 2
GGAGAACGACAAGGCCAUGC siCtrl
                            SEQ ID NO: 3
GGAGCGCACCAUCUUCUUC
```

The siRNA siBim, siRhoA and siSrc SMART pool were pre-synthesized stock from GE Dharmacon. siCdc42, siERK, and sip190GAP were pre-synthesized stock from Santa Cruz.

Flow Cytometric Assay and Quantitative Real-Time PCR.

For flow cytometric analysis, cells were harvested by trypsin digestion after different treatments as indicated in the figure legends. Annexin V and propidium iodide (PI) staining was performed with FITC Annexin V apoptosis Detection kit (BD Pharmingen). Apoptotic cells were analyzed by FACS canto flow cytometer (BD Biosciences).

For quantitative real-time PCR analysis, total RNA was extracted by Trizol reagent (Invitrogen) from cells or tissues as indicated in the figure legends. Total RNA (1 µg) was used for cDNA synthesis. SYBR Green real-time PCR master Mix (Invitrogen) and a Taqman PCR program were used for real-time PCR. PCR primers were synthesized from IDT. GAPDH was used as internal control. The sequences of primers were as follows:

```
mTNFα sense
                            SEQ ID NO: 4
CACAGAAAGCATGATCCGCGACGT mTNFα antisense
                            SEQ ID NO: 5
CGGCAGAGAGGAGGTTGACTTTCT IFNγ sense
                            SEQ ID NO: 6
TCAAGTGGCATAGATGTGGAAGAA IFNγ antisense
                            SEQ ID NO: 7
TGGCTCTGCAGGATTTTCATG IL-1β sense
                            SEQ ID NO: 8
CCAGCTTCAAATCTCACAGCA IL-1β antisense
                            SEQ ID NO: 9
CTTCTTTGGGTATTGCTTGGGATC IL-10 sense
                            SEQ ID NO: 10
GGTTGCCAAGCCTTATCGGA IL-10 antisense
                            SEQ ID NO: 11
ACCTGCTCCACTGCCTTGCT IL-6 sense
                            SEQ ID NO: 12
TCCAGTTGCCTTCTTGGGAC IL-6 antisense
                            SEQ ID NO: 13
GTACTCCAGAAGACCAGAGG IκBa sense
                            SEQ ID NO: 14
TGAAGGACGAGGAGTACGAGC IκBa antisense
                            SEQ ID NO: 15
TTCGTGGATGATTGCCAAGTG cIAP2 sense
                            SEQ ID NO: 16
ACGCAGCAATCGTGCATTTTG cIAP2 antisense
                            SEQ ID NO: 17
CCTATAACGAGGTCACTGACGG GAPDH sense
                            SEQ ID NO: 18
AACGACCCCTTCATTGAC GAPDH antisense
                            SEQ ID NO: 19
TCCACGACATACTCAGCAC
```

Human Colon Tissue Specimens.

Human colon tissue specimens of patients having bowel perforation of ulcerative colitis with severe sepsis were collected by surgical resection, fixed in 4% paraformaldehyde, and embedded in paraffin using standard methods. Corresponding clinical data were recorded but de-identified. Patients were identified as having bowel perforation of ulcerative colitis with severe sepsis using clinical diagnosis and histopathological criteria.

Immunoprecipitation, Caspase 3 Assays, G-LISA Assay, Active GEF-H1 Assay, Cell Fractionations, and Subcellular Localization Analysis and Calculation.

Immunoprecipitation was performed as previously described (12). Caspase 3 assay was performed with Casp-3 cellular activity assay kit using Casp-3 substrate Ac-DEVD-pNA (Calbiochem). Active RhoA, active Src, and active Cdc42 assays were performed with G-LISA assay biochemical kit (Cytoskeleton, Inc.). Active GEF-H1 assay was performed by using GST-RhoA(G17A) to pull down the active GEF-H1 from cell extracts and analyzed by immunoblotting. Cytosol and mitochondria fractionations were prepared by the cytosol/mitochondria fractionation kit (Biovision), according to the manufacturer protocol. Cytoskeleton precipitation and G-actin/F-actin assay were performed by the G-actin/F-actin in vivo assay biochem kit (Cytoskeleton, Inc.)

Subcellular localization of BAD proteins was determined by immunoblotting with anti-BAD antibody and quantified by the ImageJ program and/or by IRDye with Li-cor Odyssey imaging system. At each time point, the sum of BAD proteins in the cellular fractions (e.g., cytoskeleton plus cytosol versus mitochondria; or cytoskeleton versus cytosol), was calculated as 100%. To calculate the percentage of IKK-phosphorylated BAD in total BAD, $Ser^{26}$-phosphorylated BAD proteins were immunoprecipitated with anti-$Ser^{26}$ antibody and immunoblotted with anti-BAD antibody and quantified by the ImageJ program and/or by IRDye with Odyssey imaging system. BAD proteins from the same amount of total cell extracts were detected with anti-BAD antibody and calculated as 100%.

Actin Filament Binding Assay and G-Actin Monomer GST Protein Pulldown.

The actin filament binding protein spin-down assay kit was purchased from Cytoskeleton Inc. and performed according to the manufacturer protocol. Briefly, purified G-actin monomers (5 µg) were polymerized by incubating at room temperature for 1 hour; then, purified GST-BAD proteins (2 µg) were added to the reaction mixture and the mixture was incubated for 30 minutes at room temperature. F-actin filament-associated GST-BAD proteins were obtained by ultracentrifugation for 20 minutes and subjected to immunoblotting assay. F-actin filament binding GST-Cofilin was used as positive control.

The interaction between G-actin monomers and BAD was detected by GST protein pulldown assay. Briefly, purified G-actin monomers were incubated with purified GST-BAD, GST (negative control), or GST-Cofilin (positive control) separately in vitro. GST-fusion protein-associated G-actin was precipitated by Glutathione sepharose beads and analyzed by immunoblotting assay with corresponding antibodies, as indicated in the figure legends.

Immunofluorescence Staining, Ground State Depletion (GSD) Microscopy, and Proximity Ligation Assay.

Immunofluorescence staining was performed as previously described (12). Images were captured using Leica SP5 Tandem Scanner Spectral 2-Photon Confocal equipped with Leica LAS-AF software. The fluorescence intensity was quantified by single line scan analysis using the ImageJ program.

GSD imaging was visualized by Leica GSD/TIRFM ground stat depletion super-resolution microscope using 160×/1.43 oil HCX PL APO objective and Andor-DU897_BV-7849 camera.

Proximity ligation assay was performed with Duolink in situ fluorescent detection reagents (Sigma). Images were taken by Leica SP5 Tandem Scanner Spectral 2-Photon Confocal, and quantified by the ImageJ program. At least five different fields of each sample were randomly chosen for analysis.

Cell Culture.

WT and Bad-deficient MEFs were described previously (12). Cells were grown in Dulbecco's modified Eagle's medium (DMEM) supplemented with 10% fetal bovine serum, 2 mM glutamine, 100 U/ml penicillin, and 100 µg/ml streptomycin.

For isolation and culture of primary hepatocytes, mice were perfused with perfusion medium (Invitrogen) and digested with 100 U/ml collagenase. The collected primary hepatocytes were cultured in DMEM/F-12 medium (1:1 mix of DMEM and Ham's F-12 medium) containing 10% FBS, 1× insulin, transferrin, and 10 µg/ml EGF. For preparing primary murine macrophages, whole bone marrow was harvested from femur and tibia bones. After removing the mixed red blood cells by ACK lysis buffer, cells were re-suspended in BMDM conditional medium containing 20% FBS, 14.3 µM ß-mercaptoethanol, and 20 ng/ml M-CSF. For isolation and culture of primary thymocytes, the murine thymuses were extracted aseptically and collected in RPMI 1640 medium. Single cell suspensions of the thymuses were prepared by pressing the organs through a 70 µm nylon cell strainer and then cells were cultured in RPMI 1640 medium with 10% FBS. For isolation of primary splenocytes, spleens were extracted from mice and gently pressed through 70 µm nylon cell strainer. The mixed red blood cells were removed by ACK lysis buffer. After centrifugation at 800×g for 3 minutes, the pellet of splenocytes was re-suspended in DMEM supplemented with 10% fetal bovine serum.

Statistical Analysis.

Cell apoptosis, Casp-3 assay, quantitative real-time PCR analysis, and serology measurement between two groups were expressed as the means plus and minus the standard deviation. Statistical analysis was conducted using two-tailed Student's t test. Mouse survival curves were constructed using the Kaplan-Meier product limit estimator and compared using the log rank (Mantel-Cox) test. $P<0.05$ was considered to be significant in all experiments.

Example 1—TNFα Activates BAD

During the development of embodiments of the technology provided herein, experiments were conducted to determine how cytotoxic dose TNFα activates BAD despite concurrent IKK activation. In particular, data were collected in experiments using WT and Ikkß-deficient fibroblasts stimulated with a non-cytotoxic dose of TNFα. After stimulation with a non-cytotoxic dose of TNFα, a small amount of non-phosphorylated BAD translocated to mitochondria in Ikkß-deficient MEFs (FIG. 1D; middle panel, ~10%, lane 12). Under the same conditions, a similar amount of BAD was phosphorylated by IKK in WT fibroblasts (FIG. 1D, ~9%, lane 3) and there was no detectable BAD mitochondrial translocation (FIG. 1D), indicating that all BAD proteins that could translocate to mitochondria are phosphorylated by IKK. In response to cytotoxic dose TNFα, however, substantial amount of non-phosphorylated BAD translocated to mitochondria in Ikkß-deficient MEFs (FIG. 1E; middle panel, ~40%, lane 12). Under the same conditions, a significant amount of non-phosphorylated BAD also translocated to mitochondria in WT fibroblasts (FIG. 1E; ~22%, lane 12), even though the amount of IKK-phosphorylated BAD was more than twice the amount of IKK-phosphorylated BAD in non-cytotoxic dose TNFα-treated fibroblasts (FIG. 1E; ~21%, lane 3 versus FIG. 1D, ~9%, lane 3). The total BAD (e.g., sum of phosphorylated and non-phosphorylated BAD) in WT fibroblasts was similar to the amount of BAD translocated to mitochondria in Ikkß-deficient MEFs (43% (22%+21%) versus 40%), indicating that cytotoxic dose TNFα mobilizes more cytosolic BAD than IKK has the capacity to phosphorylate. Indeed, a cytotoxic dose of TNFα was unable to induce translocation of a phosphomimetic BAD mutant (e.g., BAD comprising a S26D substitution (BAD(S26D)), which produces a mutant protein that mimics a phosphorylated form of WT BAD that interacts with 14-3-3 and thus sequesters BAD in the cytosol) to mitochondria (FIG. 1F) to induce apoptosis (FIG. 1G).

Conversely, non-cytotoxic dose TNFα induced translocation of a constitutively non-phosphorylated BAD mutant (e.g., BAD comprising a S26A substitution (BAD(S26A)), which interacts with mitochondrial BCL-xL) to mitochondria (FIG. 1H) to induce apoptosis (FIG. 1I). These results indicated that cytotoxic dose TNFα increased the amount of cytosolic BAD available for translocation to the mitochondria to an amount that exceeds IKK phosphorylation capacity.

Example 2—BAD Interacts with F-Actin

During the development of embodiments of the technology described herein, experiments were conducted to identify cellular reservoirs of BAD that release BAD into the cytosol upon stimulation with cytotoxic dose TNFα. In particular, data collected from super-resolution, ground state depletion (GSD) microscopy revealed that BAD directly associated with F-actin in cytoskeleton actin stress fibers, which is a previously unknown subcellular reservoir for BAD (FIG. 2A). Consistently, sedimentation equilibrium analysis showed that BAD interacted with F-actin in the actin filament, but BAD did not interact with G-actin monomer in solution. These data indicated that the interaction of BAD with F-actin is facilitated by polymer actin stress fibers. Furthermore, proximity ligation assay revealed that BAD selectively interacted with F-actin in the actin stress fibers (FIG. 2B), but BAD did not interact with tubulin or vimentin, which are markers of microtubules and intermediate cytoskeleton filaments, respectively.

Data further indicated that BAD dissociated from F-actin rapidly and the amount of BAD associated with F-actin was significantly reduced by cytotoxic dose TNFα (FIG. 2B). Cell fractionation assays also showed that non-cytotoxic dose TNFα slightly released BAD (FIG. 2C, top panel, ~12%; 4 hours) from the cytoskeleton into the cytosol; data further indicated that released BAD was phosphorylated by IKK (FIG. 2C, middle panel). By contrast, cytotoxic dose TNFα significantly released BAD (FIG. 2C, top panel, ~50%; 4 hours) to cytosol; data further indicated that approximately half of the released BAD (~22%) was phosphorylated by IKK (FIG. 2C, middle panel). The amount of the remaining non-phosphorylated BAD (~28%) was similar to the amount of BAD measured to translocate into mitochondria under the same experimental conditions (FIG. 1E). Cytotoxic dose TNFα induced similar levels of WT BAD and BAD(S26D) to be released from the cytoskeleton into the cytosol. Unlike WT BAD, however, the phospho-mimetic BAD(S26D) mutant did not translocate to mitochondria to induce apoptosis (FIGS. 1, F and G), further indicating that cytotoxic dose TNFα-released BAD exceeds IKK phosphorylation capacity. These data indicated that BAD is sequestered in the cytosol by two interconnected mechanisms: 1) non-phosphorylated BAD is sequestered by F-actin in actin stress fibers at the cytoskeleton; 2) after being released from the F-actin fibers, only phosphorylated BAD is sequestered by the 14-3-3 proteins in cytosol. Upon treatment with non-cytotoxic dose TNFα, a small percentage of BAD is released and is completely phosphorylated by IKK, thereby sequestering in the cytosol the small percentage of BAD released from the F-actin. By contrast, cytotoxic dose TNFα-released BAD exceeds IKK phosphorylation capacity, thereby triggering apoptosis due to the translocation of BAD into mitochondria.

Example 3—TNFα Promotes Depolymerization of Actin Stress Fibers at Cytoskeleton

During the development of embodiments of the technology described herein, experiments were conducted to determine the mechanism by which cytotoxic dose TNFα induces substantial BAD release from cytoskeleton to cytosol. In particular, experiments were conducted to analyze the effect of cytotoxic dose TNFα on actin stress fiber stability (e.g., polymerization and depolymerization). Data collected from confocal fluorescence microscopy indicated that cytotoxic dose TNFα induced significant depolymerization of actin stress fibers (FIG. 2D). Consistently, the ratio of G-actin to F-actin, an index of actin stress fiber depolymerization, was significantly increased by cytotoxic dose TNFα. Loss of TNF-$R_1$ but not caspase 8 inhibited the depolymerization of actin stress fibers, indicating that the depolymerization effect is mediated by TNF-$R_1$ signaling, rather than the consequence of apoptosis. Cytotoxic dose TNFα-induced BAD mitochondrial translocation and apoptosis were significantly reduced by actin stress fiber polymerization stabilizers such as Jasplakinolide or sphingosine-1-phosphate. Conversely, non-cytotoxic dose TNFα induced BAD mitochondrial translocation and apoptosis in the presence of actin stress fiber polymerization inhibitors like cytochalasin D or latrunculin B. Thus, cytotoxic dose TNFα induces massive depolymerization of actin stress fibers, thereby releasing substantial BAD from the cytoskeleton to cytosol to circumvent IKK-mediated inhibition.

Example 4—Cytotoxic Dose TNFα Inactivates RhoA

Rho subfamily GTPase member RhoA promotes formation of actin stress fibers at the cytoskeleton (15). Experiments were conducted during the development of embodiments of the technology to test inactivation of RhoA by cytotoxic dose TNFα. Although RhoA was reported to be activated by TNFα through transactivation of EGFR signaling (16), experiments conducted during the development of embodiments of the technology described herein indicated that TNFα regulated RhoA in a biphasic manner with an early inactivation phase and a late activation phase (FIG. 2E). In comparison to non-cytotoxic dose TNFα, cytotoxic dose TNFα-induced early inactivation of RhoA was stronger and sustained (FIG. 2E), and was followed by a much slower late phase activation of RhoA (FIG. 2E). This regulation of RhoA is specific, since data indicated that there was no detectable difference between a non-cytotoxic and a cytotoxic dose of TNFα in activation of another Rho subfamily GTPase member, Cdc42, which regulates actin polymerization at the plasma membrane (17).

Figure 2:
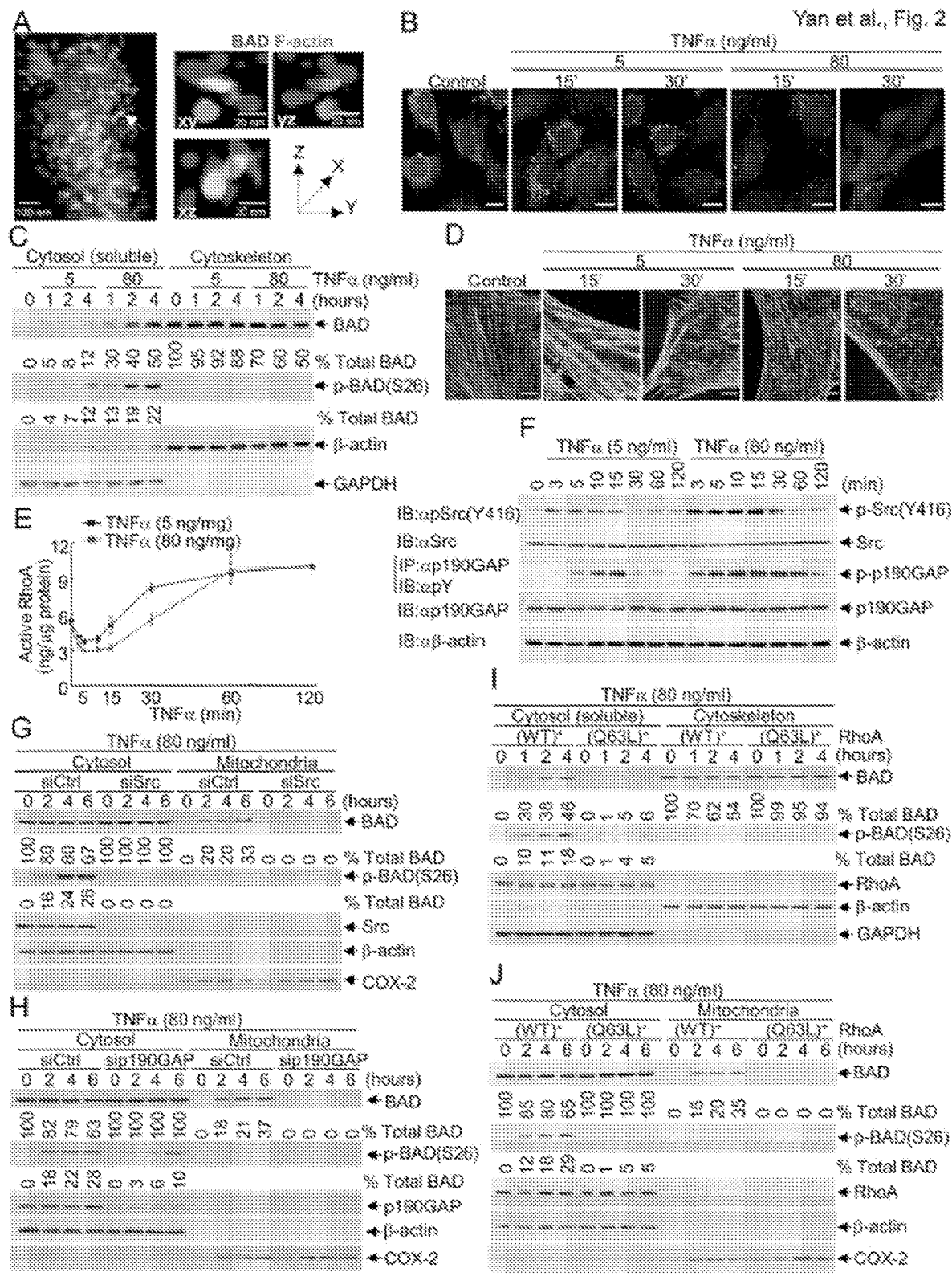

RhoA activity is inactivated by a specific Rho GTPase activating protein (p190GAP) (18), whose activity is stimulated by Src-mediated tyrosine phosphorylation (19); and RhoA activity is activated by GTPase exchange factor H1 (GEF-H1), whose activity is stimulated by ERK (16). TNFα is known to induce $Src^{Y416}$ autophosphorylation and activation (20). Cytotoxic dose TNFα induced more phosphorylation of Src at $Tyr^{416}$ than non-cytotoxic dose TNFα (FIG. 2F, ~8-fold versus ~5-fold), resulting in stronger and prolonged tyrosine phosphorylation of p190GAP (FIG. 2F). Under the same conditions, cytotoxic dose TNFα induced slightly increased ERK activation and produced no significant change in GEF-H1 activation when compared to non-cytotoxic dose TNFα. These data indicated that preferential activation of the Src-p190GAP pathway by cytotoxic dose TNFα leads to stronger and sustained early phase inactivation of RhoA. Consistently, knockdown of Src or p190GAP significantly reduced cytotoxic dose TNFα-induced depolymerization of actin stress fibers to a level of depolymerization that was similar to depolymerization observed in non-cytotoxic dose TNFα-treated WT fibroblasts, in which all BAD released from cytoskeleton was phosphorylated by IKK (FIG. 2C), thereby blocking cytotoxic dose TNFα-induced BAD mitochondrial translocation (FIGS. 2, G and H) and apoptosis. More importantly, ectopic expression of a constitutively active RhoA(Q63L) mutant (21) but not WT RhoA in RhoA-deficient MEFs significantly inhibited cytotoxic dose TNFα-induced massive depolymerization of actin stress fibers (FIG. 2I) and BAD mitochondrial translocation (FIG. 2J), as well as apoptotic cell death. Thus, in comparison to non-cytotoxic dose TNFα, cytotoxic dose TNFα induces profound early phase inactivation of RhoA by stimulating stronger and sustained Src-dependent activation of p190GAP, resulting in massive depolymerization of actin stress fibers to release substantial BAD to cytosol to trigger apoptosis.

Example 5—BAD Mediates TNFα Cytotoxicity in Disease Pathology

Figure 3:
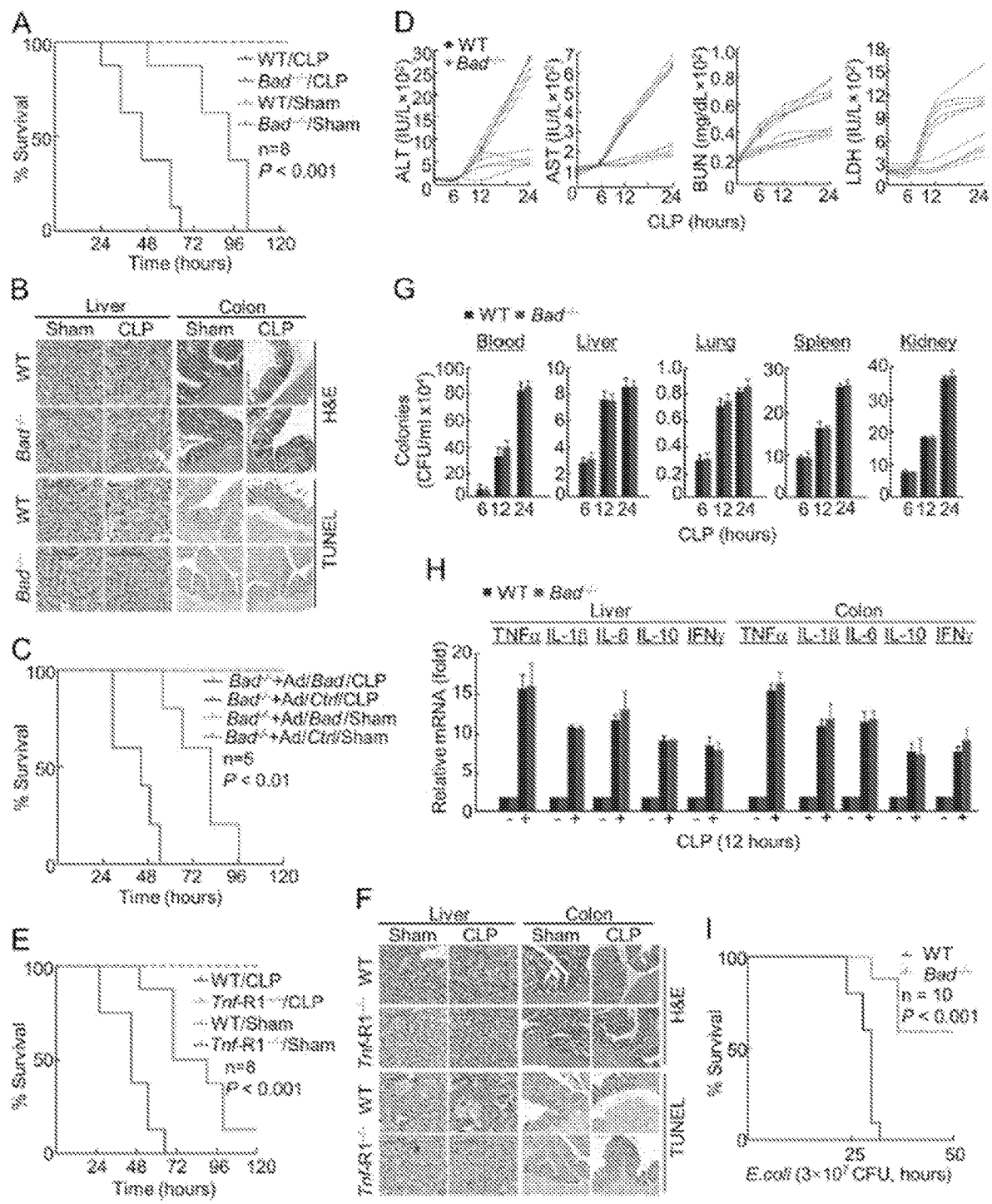

TNFα cytotoxicity has a crucial role in the pathologies of many inflammatory and infectious diseases (13, 14) including but not limited to severe sepsis (22, 23). During the development of embodiments of the technology provided herein, experiments were conducted to determine the pathological relevance of BAD-mediated TNFα cytotoxicity. In particular, data were collected from experiments performed using a cecal ligation and puncture (CLP) murine model of severe sepsis (24). In the CLP model, polymicrobial infection of the abdomen causes bacteremia and a systemic inflammatory response that results in multi-organ damage and mortality. Under conditions of the high-grade sepsis induced by CLP, WT littermates started to die around 24 hours (FIG. 3A), as reported previously (24), and had significant liver and colon damage accompanied with massive apoptosis (FIG. 3B). By contrast, Bad-deficient mice were significantly protected from polymicrobial infection-induced organ damage and mortality (FIGS. 3A and 3B). Reconstitution of Bad-deficient mice with WT Bad via adenoviral infection restored the sensitivity to polymicrobial infection-induced mortality (FIG. 3C). These data indicated that loss of BAD, but not other potential alterations in Bad-deficient mice, is responsible for the protection against polymicrobial infection-induced organ damage and mortality. Consistently, Bad-deficient mice had significantly reduced serum concentrations of several tissue damage markers including ALT (liver), AST (liver, heart and muscle), BUN (kidney), and LDH (lung and general damage) when compared to their WT littermates (FIG. 3D). Tnf-R1-deficient mice were significantly protected from mortality (FIG. 3E) and tissue damage (FIG. 3F), indicating that polymicrobial infection induces mortality and tissue damage in a TNFα signaling-dependent manner, consistent with previous reports (25). Interestingly, WT and Bad-deficient mice had a similar bacterial load in blood, liver, spleen, kidney, and lung (FIG. 3G) and comparable levels of inflammatory and anti-inflammatory cytokines in liver and colon (FIG. 3H), indicating that loss of BAD confers disease tolerance to severe sepsis without directly affecting bacterial burden, consistent with previous reports that cytotoxic TNFα impairs disease tolerance in several infectious diseases (1, 26-28). Loss of BAD also significantly reduced tissue damage and mortality induced by interperitoneally infused lethal dose *E. coli* (FIG. 3I) and interperitoneally infused lethal dose lipopolysaccharide (LPS; also known as endotoxin) (FIG. 13A to 13F). These data indicated that BAD mediates TNFα cytotoxicity in severe sepsis.

Example 6—BAD Mediates Pro-Apoptotic Activity in Infection

During the development of embodiments of the technology described herein, experiments were conducted to test whether polymicrobial infection uses the same mechanism as cytotoxic dose TNFα to stimulate BAD pro-apoptotic activity. Indeed, data collected during the experiments indicated that polymicrobial infection induced substantial BAD release from cytoskeleton to cytosol (FIG. 4A, upper panel, ~66%; 12 hours) and that only half of released BAD was phosphorylated (FIG. 4A, middle panel, ~35%, 12 hours). Consistently, polymicrobial infection induced significant translocation of non-phosphorylated BAD to mitochondria under similar conditions (FIG. 4B). Like cytotoxic dose TNFα, polymicrobial infection induced comparable IKK activation in the livers of WT littermate and Bad-deficient mice (FIG. 4C). Similar results were obtained with interperitoneally infused lethal dose *E. coli* (FIG. 14A to 14C) or LPS (FIG. 14D and 14E). Polymicrobial infection-induced BAD release from cytoskeleton and mitochondrial translocation were blocked in Tnf-R1-deficient mice (FIGS. 4D and 4E), indicating that TNFα stimulates BAD pro-apoptotic activity in polymicrobial infection. Interestingly, BAD mitochondrial translocation was also well correlated with epithelium damage associated with massive apoptosis in human colon tissue specimens of patients having bowel perforation of ulcerative colitis accompanying severe sepsis (FIG. 4F), indicating the potential relevance of BAD-mediated organ damage in severe sepsis patients. Taken together, our results indicate that polymicrobial infection via TNFα stimulates BAD pro-apoptotic activity despite concurrent activation of IKK, resulting in multi-organ damage and mortality (FIG. 4G).

Example 7—High Dose TNFα Induces Apoptosis in a BAD-Dependent Manner

Primary WT and Bad-deficient hepatocytes, thymocytes, macrophages, and splenocytes, as well as immortalized embryonic fibroblasts (MEFs) were treated with or without 5 ng/ml or 80 ng/ml TNFα, respectively, for 12 hours. Caspase 3 activity was determined. Data are means±s.d. and represent three individual experiments. **, $P<0.01$, as analyzed by two-tailed Student's t test (FIG. 5A).

WT and TnfR1-deficient embryonic fibroblasts were treated with or without 5 ng/ml or 80 ng/ml TNFα for 12 hours. Apoptotic cells were determined by Annexin V and propidium iodide (PI) staining, followed by flow cytometric analysis. Inlet, immunoblotting analysis of TNF-$R_1$ using anti-TNF-$R_1$ antibody. ß-actin was used as control (FIG. 5B).

Primary hepatocytes (FIG. 5C and 5D) and immortalized fibroblasts (FIG. 5E and FIG. 5F) were treated with various dosages of TNFα for 4 hours (FIG. 5C and FIG. 5F) or with 80 ng/ml TNFα for various times (FIG. 5D and FIG. 5E), as indicated. Cell extracts were separated into cytosol and mitochondrial fractions. Subcellular localizations of BAD and IKK-phosphorylated BAD[pBAD(S26)] were determined. ß-actin, BCL-xL and COX-2 were used as cytosol and mitochondrial markers, respectively. The results represent three individual experiments with similar results.

WT fibroblasts were treated with or without 80 ng/ml TNFα for 12 hours and the co-localization of BAD with mitochondria was analyzed by immunofluorescence staining using anti-BAD antibody, MitoTracker and DAPI (4',6-diamidino-2-phynylindole) (FIG. 5G and FIG. 5H). Image was taken with confocal microscopy. Scale bars in FIG. 5G represent 5 µm. Co-localization of BAD with mitochondrial was quantified by the ImageJ program and determined by Pearson's correlation coefficient. The results are presented as means±s.d. and represent three individual experiments; **, P<0.01, as analyzed by two-tailed Student's t test (FIG. 5H).

Primary WT and Bad-deficient hepatocytes were treated with or without 5 ng/ml or 80 ng/ml TNFα for various times as indicated. Total RNA was extracted for quantitative real-time PCR analysis with different primers specifically for cIAP2, IßBα and IL-6 (FIG. 5I).

Example 8—Cytotoxic and Non-Cytotoxic Dose TNFα Utilize Different Mechanisms to Induce Apoptosis WT, Jnk1-deficient (FIG. 6A), or Casp-8-deficient (FIG. 6B) fibroblasts were infected with or without Ad/IκBα(AA) (100 moi), followed by treatment with or without 5 ng/ml or 80 ng/ml TNFα for various times, as indicated. Apoptotic cells were determined as described in Example 7 (see, e.g., FIG. 5B).

Figure 6:
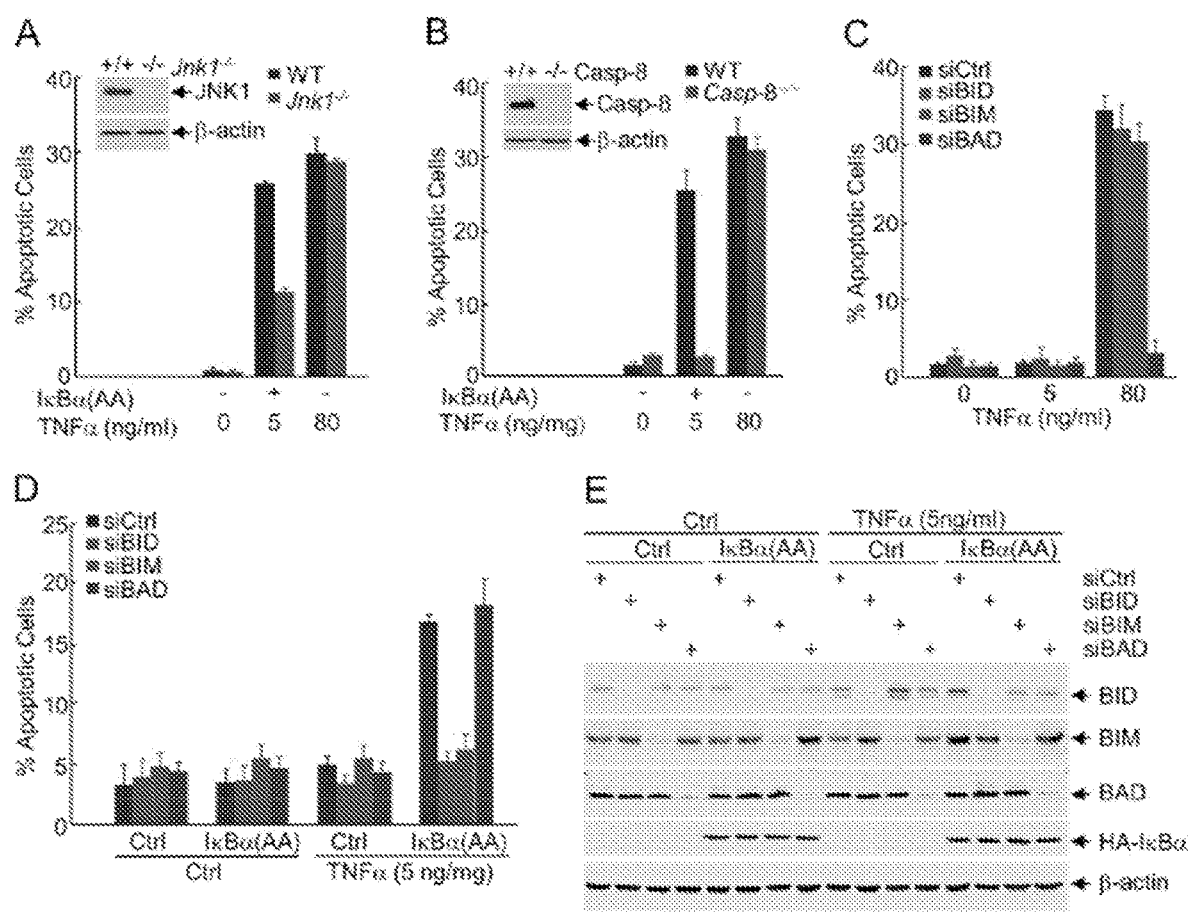

WT fibroblasts were transfected with scramble siRNA (siCtrl), siBID, siBIM, or siBAD, followed by infection with or without Ad/IκBα(AA) (100 moi) (FIG. 6C to FIG. 6E). Cells were treated with or without 5 ng/ml or 80 ng/ml TNFα, as indicated in the figures. Apoptotic cells were determined as described in Example 7 (see, e.g., FIGS. 5C and 5D). Expression levels of BID, BIM, BAD, HA-IκBα and ß-actin were determined by immunoblotting analysis using corresponding antibodies (FIG. 6E).

Example 9—BAD(S26D) and BAD(S26A) Mutants Act as Phosphor-Mimetic and Constitutively Non-Phosphorylated Mutants Bad-deficient fibroblasts were transfected with WT BAD, BAD(S26D) mutant (FIG. 7A), or BAD(S26A) mutant (FIG. 7B), followed by treatment with or without 80 ng/ml (FIG. 7A) or 5 ng/ml (FIG. 7B) TNFα for various times, as indicated. The associations between WT or mutant BAD and 14-3-3 or BCL-xL were analyzed by immunoprecipitation with anti-14-3-3 or anti-BCL-xL antibody, followed by immunoblotting with anti-BAD or anti-phospho-BAD antibody, respectively. IKK-mediated BAD phosphorylation, expression levels of BAD, 14-3-3 and, BCL-xL were determined as control.

Example 10—BAD is Sequestered at Cytoskeleton Through Selective Interaction with F-Actin and Released to Cytosol by Cytotoxic Dose TNFα Independently of its Phosphorylation Status WT fibroblasts were double immunofluorescence stained with anti-BAD antibody (red) and phalloidin (actin filament marker; green) and analyzed with super-resolution microscopy based on Ground State Depletion program (FIG. 8A; scale bar, 1 µm).

Purified G-actin monomers were incubated with purified GST, GST-Cofilin or GST-BAD protein separately in vitro (FIG. 8B). An aliquot of the mixture was subjected to ultracentrifugation to detect the interaction between GST-fusion proteins and F-actin in actin filaments. In parallel, another aliquot of the mixture was used in GST pulldown assay to detect the interaction between GST-fusion proteins and G-actin monomers. GST-fusion proteins and actin were detected by immunoblotting with anti-GST and anti-actin antibodies, respectively. A third aliquot of the mixture was used as Input (FIG. 8B).

WT fibroblasts were treated with or without 80 ng/ml TNFα for various times as indicated (FIG. 8C). Cytosol fractions were separated from cell extracts by ultracentrifugation. Proteins association between G-actin and BAD were analyzed by immunoprecipitation with anti-actin antibody, followed by immunoblotting with anti-BAD antibody. The associations between G-actin and Cofilin and between 14-3-3 and phosphorylated-BAD were used as positive controls. IKK-mediated BAD phosphorylation, expression levels of BAD, Cofilin, G-actin and 14-3-3 were determined (FIG. 8C).

Negative controls are shown for proximity ligation assay of FIG. 2B in which WT fibroblasts were stained with anti-BAD antibody only, anti-ß-actin antibody only, or no primary antibodies, as indicated (FIG. 8D). Nuclei were detected by DAPI. Scale bars represent 5 µm.

Proximity ligation assay was performed and imaged as described in FIG. 2B but with anti-BAD and anti-Tubulin (FIG. 8E) or anti-BAD and anti-Vimentin (FIG. 8F) instead. The interactions between Tubulin and MAP1ß (FIG. 8E) or interaction between Desmoplakin and Vimentin (FIG. 8F) were detected with corresponding antibodies as indicated and used as positive controls.

ImageJ was used to quantify co-localization of BAD with actin by proximity ligation assay of FIG. 2B (FIG. 8G). Data are means±s.d. and represent three individual experiments. *, P<0.05, as analyzed by two-tailed Student's t test.

Bad-deficient fibroblasts were transfected with WT BAD, BAD(S26D), or BAD(S26A) mutant separately, followed by treatment with or without 80 ng/ml TNFα for various times, as indicated (FIG. 8H). Cell extracts were separated into cytosol and cytoskeleton fractions by ultracentrifugation. Subcellular localizations of BAD and IKK-phosphorylated BAD were analyzed by immunoblotting. The levels of BAD and IKK-phosphorylated BAD were determined and quantified. The results represent two individual experiments with similar results.

Example 11—Cytotoxic Dose TNFα-Induced Depolymerization of Actin Stress Fibers Depends on TNF-R$_1$ but not Casp-8

WT (FIG. 9A), TnfR1-deficient (FIG. 9B), and Casp-8-deficient (FIG. 9C) fibroblasts were stimulated with 5 ng/ml or 80 ng/ml TNFα for 15 or 30 min, as indicated. Cytosol and cytoskeleton fractions were separated by ultracentrifugation. G-actin and F-actin were detected by immunoblotting with anti-ß-actin antibody. Cells treated with Cytochalasin D (CyD; 1 µg/ml; 1 h) were used as positive control (FIG. 9A). The results were quantified by the ImageJ program and/or IRDye fluorescence analyzed by Odyssey Imager. The data represent two to three individual experiments with similar results.

Example 12—The Ability of TNFα to Induce BAD Mitochondrial Translocation and Apoptosis is Inhibited by Polymerization but Promoted by Depolymerization of Actin Stress Fibers WT and Bad-deficient fibroblasts were pre-treated with 30 nM Jasplakinolide (FIG. 10A and FIG. 10B), 5 µM Sphingosine-1-phosphate (S1P) (FIG. 10C and FIG. 10D) or DMSO (control) for 1 hour, followed by stimulation with or without 80 ng/ml TNFα for various times, as indicated. Cell extracts were separated into cytosol and mitochondrial fractions. Subcellular localizations of BAD and IKK-phosphorylated BAD were determined. ß-actin, BCL-xL, and COX-2 were used as control (FIG. 10A and FIG. 10C). Apoptotic cells were identified by Annexin V and PI staining, followed by flow cytometric analysis. Data are as means±s.d. **, P<0.01, as analyzed by two-tailed Student's t test (FIG. 10B and FIG. 10D).

WT and Bad-deficient fibroblasts were pretreated with 1 µg/ml Cytochalasin D (FIG. 10E and FIG. 10F), 2.5 µg/ml Latrunculin B (FIG. 10G and FIG. 10H), or DMSO (control) for 1 hours, followed by stimulation with or without 5 ng/ml or 80 ng/ml TNFα for 4 hours (FIG. 10E and FIG. 10G) or 12 hours (FIG. 10F and FIG. 10H). Cell extracts were separated into cytosol and mitochondrial fractions. Subcellular localizations of BAD and IKK phosphorylated BAD were determined. ß-actin, BCL-xL, and COX-2 were used as control (FIG. 10E and FIG. 10G). Apoptotic cells were identified by Annexin V and PI staining, followed by flow cytometric analysis. Data are means±s.d. and represent three individual experiments. **, P<0.01, as analyzed by two-tailed Student's t test (FIG. 10B, FIG. 10D, FIG. 10F, and FIG. 10H).

Figure 11:
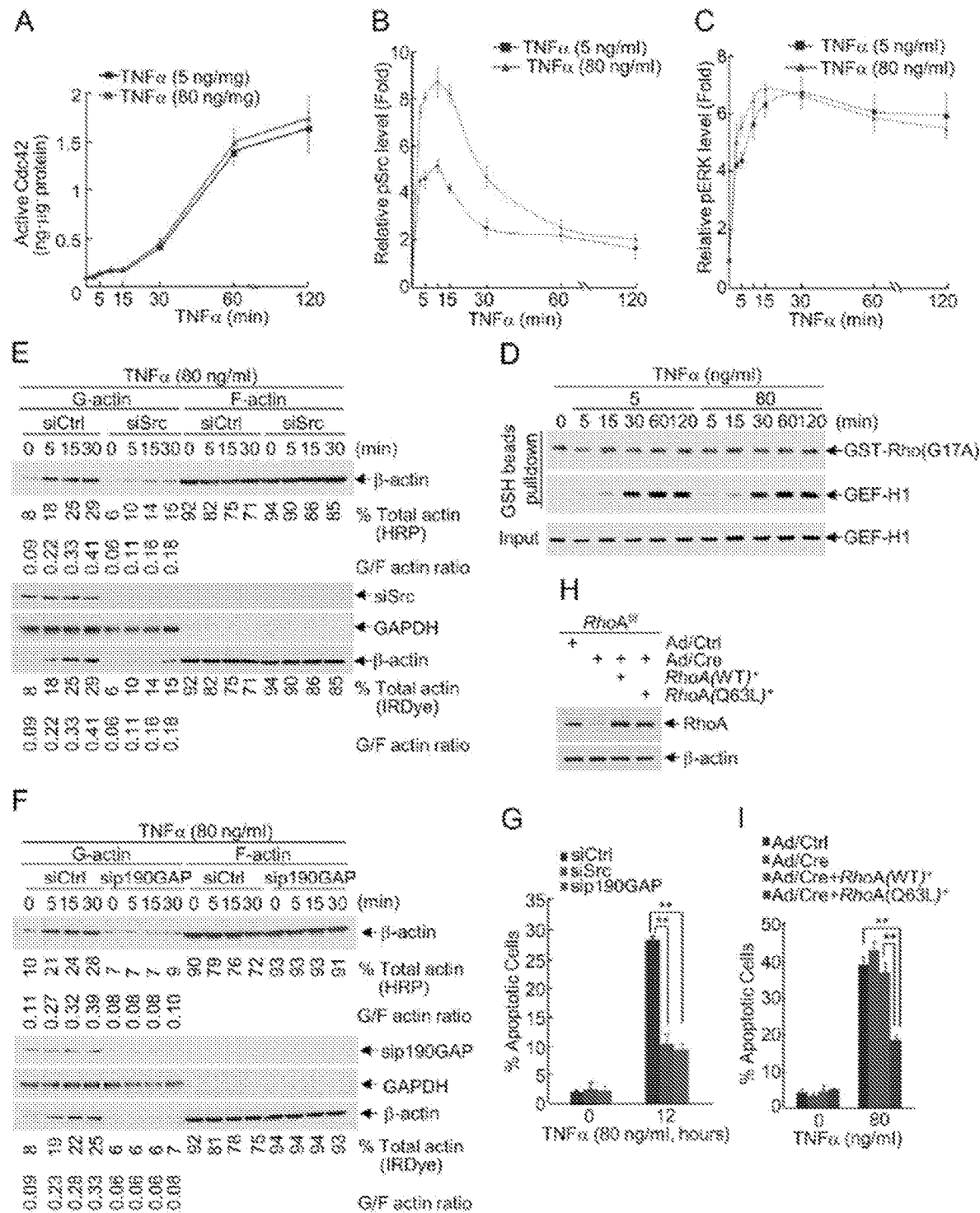

Example 13—Cytotoxic Dose TNFα Preferentially Activates Src-p190GAP Pathway and Selectively Induces an Early-Phase Inactivation of RhoA and Subsequent Depolymerization of Actin Stress Fibers WT fibroblasts were treated with or without 5 ng/ml or 80 ng/ml TNFα for various times as indicated. Cell extracts were subjected to the G-LISA Cdc42 activation assay. Data are means±s.d. (FIG. 11A). Phospho-Src, phospho-ERK, and expression levels of Src, ERK and ß-actin were determined by immunoblotting. The phospho-proteins relative to basal level (without TNFα treatment) were quantitatively analyzed by ImageJ program. Data are means±s.d. and represent three individual experiments (FIG. 11B and FIG. 11C). Active GEF-H1 was detected (see Materials and Methods). Expression level of GEF-H1 and the input GSTRho(G17A) were detected with immunoblotting (FIG. 11D).

WT fibroblasts were transfected with scramble siRNA (siCtrl) (FIG. 11E to FIG. 11G), siSrc (FIG. 11E) or sip190GAP (FIG. 11F and FIG. 11G), and treated with or without 80 ng/ml TNFα for various times as indicated. Cytosol and cytoskeleton fractions were separated by ultracentrifugation (FIG. 11E, FIG. 11F). G-actin and F-actin were detected by immunoblotting with anti-ß-actin antibody. Expressing level of Src (FIG. 11E) and p190GAP (FIG. 11F) was detected with corresponding antibodies, respectively. GAPDH were used as cytosol marker. The results were quantified by the ImageJ program and IRDye fluorescence analyzed by Odyssey Imager. Apoptotic cells were identified by Annexin V and PI staining, followed by flow cytometric analysis (FIG. 11G).

Primary RhoAf/f fibroblasts isolated from RhoA-deficient mice were infected with Ad/Ctrl or Ad/Cre (10 multiplicity of infection, moi) and transfected with or without expressing vector pcDNA3 encoding WT or the Q63L mutant of RhoA, followed by treatment with or without 5 ng/ml or 80 ng/ml TNFα for various times, as indicated. Expression levels of RhoA and ß-actin were detected with corresponding antibodies separately (FIG. 11H). Apoptotic cells were identified by Annexin V and PI staining, followed by flow cytometric analysis (FIG. 11I). Data in FIG. 11G and FIG. 11I are means±s.d. **, P<0.01, as analyzed by two-tailed Student's t test. All results represent two to three individual experiments with similar results.

Figure 12:
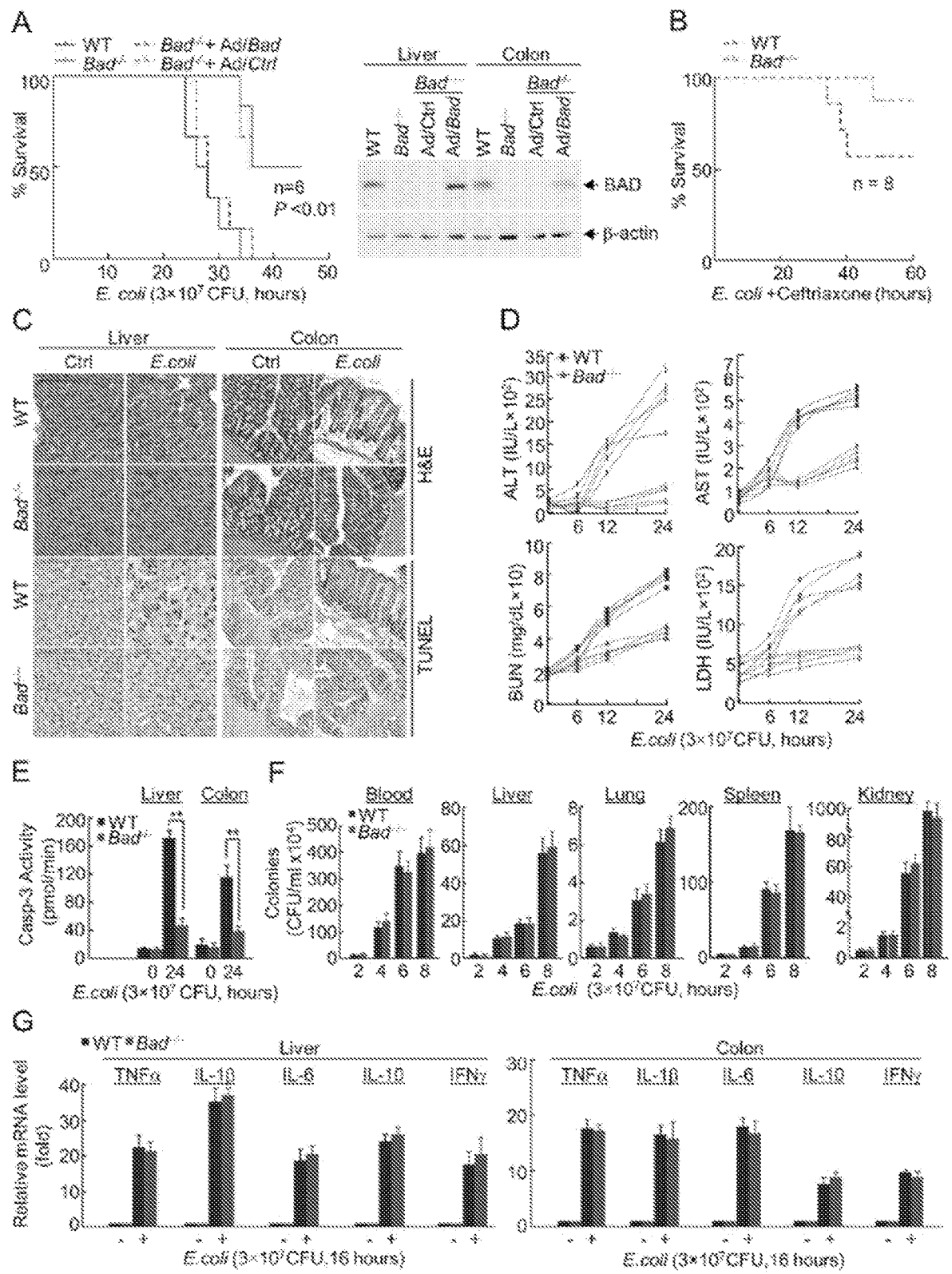
Figure 13:
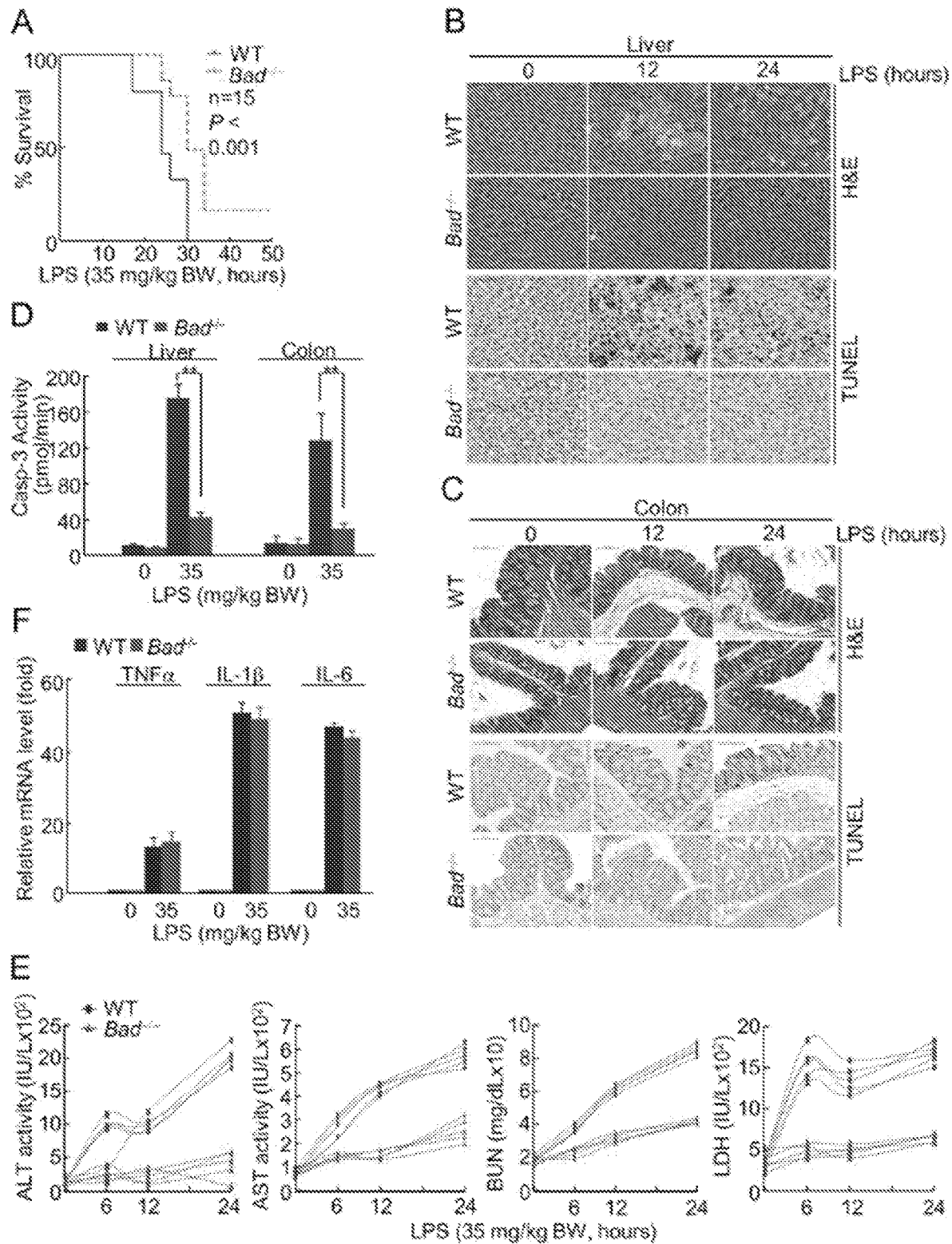
Figure 14:
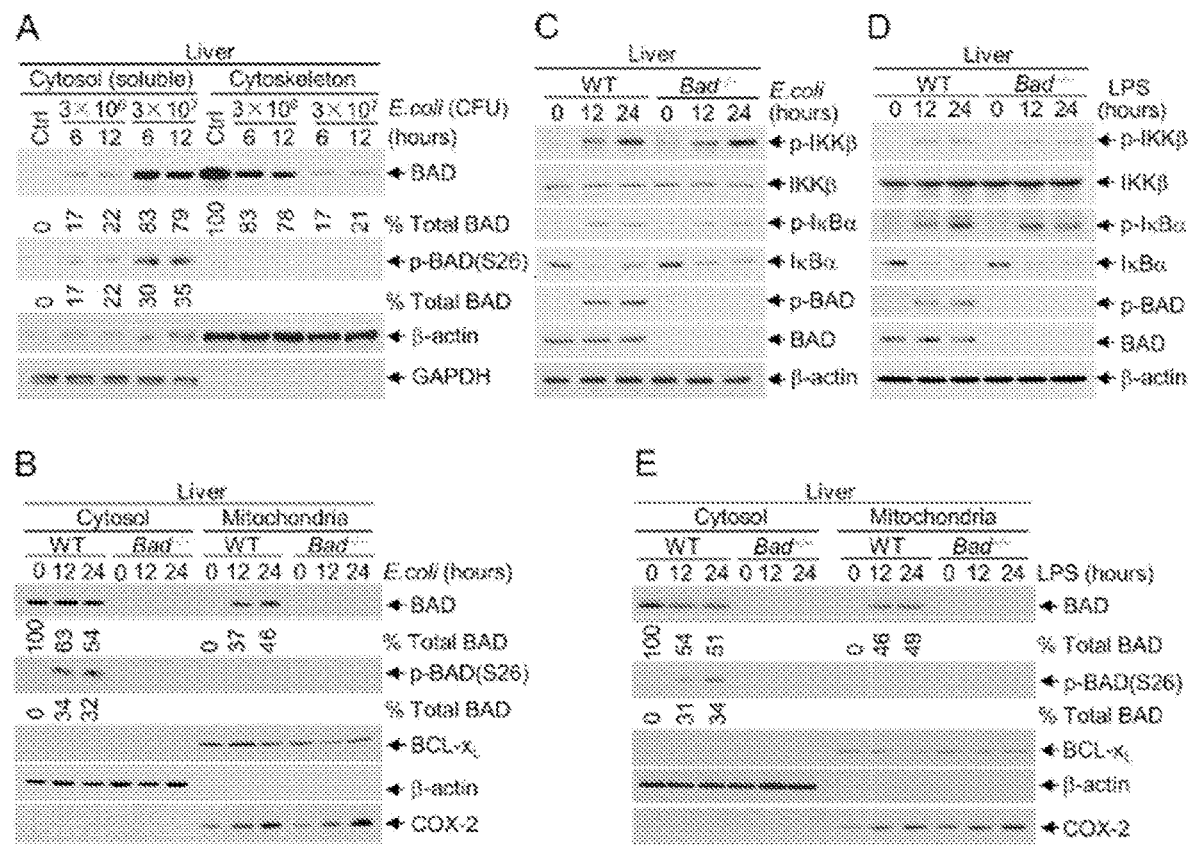

Example 14—Bad-Deficient Mice Were Protected from E. Coli Infusion-Induced Organ Damage and Mortality WT littermate and Bad-deficient mice were intraperitoneally (i.p.) injected with lethal E. coli ($3 \times 10^7$ CFU), without (FIG. 12A, FIG. 12C to FIG. 12G) or with (FIG. 12B) i.p injection with 50 µg/kg body weight of Ceftriaxone. Dying mice were pre-moved. The mortality rate was determined. P<0.01 (FIG. 12A), as analyzed by log rank (Mantel-Cox) test. No statistical significance for (FIG. 12B). The liver and colon tissues were extracted 24 hours after E. coli infection. Tissue damage of liver and colon and apoptosis of hepatocyte and epithelial cells were analyzed by haematoxylin and eosin (H&E) staining and TUNEL staining, respectively (FIG. 12C) and the relative Caspase 3 activity were analyzed (FIG. 12E). **, P<0.01, as determined by two-tailed Student's t test. Blood samples from the tail vein and other tissue samples were collected after E. coli infection at various times, as indicated. The serum was used for ALT, AST, BUN and LDH determination (FIG. 12D). Bacteria load in the circulation, liver, lung, spleen and kidney was analyzed by blood culture and Gram staining (FIG. 12F). Total RNA was extracted from the livers and colons 16 hours after E. coli infection for quantitative real-time PCR analysis with different primers specifically for TNFα, IL-16, IL-6, IL-10 and IFNγ (FIG. 12G). Data in (FIG. 12E to FIG. 14G) are means±s.d., the statistical significance was analyzed by two-tailed Student's t test. The results represent three individual experiments.

Example 15—Bad-Deficient Mice were Protected from LPS-Induced Organ Damage and Mortality WT littermate and Bad-deficient mice were intraperitoneally (i.p.) injected with lethal LPS (35 mg/kg body weight). Dying mice were pre-moved. The mortality rate was determined, P<0.001, as analyzed by log rank (Mantel-Cox) test (FIG. 13A). Liver and colon tissues were extracted for H&E staining and Tunnel staining (FIG. 13B and FIG. 13C). Caspase 3 activity analysis, **, P<0.01, as analyzed by two-tailed Student's t test (FIG. 13D). Blood and serum were collected from the tail vein for ALT, AST, BUN, and LDH detection (FIG. 13E). Total RNA were extracted from the liver for Real-time PCR analysis with different primers specifically for TNFα, IL-6, and IL-16 (FIG. 13F).

Example 16—E. coli and LPS Utilize the Same Mechanism as Cytotoxic Dose TNFα to Stimulate BAD Pro-Apoptotic Activity WT littermate and Bad-deficient mice were i.p. injected with non-lethal ($3 \times 10^6$ CFU) or lethal ($3 \times 10^7$ CFU) dose E.

coli for various times, as indicated (FIG. 14A to FIG. 14E). Liver extracts were fractionated into cytosol and cytoskeleton (FIG. 14A) or cytosol and mitochondria (FIG. 14B) by ultracentrifugation. Subcellular localizations of BAD and IKK-phosphorylated BAD were analyzed by immunoblotting (FIG. 14A). ß-actin, BCL-xL, and COX-2 were used as cytosol and mitochondria markers, ß-actin and GAPDH were used as cytosol and cytoskeleton markers, respectively (FIG. 14B). The levels of BAD and the percentage of IKK-phosphorylated BAD in total BAD were determined and quantified.

Phosphorylation of IKKß and IκBα, as well as expression levels of IκBα, IKKß, BAD, and ß-actin in total liver tissue extracts were analyzed (FIG. 14C).

WT littermate and Bad-deficient mice were i.p injected 35 mg/kg body weight of LPS. Dying animals were pre-removed and liver tissues extracts were used to either analyze IKK and NF-κB activation (FIG. 14D), as described in (FIG. 14C), or further separate into mitochondrial and cytosol fractions (FIG. 14E) to analyze BAD phosphorylation and mitochondrial translocation, as described in (FIG. 14B). All results represent three individual experiments with similar results.

Example 17—BAD Mitochondrial Translocation was Well Correlated with Epithelium Damage in Human Colon Tissue Specimens of Severe Sepsis Patients Three additional pairs of colon tissue specimens of patients having perforation of ulcerative colitis accompanying with severe sepsis were analyzed as described in FIG. 4F (FIG. 15A).

FIG. 15B shows results of quantifying localization of BAD with mitochondria in colon tissue specimens collected by surgical resection from patients having perforation of ulcerative colitis accompanying severe sepsis (see, e.g., FIG. 4F and FIG. 15A). SLZ: side-lesion-zone; FLZ: focal-lesion zone. Co-localization of BAD with mitochondria was determined by Pearson's correlation coefficient and quantitated by the ImageJ program. At least five different fields of each sample were randomly chosen for analysis. Data are means±s.d. *, P<0.05; **, P<0.01, as analyzed by two-tailed Student's t test.

Example 18—Quantification of Phosphorylated BAD Proteins

FIG. 15A to FIG. 15S show data collected from cells that were treated the same as indicated above each immunoblot image. The percentage of IKK-phosphorylated BAD in total BAD was determined by immunoprecipitation of Ser26-phosphorylated BAD with anti-Ser26 antibody in combination with immunoblotting with anti-BAD antibody, and quantified by the ImageJ program and/or IRDye fluorescence analyzed by Odyssey Imager. BAD in the total cell extracts were calculated as 100%.

FIG. 15T to FIG. 15W show data collected from mice that were treated the same as indicated above each immunoblot image. Liver tissues were extracted and the levels of BAD and IKK-phosphorylated BAD in different fractions were quantitated by the ImageJ program and IRDye fluorescence analyzed by Odyssey Imager. All results represent two to three individual experiments with same results.

Example 19—Blockade of TNFα by a Src Inhibitor

During the development of embodiments of the technology provided herein, experiments were conducted to control TNFα cytotoxicity through regulating TNFα-induced redistribution of BAD from cytoskeleton to cytosol. In particular, data were collected in experiments testing inhibitors of the Src protein.

Methods

In vitro kinase assay. To determine kinase activity, Src and IKKß phosphorylation were analyzed by immunoblotting. Briefly, MEFs were treated with inhibitor, followed with TNFα treatment as indicated in figure legends. Total cell lysate was prepared for western blotting analysis with antibodies specific for phosphor-Src, phosphor-IKKß, Src, IKKß, and ß-actin.

BAD Sub-Cellular Analysis.

BAD was identified in sub-cellular fractions by cellular fractionation and immunoblotting analysis. Cytosol and mitochondria fractionation was carried out by using the cytosol/mitochondria fractionation kit (Biovision) according to the manufacturer protocol. Using this method, the cytosol fraction also contains cytoskeleton. Cytosol and cytoskeleton fractionation was carried out by using the subcellular protein fractionation kit for cultured cells (Thermo) according to the manufacturer protocol. Using this method, the cytosol fraction also contains subcellular organelles including mitochondria. Subcellular localization of BAD proteins was determined by immunoblotting with anti-BAD antibody and quantified by the ImageJ program and/or IRDye with a Li-cor Odyssey imaging system. At each time point, the sum of BAD proteins in different fractions, either cytosol (containing cytoskeleton) versus mitochondria, or cytoskeleton versus cytosol, was calculated as 100%. To calculate the percentage of IKK-phosphorylated BAD in total cytoplasmic BAD, Ser26-phosphorylated BAD proteins were immunoprecipitated with anti-Ser26 antibody and immunoblotted with anti-BAD antibody and quantified by the ImageJ program and/or IRDye with an Odyssey imaging system. BAD proteins from the same amount of total cell extracts were detected with anti-BAD antibody and calculated as 100%.

In Vivo Experiments.

Wild type C57B6/J6 mice were maintained in a specific pathogen-free facility and housed on a 12:12-hour light/dark photoperiod at an ambient temperature of 22° C.±2° C. All animal experiments were conducted in accordance with the protocols approved by the Institutional Animal Care and Use Committee of the University of Chicago. 6-8 week old male mice were used for all of the experiments. The bacterial infusion model was performed by intraperitoneal (i.p.) injection of E. coli (ATCC 25922; 3×10$^7$ CFU). For the polymicrobial infection model, the CLP procedure was performed. The severity of CLP was adjusted to a high-grade sepsis. For the mock CLP procedure (Sham), mice underwent the same abdominal surgery as CLP procedure, except were not subject to the cecal ligation and puncture. Inhibitor treatments were performed using i.p. injection of the compound at a dose of 2.5 mg/kg body weight. Same amount of DMSO were i.p. injected as a control. Doses were provided at time intervals of in advance of 6 hours, one time injection (single), or repeat injections every 12 hours during the whole experimental period (multiple), as indicted in figure legends. All reagents were balanced with DMSO to provide the same total volume of injecting solution in different mice. Mortality rates were recorded for up to 120 hours for the CLP model and 50-60 hours for the E. coli model after the treatment and dying mice were pre-moved. The statistics analysis was performed by the log rank (Mantel-Cox) test.

Results

Dose Titration of Src Inhibitor In Vitro.

Experiments conducted during the development of embodiments of the technology provided herein indicated that both saracatinib and dasatinib inhibit Src phosphorylation but do not inhibit IKK phosphorylation (FIG. 17). In these experiments, MEFs were pre-treated with different doses of dasatinib or saracatinib for 1 hour (DMSO was used as control), followed with or without cytotoxic TNFα treatment for 15 min. Phosphorylation of Src and IKKb, as well as expression levels of Src, IKKb and b-actin were analyzed by immunoblotting (FIG. 17). As shown in FIG. 17, a high dose (90 nM) of Src inhibitor also inhibits IKKß activity as indicated by detection of IKK phosphorylation. Thus, further experiments were conducted using a dose of 80 nM (e.g., 80 nM saracatinib).

Small Molecule Inhibitors of Src Phosphorylation.

Experiments conducted during the developments of the technology provided herein indicated that compounds provided in Table 1 inhibit Src phosphorylation as strongly as saracatinib ("ZG5108", FIG. 18). Data were collected in experiments in which MEFs were pre-treated with 80 nM of the indicated compounds for 1 hour (DMSO was used as control), followed with or without cytotoxic TNFα treatment for 15 minutes. Phosphorylation of Src, as well as expression levels of Src and ß-actin, were analyzed by immunoblotting.

Small Molecule Src Inhibitors Inhibit BAD Activity in Mitochondria.

Experiments conducted during the development of embodiments of the technology provided herein indicated that both saracatinib and dasatinib inhibit cytotoxic dose TNFα-induced BAD release from cytoskeleton to cytosol and translocation to mitochondria (FIG. 19A, 19B). In these experiments, MEFs were pre-treated with different doses of dasatinib or saracatinib for 1 hour (DMSO was used as control), followed with or without cytotoxic TNFα treatment for 4 hours. Cells were fractionated into cytosol and cytoskeleton (FIG. 19A) or cytosol and mitochondria (FIG. 19B). Subcellular localization of BAD and IKK-phosphorylated BAD("Pbad(S26)") were analyzed by immunoblotting. ß-actin and GAPDH were used as cytosol/cytoskeleton markers; ß-action and COX-2 were used as cytosol/mitochondrial markers.

Small Molecule Src Inhibitors Alleviate Sepsis.

During the development of embodiments of the technology provided herein, experiments were conducted that indicated that small molecule inhibitors of Src (e.g., saracatinib, ZG5129) inhibit bacterial or polymicrobial infection-induced severe sepsis. In these experiments, wild type mice were i.p injected with or without saracatinib (2.5 mg/kg body weight) for 6 hours, then challenged with E. coli (5×10$^7$CFU, i.p. injection). Dying mice were pre-moved. Mortality rate was determined (FIG. 20A); n=6, p<0.01. In additional experiments, wild type mice were i.p. injected with or without ZG5129 (2.5 mg/kg body weight) for 6 hours, and subjected to cecal ligation and puncture (CLP) surgery or Sham procedure. Mice were i.p. injected with ZG5129 (2.5 mg/kg body weight) each 12 hours after surgery. Dying mice were pre-moved. Mortality rate was determined (FIG. 20B); n=10, p<0.01.

Example 20—Role of BAD in Alzheimer's Disease

Alzheimer's disease is one of the most common neuronal degenerative diseases. During the development of embodiments of the technology described herein, experiments were conducted to examine biological mechanisms of Alzheimer's disease. In particular, data were collected that indicated that the BH3-only pro-apoptotic protein BAD is involved in neuronal cell apoptosis and contributed to pathology in a mouse model (5XFAD) of Alzheimer's disease. Loss of Bad significantly reduced the formation of Aß plaques and Aß burden in cortex and hippocampus of 5XFAD mice by inhibiting neurodegeneration and neuronal cell loss.

Methods

Animals.

Heterozygous 5XFAD transgenic AD mice were purchased from Jackson Lab (#006554). These mice overexpress human APP (695) with Swedish (K670N, M6710, Florida (I716V), and London (V7171) mutations; and express human PS1 with M146L and L286V mutations. 5XFAD/Bad$^{-/-}$ mice were generated by crossbreeding Bad$^{-/-}$ mice with 5XFAD mice. Age-matched WT, 5XFAD, and 5XFAD/Bad$^{-/-}$ littermates were used for all experiments and all of the mice were C57/BL6 background. Sample sizes (n) are indicated in the figure legends for each experiment as described below. All animal experiments were approved by the Institutional Animal Care and Use Committee in Shanghai Institute of Biochemistry and Cell Biology.

Behavioral Test.

For the Morris water test, a circular water tank (122 cm diameter and 50 cm high) was filled with water and the water was made opaque with nontoxic white paint. A round platform (12 cm diameter) was hidden 1 cm beneath the surface of water at the center of a given quadrant of the water tank. Invisible platform training was carried out continuously for 6 days (6 sessions with each session consisting of 4 trials). For each trial, mice were released from the wall of the tank and allowed to search, find, and stand on the platform for 20 seconds within a 60-second trial period. Mice that failed to mount the platform were gently guided to the platform and allowed to stand on it for 20 seconds. For each training session, the starting quadrant and sequence of four quadrants from where mice were released into the water tank were randomly chosen, so that the tests were different among separate sessions for each mouse and were different for individual mice. Mice in the water pool were recorded by a video camera. Task performances, including swimming paths, speeds, and time spent in each quadrant, were recorded using an EthoVision video tracking system (Noldus). A probe test was conducted 24 hours after the completion of the invisible platform training. During the probe test, the platform was removed from the pool and task performances were recorded for 60 seconds. The recorded times for mice to cross the region where the platform was placed and the recorded times spent in the target quadrant were analyzed as previously described (Vorhees & Williams (2006) "Morris water maze: procedures for assessing spatial and related forms of learning and memory" Nature Protocols 1: 848, incorporated herein by reference).

Brain Samples Preparation.

Mice were perfused with ice-cold PBS after deep anesthesia. Right-brain hemispheres were fixed in 4% PFA overnight and then placed sequentially in 15% and 30% sucrose overnight to dehydrate the brain tissue. Dehydrated hemispheres were stored at −80° C. for subsequent preparation of frozen sections. Dehydrated right-brain hemispheres were sectioned for serial 30-μm coronal sections using a vibratome (Leica) and stored in anti-freezing solution (0.02 M NaH$_2$PO$_4$, 0.08M Na$_2$HPO$_{4,1}$% PVP-40 (w/v), 30% sucrose (w/v), and 30% ethylene glycol) at −20° C. before staining. Left-brain hemispheres were carefully dissected out and flash frozen in liquid nitrogen for western blot, ELISA, or mRNA expression analysis.

Fluoro-Jade C Staining.

Neuronal degeneration was analyzed by Fluoro-Jade C (AG325, Millipore) staining according to manual instruction with minimal modification. Briefly, free-floating sections were washed 5 times with PBS for 5 minutes each wash to remove anti-freezing solution and then pre-treated sequentially in 80% ethanol containing 1% NaOH for 5 minutes, 70% ethanol for 2 minutes, 50% ethanol for 2 minutes, 30% ethanol for 2 minutes, 10% ethanol for 2 minutes; then, the samples were washed twice with ddH$_2$O for 2 minutes each wash, 0.06% potassium permanganate for 10 minutes, and finally washed twice with ddH$_2$O for 2 minutes each wash. After pre-treating, brain sections were stained with 0.0001% Fluoro-Jade C working solution containing DAPI dye for 20 minutes and then washed thrice with ddH$_2$O to remove extra Fluoro-Jade C solution. Finally, brain sections were recovered in PBS and mounted on slides for analysis.

Nissl Staining.

Neuronal loss in cortical layer 5 and subiculum were detected by Nissl staining using Crystal Violet (C0775, Sigma) as previously described (Eimer & Vassar (2013) "Neuron loss in the 5XFAD mouse model of Alzheimer's disease correlates with intraneuronal Aß42 accumulation and Caspase-3 activation" *Molecular Neurodegeneration* 8:1-12, incorporated herein by reference) with minimal modification. Briefly, brain sections were thoroughly washed with PBS, mounted on charged slides, and allowed to dry overnight. Sections were first rinsed in water and then stained with 0.5% crystal violet for 10 minutes. Then, sections were rinsed in water and dehydrated in 70% ethanol for 5 minutes, 95% ethanol for 1 minutes, and then de-stained in 95% ethanol containing 0.7% glacial acetic acid for 1 minute. Sections were then sequentially washed for 2 minutes in 100% ethanol 2 times, washed in ethanol/xylene (1:1 ratio) for 5 minutes, xylene for 5 minutes, and then mounted for analysis.

Immunohistochemistry.

Hippocampal matched free-floating sections were washed with PBS to thoroughly remove anti-freezing solution, and permeabilized in 0.3% Triton X-100 in PBS for 30 minutes. Sections were blocked in blocking buffer (3% BSA (w/v), 0.3% Triton X-100, and 0.5% normal goat serum in PBS) for 1 hour at room temperature and then incubated with primary antibodies diluted in blocking buffer overnight at 4° C. Primary antibody anti-Iba1 (019-19741) was purchased from Wako; 6E10 antibody for Aß plaques (SIG-39320) was purchased from Covance; anti-GFAP (ab16997) and anti-NeuN (ab177487) antibodies were purchased from Abcam; anti-ASC (#04-147) was purchased from Millipore. Sections were incubated with corresponding Alexa-Fluor 488-labeled and Cy3-labeled secondary antibodies (Molecular Probes) diluted in blocking buffer for 2 hours at room temperature to visualize primary antibodies and incubated with DAPI (Sigma) to visualize cell nuclei. Sections were mounted on microscope slides (Premiere) with fluorescent mounting medium (Dako) and images were collected using a BX51 microscope (Olympus) and Leica TCS SP8 confocal microscope (Leica). For each experimental condition, three to five fields per section and five sequential sections per each mouse were pictured for quantification. All area fraction and cell density quantification analysis was performed using ImageJ software (National Institutes of Health).

Immunoblotting Analysis.

Snap-frozen brain hemispheres were homogenized in RIPA buffer (50 mM Tris-HCl (pH 8.0), 150 mM NaCl, 1% deoxycholic acid sodium salt, 0.1% SDS, 1% NP-40, 1 mM EDTA, and 1 mM EGTA) using Precellys 24 (Bertin Technologies) using a program of 6000 rpm for 3 times of 15 seconds to 30 seconds each. Samples were then rotated at 4° C. for 30 minutes. Brain lysates were centrifuged at 4° C. at 12,000 rpm for 30 minutes to remove cell debris and the protein concentration was determined with a BCA assay. Brain samples were separated by SDS-PAGE gels and proteins were transferred to PVDF membrane (Millipore) at 100 V for 2 hours. Membranes were blocked in 5% (w/v) skim milk or 3% bovine serum albumin diluted in TBS for 1 hour at room temperature, then incubated with primary antibodies overnight at 4° C. and secondary antibodies for 1 hour at room temperature. Primary antibodies anti-CD11b (ab133357), anti-GFAP (ab16997), and anti-PSD-95 (ab18258) were purchased from Abcam; anti-Cleaved caspase-3 (#9661), anti-Phospho-IκBα (#9246), anti-IKKß (#2678), anti-Phospho-IKKα/ß (#2697), anti-Bcl-xL (#2762), anti-14-3-3 (#9636), and anti-BAD (#9292) were purchased from Cell Signaling Technology; anti-Caspase-3 (sc-7148), anti-α-Tubulin (sc-8035), anti-Tom20 (se-11415), anti-IκBα (sc-371), and anti-ß-actin (sc-47778) were purchased from Santa Cruz; 6E10 antibody for total APP and total Aß (SIG-39320) and C1/6.1 antibody for C-terminal fragments of APP (SIG39152) were purchased from Covance. Secondary antibodies HRP-linked anti-rabbit IgG (#7074) and HRP-linked anti-mouse IgG (#7076) were purchased from Cell Signaling Technology. Membranes were exposed by the enhanced chemiluminescence method and signal intensities were quantified by ImageJ, and then normalized to ß-actin. Total soluble Aß was detected by Tricine-SDS-PAGE as previously described (Schagger (2006) "Tricine-SDS-PAGE" *Nature Protocols* 1; 16-22; Obregon (2012) "Soluble amyloid precursor protein-α modulates ß-secretase activity and amyloid-ß generation" *Nature Communications* 3; 777, each of which is incorporated herein by reference). A 10% Tricine gel containing 8-M urea was used for Aß detection, proteins were transferred to 0.2-µm PVDF membrane at 30 V for 2 hours, and then the membrane was boiled in PBS for 5 minutes to enhance sensitivity before blocking and the following procedures were similar to SDS-PAGE.

ELISA.

Aß$_{40}$ Human ELISA Kit (KHB3482, Invitrogen) and Ultrasensitive Aß$_{42}$ Human ELISA Kit (KHB3544, Invitrogen) were used for soluble or insoluble Aß$_{40}$ and Aß$_{42}$ detection. Snap-frozen brain hemispheres were extracted using RIPA buffer for soluble Aß$_{40}$ and Aß$_{42}$, and the pellets were further extracted using 2% SDS for insoluble Aß$_{40}$ and Aß$_{42}$. Protein concentrations of RIPA extracts and SDS extracts were measured by BCA methods. ELISA procedures were performed according to supplier instructions.

Statistics.

Comparisons between two groups were analyzed by two-tailed Student t-test and comparisons among three groups were analyzed by one-way ANOVA test. All data were analyzed by SPSS software. Differences was considered significant when P value<0.05.

Results

Loss of Bad Reduces Aß Plaque Number and Aß Burden in 5XFAD Mice.

During the development of embodiments of the technology described herein, experiments were conducted to assess the deposition of amyloid-ß (Aß) in neuronal cell loss and cerebral neuroinflammation, which contribute to pathogenesis in Alzheimer's disease (AD) patients and AD animal models (Ashe & Zahs (2010) "Probing the biology of Alzheimer's disease in mice" *Neuron* 66: 631-645; Walsh & Selkoe (2004) "Deciphering the molecular basis of memory failure in Alzheimer's disease" *Neuron* 44: 181-193; Biswas et al. (2007) "Bim is elevated in Alzheimer's disease neurons and is required for ß-amyloid-induced neuronal apoptosis" *The Journal of Neuroscience* 27: 893-900; Feng et al. (2015) "AB induces PUMA activation: a new mechanism for AB-mediated neuronal apoptosis" *Neurobiology of Aging* 36: 789-800; Kudo et al. (2012) "Inhibition of Bax protects neuronal cells from oligomeric Aß neurotoxicity" *Cell Death & Disease* 3: e309, each of which is incorporated herein by reference. To determine the role of BAD in Alzheimer's disease, experiments were conducted in which Bad$^{-/-}$ mice were crossbred with 5XFAD transgenic mice, an accelerated mouse model of AD6, to produce 5XFAD/Bad$^{-/-}$ mice (FIG. 21a). Immunofluorescence staining revealed significantly reduced Aß plaque number and Aß burden in cortex and hippocampus, even in whole brain sections of 6-month and 9-month-old 5XFAD/Bad$^{-/-}$ mice (FIG. 22a; FIG. 21b). The reduction was not due to decreased APP expression because the protein level of total APP was not significantly different between 6-month-old 5XFAD and 5XFAD/Bad$^{-/-}$ mice, while the levels of ß-carboxyl-terminal fragment (6-CTF) and total Aß were significantly reduced in 5XFAD/Bad$^{-/-}$ mice compared to that in 5XFAD mice (FIG. 22b, FIG. 22c). Furthermore additional data indicated that both soluble and insoluble Aß$_{40}$ and Aß$_{42}$ were significantly reduced in brain homogenates of 5XFAD/BAD$^{-/-}$ mice than that in 5XFAD mice (FIG. 22d). These results indicate that BAD is involved in the formation and deposition of Aß in the specific brain regions of 5XFAD mice.

Loss of Bad Inhibits Neurodegeneration and Neuronal Loss in 5XFAD Mice.

One of the primary marks of Alzheimer's disease is neuronal cell loss. During the development of embodiments of the technology described herein, data were collected from experiments indicating significant neurodegeneration in cortical layer 5 and hippocampus of 6-month and 9-month-old 5XFAD mouse brains as detected by Fluoro-Jade C (FJC, a neurodegeneration specific marker) (FIG. 23a, FIG. 23b), consistent with previous reports (Chen et al. (2012) "Monoacylglycerol lipase is a therapeutic target for Alzheimer's disease" *Cell Reports* 2: 1329-1339; Rangasamy et al. (2015) "Intranasal delivery of NEMO-binding domain peptide prevents memory loss in a mouse model of Alzheimer's disease" *Journal of Alzheimer's Disease* 47: 385-402, each of which is incorporated herein by reference). By contrast, FJC-positive neurons were significantly reduced in the same brain regions of 5XFAD/Bad$^{-/-}$ mice (FIG. 23a, FIG. 23b). As a result of neurodegeneration, 6XFAD mice had obvious neuronal cell loss in cortical layer 5 of cortex and subiculum of hippocampus of 9-month-old 5XFAD mice, as detected by Nissl staining, consistent with previous reports that showed neuronal loss at the late stage of AD (Oakley et al. (2006) "Intraneuronal ß-amyloid aggregates, neurodegeneration, and neuron loss in transgenic mice with five familial Alzheimer's disease mutations: potential factors in amyloid plaque formation" *The Journal of Neuroscience* 26: 10129-10140; Wang et al. (2015) "TREM2 lipid sensing sustains the microglial response in an Alzheimer's disease model" *Cell* 160: 1061-1071, each of which is incorporated herein by reference). Loss of Bad blocked the neuronal loss completely in cortical layer 5 and partially in subiculum in 9-month-old 5XFAD mice. In addition, 9-month-old 5XFAD mice exhibited neuronal cell loss in dentate gyrus of hippocampus, as detected by staining with a neuronal marker NeuN, and this neuronal loss was also partially rescued in 9-month-old 5XFAD/Bad$^{-/-}$ mice. Taken together, the data indicated that loss of Bad suppresses neurodegeneration during the process of AD and reduces and/or prevents neuronal cell loss in the specific brain regions of aged 5XFAD mice.

Loss of Bad Restores Spatial Learning and Memory in 5XFAD Mice.

The most striking symptom of AD is cognitive deficit. Aged 5XFAD mice are known to demonstrate impaired spatial learning and memory in a Morris water maze test relative to wild-type mice (Chen et al. (2012) "Monoacylglycerol lipase is a therapeutic target for Alzheimer's disease" *Cell Reports* 2: 1329-1339; Yue et. al., (2015) "ESC-Derived Basal Forebrain Cholinergic Neurons Ameliorate the Cognitive Symptoms Associated with Alzheimer's Disease in Mouse Models" *Stem Cell Reports* 5: 776-790, each of which is incorporated herein by reference). To determine whether loss of Bad can improve spatial learning and memory in 5XFAD mice, experiments were conducted using the Morris water maze test. In the training period, 6-month-old 5XFAD/Bad$^{-/-}$ mice performed as well as WT mice and exhibited significantly shorter escape latency from day 3 compared with 5XFAD mice (FIG. 24a). This was not the result of different swimming speeds among these three groups (FIG. 24b). In the probe test, 5XFAD/Bad$^{-/-}$ mice performed as well as wild-type mice, spending significantly longer time in the target quadrant and having a greater number of target crossing times compared with 5XFAD mice (FIG. 24c, FIG. 24d). These results indicated that loss of Bad restores the spatial learning ability and memory in 5XFAD mice.

In sum, data collected from experiments conducted during the development of embodiments of the technology described herein indicated that targeting BAD-mediated apoptosis provides a strategy to prevent and/or treat neurodegenerative diseases, e.g., Alzheimer's disease and other neurodegenerative diseases such as Zika viral infection-induced neuronal cell death.

Example 21—Role of BAD in Transplantation

Transplantation is the act of transferring cells, tissues, or organs from one site to another. The immune system remains the most formidable barrier to transplantation as a routine medical treatment. The immune response to a transplanted organ comprises both cellular (lymphocyte mediated) and humoral (antibody mediated) mechanisms. T cells are central in the rejection of grafts—e.g., depletion of T cells could totally eliminate the transplant rejection. During cell-mediated transplant rejection, cytotoxic lymphocytes are involved in antigen specific killing (e.g., direct cell-cell contact), secretory pathways causing cell lysis and/or apoptosis, and ligand induced apoptosis mediated by Fas ligand; and microphages are involved in an antigen non-specific manner, e.g., by phagocytosis, release of soluble factors (e.g., ROS, proteases, TNF, etc.), and production of a local inflammation environment that promotes lymphocyte infiltration. During humoral-mediated transplant rejection, antibody mediated rejection comprises, e.g., activation of the complement cascade via the classical pathway, attraction of inflammatory cells, and stimulation of NK cell and CTLs to kill target cells through ADCC. Various mechanisms related to transplant rejection are associated with transplantee death, including graft failure, vasculopathy, infection, and acute rejection.

Accordingly, immunosuppressant and other drugs are typically taken by the transplantee for the lifetime of the transplanted organ to prevent post-transplant complications. Immunosuppressant drugs suppress the immune system and minimize immune-related complications of transplant. Other medications are typically administered, including anti-platelet therapy, drugs to address drug-induced hyperlipidemia, drugs to treat drug-induced osteoporosis, and to protect the gastrointestinal tract from the effects of prescribed steroids.

Accordingly, experiments were conducted during the development of embodiments of the technology described herein to test the role of Bad in host-versus-graft disease. In particular, experiments were conducted to determine if a reduction of Bad (e.g., by a Bad knockout) reduces cell death mediated by local inflammation in a graft and/or if reduction of Bad (e.g., by a Bad knockout) delays the recruitment of lymphocytes to the graft, thereby reducing cell death and disease associated molecular patterns (DAMPs).

Experiments were conducted and data were collected from standard assays used to study transplantation rejection, e.g., graft survival curves, assay of cytokine expression (e.g., use of Q-PCR for local inflammation), and staining graft infiltrated lymphocytes using, e.g., H&E staining, luna staining (Mast cell), and specific antibody staining (e.g., F4/80 (Microphage), CD4 (Helper T cell), CD8 (cytotoxic T cell), and B220 (Mature B cell).

Results

Bad$^{-/-}$ Graft Heart are More Resistant to Transplantation Rejection.

Loss of Bad significantly protected hearts from transplantation rejection. FIG. 25A shows a survival curve of grafted hearts from Bad knockout or their WT littermates (all C57/B6 background) to Balb/c receipt mice (days post-transplantation). When hearts stopped beating, they were considered to be dead. The protection is not due to suppression of the production of pro-inflammatory cytokines. FIG. 25B shows local cytokine expression profiles of grafted hearts and host hearts, measured by real-time PCR.

Further, haemotoxylin and eosin (H&E) staining was used to stain control non-transplanted WT littermate grafted or Bad knockout grafted hearts. Samples were collected at the end point of the transplantation, e.g., the time the heart stopped beating. WT grafted heart were assessed at day 6.5 and Bad knockout grafted heart was assessed at day 9. The results indicated that loss of Bad significantly inhibits tissue damage of grafted hearts.

Bad$^{-/-}$ Grafted Hearts have Less Lymphocyte Infiltration.

Immunohistochemistry (IHC) staining of WT littermate and Bad knockout grafted hearts with anti-CD4 or anti-CD8 antibody was used to assessed samples collected at the end point of the transplantation (grafted hearts stop beating). Immunostaining of CD4+ and CD8+ T cells in WT littermate and Bad knockout grafted hearts indicated that loss of Bad significantly inhibits T cell-mediated tissue damage of grafted hearts (FIG. 26). The numbers of positive cells were counted in three different random areas for both types of mice.

Transplantation Significantly Induces BAD Mitochondrial Translocation for Apoptosis.

Transplantation induces BAD mitochondrial translocation. WT littermate and Bad knockout grafted hearts were isolated at the end point. Heart tissue extracts were separated into the cytosol and mitochondria by the cytosol and mitochondrial fractionation kit. BAD mitochondrial translocation was detected by immunoblotting using anti-BAD antibody and quantitated by ImageJ program. b-actin and COX-2 were used as markers for the cytosol and mitochondria, respectively. As shown in FIG. 27, transplantation induces significant mitochondrial translocation of BAD, which is known for being able to induce mitochondrial death pathway.

Re-Transplantation.

During the development of embodiments of the technology provided herein, experiments were conducted to assess if WT littermate hearts already show damage early after transplant (e.g., at day 5 post first transplantation), but Bad$^{-/-}$ hearts are still intact (e.g., do not show damage). Accordingly data were collected by evaluating hearts after second round transplantation to measure damage in WT and Bad$^{-/-}$ hearts. A first transplantation was performed using C57 heart transplanted into Balb\c; then, the grafted hearts of WT littermate and Bad knockout mice were removed from the receipts and re-transplanted again to naïve balb\c recipients. Photos were taken before and after the second transplantation surgery; the data indicated that Bad but not WT heart beats normally at day 5 post transplantation and after re-transplantation. In addition, movies were taken before and after the second transplantation surgery. Analysis of the movies indicated that only Bad knockout hearts beat normally with regular rhythms.

Loss of Bad Renders Grafted Hearts Functioning for a Longer Time than the Hearts of WT Littermates.

Graft survival curves were produced from data collected in the re-transplantation experiments described above. The data indicated that after a single (first) transplantation, WT survival was approximately 7.25 days and Bad$^{-/-}$ survival was approximately 8.625 days (FIG. 28). After the second transplantation, WT survival was approximately 6.25 days and Bad$^{-/-}$ survival was approximately 8.75 days (FIG. 28). The data indicated that the Bad knock out heart remained, but the WT heart has reduced functionality after re-transplantation. In particular, Bad knockout heart maintains beating in two consecutive transplantations (8.625 days and 8.75 days), while WT heart beats for an even shorter period after second transplantation (7.25 days and 6.25 days).

REFERENCES

The following references are incorporated herein by reference.

1. K. J. Tracey, A. Cerami, Tumor necrosis factor: a pleiotropic cytokine and therapeutic target. Annual review of medicine 45, 491-503 (1994).
2. C. A. Smith, T. Farrah, R. G. Goodwin, The TNF receptor superfamily of cellular and viral proteins: activation, costimulation, and death. Cell 76, 959-962 (1994).
3. L. A. Tartaglia, D. V. Goeddel, Two TNF receptors. Immunology today 13, 151-153 (1992);
4. R. M. Locksley, N. Killeen, M. J. Lenardo, The TNF and TNF receptor superfamilies: integrating mammalian biology. Cell 104, 487-501 (2001).
5. M. Karin, A. Lin, NF-kappaB at the crossroads of life and death. Nature immunology 3, 221-227 (2002).
6. J. Liu, A. Lin, Wiring the cell signaling circuitry by the NF-kappa B and JNK1 crosstalk and its applications in human diseases. Oncogene 26, 3267-3278 (2007).
7. K. Lei, R. J. Davis, JNK phosphorylation of Bim-related members of the Bcl2 family induces Bax-dependent apoptosis. Proceedings of the National Academy of Sciences of the United States of America 100, 2432-2437 (2003).

8. J. Yan, J. Xiang, Y. Lin, J. Ma, J. Zhang, H. Zhang, J. Sun, N. N. Danial, J. Liu, A. Lin, Inactivation of BAD by IKK inhibits TNFalpha-induced apoptosis independently of NF-kappaB activation. Cell 152, 304-315 (2013).
9. D. C. Huang, A. Strasser, BH3-Only proteins—essential initiators of apoptotic cell death. Cell 103, 839-842 (2000).
10. N. N. Danial, S. J. Korsmeyer, Cell death: critical control points. Cell 116, 205-219 (2004).
11. R. J. Youle, A. Strasser, The BCL-2 protein family: opposing activities that mediate cell death. Nature reviews. Molecular cell biology 9, 47-59 (2008).
12. N. N. Danial, BAD: undertaker by night, candyman by day. Oncogene 27 Suppl 1, S53-70 (2008).
13. B. Beutler, A. Cerami, Cachectin and tumour necrosis factor as two sides of the same biological coin. Nature 320, 584-588 (1986).
14. K. J. Tracey, A. Cerami, Tumor necrosis factor: an updated review of its biology. Critical care medicine 21, S415-422 (1993).
15. A. J. Ridley, A. Hall, The small GTP-binding protein rho regulates the assembly of focal adhesions and actin stress fibers in response to growth factors. Cell 70, 389-399 (1992).
16. E. Kakiashvili, Q. Dan, M. Vandermeer, Y. Zhang, F. Waheed, M. Pham, K. Szaszi, The epidermal growth factor receptor mediates tumor necrosis factor-alpha-induced activation of the ERK/GEF-H1/RhoA pathway in tubular epithelium. The Journal of biological chemistry 286, 9268-9279 (2011).
17. A. J. Ridley, H. F. Paterson, C. L. Johnston, D. Diekmann, A. Hall, The small GTP-binding protein rac regulates growth factor-induced membrane ruffling. Cell 70, 401-410 (1992).
18. A. J. Ridley, A. J. Self, F. Kasmi, H. F. Paterson, A. Hall, C. J. Marshall, C. Ellis, rho family GTPase activating proteins p190, bcr and rhoGAP show distinct specificities in vitro and in vivo. The EMBO journal 12, 5151-5160 (1993).
19. J. H. Chang, S. Gill, J. Settleman, S. J. Parsons, c-Src regulates the simultaneous rearrangement of actin cytoskeleton, p190RhoGAP, and p120RasGAP following epidermal growth factor stimulation. The Journal of cell biology 130, 355-368 (1995).
20. I. T. Lee, S. F. Luo, C. W. Lee, S. W. Wang, C. C. Lin, C. C. Chang, Y. L. Chen, L. Y. Chau, C. M. Yang, Overexpression of HO-1 protects against TNF-alpha-mediated airway inflammation by down-regulation of TNFR1-dependent oxidative stress. The American journal of pathology 175, 519-532 (2009).
21. H. R. Bourne, D. A. Sanders, F. McCormick, The GTPase superfamily: a conserved switch for diverse cell functions. Nature 348, 125-132 (1990).
22. M. Majetschak, S. Flohe, U. Obertacke, J. Schroder, K. Staubach, D. Nast-Kolb, F. U. Schade, F. Stuber, Relation of a TNF gene polymorphism to severe sepsis in trauma patients. Annals of surgery 230, 207-214 (1999).
23. K. J. Van Zee, T. Kohno, E. Fischer, C. S. Rock, L. L. Moldawer, S. F. Lowry, Tumor necrosis factor soluble receptors circulate during experimental and clinical inflammation and can protect against excessive tumor necrosis factor alpha in vitro and in vivo. Proceedings of the National Academy of Sciences of the United States of America 89, 4845-4849 (1992).
24. D. Rittirsch, M. S. Huber-Lang, M. A. Flierl, P. A. Ward, Immunodesign of experimental sepsis by cecal ligation and puncture. Nature protocols 4, 31-36 (2009).
25. T. Secher, V. Vasseur, D. M. Poisson, J. A. Mitchell, F. Q. Cunha, J. C. Alves-Filho, B. Ryffel, Crucial role of TNF receptors 1 and 2 in the control of polymicrobial sepsis. Journal of immunology 182, 7855-7864 (2009).
26. E. Guivier, M. Galan, A. R. Salvador, A. Xuereb, Y. Chaval, G. E. Olsson, S. Essbauer, H. Henttonen, L. Voutilainen, J. F. Cosson, N. Charbonnel, Tnf-alpha expression and promoter sequences reflect the balance of tolerance/resistance to Puumala hantavirus infection in European bank vole populations. Infection, genetics and evolution journal of molecular epidemiology and evolutionary genetics in infectious diseases 10, 1208-1217 (2010).
27. H. Ohman, A. Tiitinen, M. Halttunen, M. Lehtinen, J. Paavonen, H. M. Surcel, Cytokine polymorphisms and severity of tubal damage in women with Chlamydia-associated infertility. The Journal of infectious diseases 199, 1353-1359 (2009).
28. S. K. Mazmanian, J. L. Round, D. L. Kasper, A microbial symbiosis factor prevents intestinal inflammatory disease. Nature 453, 620-625 (2008).
30. Gimenez-Cassina et al. Regulation of hepatic energy metabolism and gluconeogenesis by BAD. Cell Metab. 19, 272-284 (2014).
31. Liu, J. Minemoto, Y. Lin A. c-Jun N-terminal protein kinase 1 (JNK1), but not JNK2, is essential for tumor necrosis factor a-induced c-Jun kinase activation and apoptosis. Mol Cell Biol. 24, 10844-10856 (2004).
32. Melendez et al. RhoA GTPase is dispensable for actomyosin regulation but is essential for mitosis in primary mouse embryonic fibroblasts. J. Biol. Chem. 286, 15132-15137 (2011).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

I claim:

1. A composition comprising a compound according to the structure

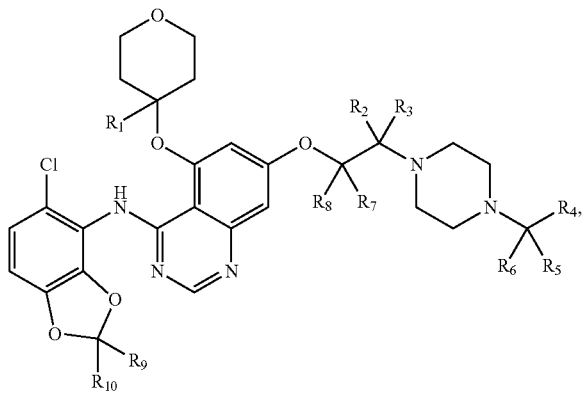

wherein one or more of $R_1$, $R_2$, $R_3$, $R_4$, $R_5$, $R_6$, $R_7$, $R_8$, $R_9$, or $R_{10}$ is a deuterium.

2. The composition of claim 1 wherein each of $R_2$, $R_3$, $R_7$, and $R_8$ is a deuterium.

3. The composition of claim 1 wherein each of $R_2$ and $R_3$ is a deuterium.

4. The composition of claim 1 wherein each of $R_9$ and $R_{10}$ is a deuterium.

5. The composition of claim 1 wherein each of $R_4$, $R_5$, and $R_6$ is a deuterium.

6. The composition of claim 1 wherein each of $R_7$ and $R_8$ is a deuterium.

7. The composition of claim 1 wherein each of $R_2$, $R_3$, $R_7$, $R_8$, $R_9$, and $R_{10}$ is a deuterium.

8. The composition of claim 1 wherein $R_1$ is a deuterium.

9. The composition of claim 1 wherein each of $R_4$, $R_5$, $R_6$, $R_9$, and $R_{10}$ is a deuterium.

10. The composition of claim 1 wherein each of $R_1$, $R_9$, and $R_{10}$ is a deuterium.

11. The composition of claim 1 wherein each of $R_1$, $R_2$, $R_3$, $R_4$, $R_5$, $R_6$, $R_7$, $R_8$, $R_9$, and $R_{10}$ is a deuterium.

12. The composition of claim 1 wherein each of $R_1$, $R_4$, $R_5$, $R_6$, $R_9$, and $R_{10}$ is a deuterium.

13. The composition of claim 1 wherein each of $R_2$, $R_3$, $R_4$, $R_5$, $R_6$, $R_7$, $R_8$, $R_9$, and $R_{10}$ is a deuterium.

14. A method for reducing TNFα cytotoxicity in a subject, the method comprising administering to the subject a deuterated compound having a structure according to

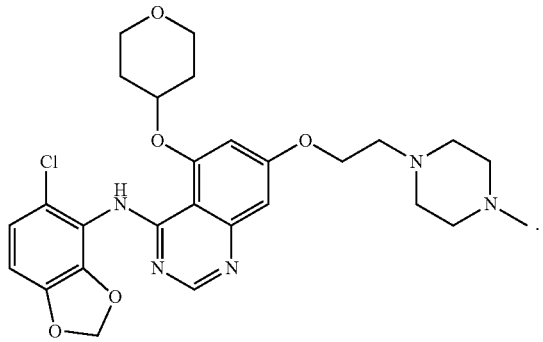 [SMILES: CN1CCN(CCOc2cc(OC3CCOCC3)c3c(Nc4c(Cl)ccc5c4OCO5)ncnc3c2)CC1]

15. The method of claim 14 wherein:
a) one or more of $R_1$, $R_2$, $R_3$, $R_4$, $R_5$, $R_6$, $R_7$, $R_8$, $R_9$, or $R_{10}$ is a deuterium;
b) each of $R_2$, $R_3$, $R_7$, and $R_8$ is a deuterium;
c) each of $R_2$ and $R_3$ is a deuterium;
d) each of $R_9$ and $R_{10}$ is a deuterium;
e) each of $R_4$, $R_5$, and $R_6$ is a deuterium;
f) each of $R_7$ and $R_8$ is a deuterium;
g) each of $R_2$, $R_3$, $R_7$, $R_8$, $R_9$, and $R_{10}$ is a deuterium;
h) $R_1$ is a deuterium;
i) each of $R_4$, $R_5$, $R_6$, $R_9$, and $R_{10}$ is a deuterium;
j) each of $R_1$, $R_9$, and $R_{10}$ is a deuterium;
k) each of $R_1$, $R_2$, $R_3$, $R_4$, $R_5$, $R_6$, $R_7$, $R_8$, $R_9$, and $R_{10}$ is a deuterium;
l) each of $R_1$, $R_4$, $R_5$, $R_6$, $R_9$, and $R_{10}$ is a deuterium; and/or
m) each of $R_2$, $R_3$, $R_4$, $R_5$, $R_6$, $R_7$, $R_8$, $R_9$, and $R_{10}$ is a deuterium in a structure according to

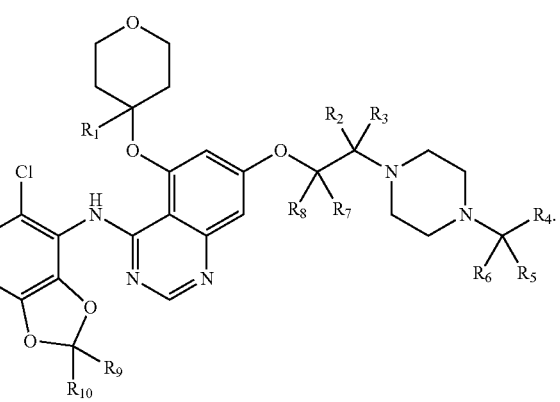

16. A pharmaceutical composition comprising a composition according to claim 1.

17. The pharmaceutical composition of claim 16 formulated for administration to a human.

18. The method of claim 14 further comprising testing the subject for a microbial infection, sepsis, apoptosis, tissue or organ damage, rheumatoid arthritis, amyloid-beta, Alzheimer's disease, activation of Src, inflammatory disease, autoimmune disease, cancer, actin depolymerization, or transplant rejection.

19. The method of claim 18 further comprising a second administering of said compound to said subject.

20. The method of claim 14 wherein testing said subject comprises testing a sample from said subject.

* * * * *